(12) United States Patent
Saunders et al.

(10) Patent No.: US 7,829,589 B2
(45) Date of Patent: Nov. 9, 2010

(54) SULFONAMIDE COMPOUNDS AND USES THEREOF

(75) Inventors: Jeffrey O. Saunders, Acton, MA (US); Thomas Coulter, Wantage (GB); Paul Mortenson, Royston (GB); Manuel A. Navia, Boston, MA (US); Jean-Francois Pons, Abingdon (GB)

(73) Assignee: Elixir Pharmaceuticals, Inc., Cambridge, MA (US)

( * ) Notice: Subject to any disclaimer, the term of this patent is extended or adjusted under 35 U.S.C. 154(b) by 680 days.

(21) Appl. No.: 11/564,815

(22) Filed: Nov. 29, 2006

(65) Prior Publication Data

US 2007/0270473 A1    Nov. 22, 2007

Related U.S. Application Data

(63) Continuation-in-part of application No. 11/451,086, filed on Jun. 12, 2006, now abandoned.

(60) Provisional application No. 60/689,709, filed on Jun. 10, 2005.

(51) Int. Cl.
  *A61K 31/4196* (2006.01)
  *C07D 249/08* (2006.01)

(52) U.S. Cl. .................................. 514/383; 548/267.2

(58) Field of Classification Search .................. 514/383; 548/267.2

See application file for complete search history.

(56) References Cited

U.S. PATENT DOCUMENTS

| | | | |
|---|---|---|---|
| 3,635,982 A | 1/1972 | Potoski et al. | |
| 5,180,723 A | 1/1993 | Whittaker et al. | |
| 5,254,715 A | 10/1993 | Picard et al. | ........... 560/13 |
| 5,336,690 A | 8/1994 | Picard et al. | ........... 514/605 |
| 6,610,707 B1 | 8/2003 | Bull et al. | |
| 2002/0107255 A1 | 8/2002 | Blumberg et al. | |
| 2005/0261332 A1 | 11/2005 | Distefano et al. | |

FOREIGN PATENT DOCUMENTS

| | | |
|---|---|---|
| EP | 1798226 | 6/2007 |
| WO | 93/14072 | 7/1993 |
| WO | 93/16075 | 8/1993 |
| WO | 99/45006 | 9/1999 |
| WO | WO 00/54729 | 9/2000 |
| WO | 02/50046 | 6/2002 |
| WO | 03/105855 | 12/2003 |
| WO | 2004/021984 | 3/2004 |
| WO | 2004/103993 | 12/2004 |
| WO | 2005/097788 | 10/2005 |
| WO | 2006/135860 | 12/2006 |
| WO | 2007/146914 | 12/2007 |

OTHER PUBLICATIONS

Asakawa et al., "Antagonism of ghrelin receptor reduces food intake and body weight gain in mice", Gut, 2003; 52:947-952.
Brouwer et al., "Synthesis of Cyclic Peptidosulfonamides by Ring-Closing Metathesis", J. Org. Chem., 2004, 69, 3662-3668.
Esler et al., "Small-Molecule Ghrelin Receptor Antagonists Improve Glucose Tolerance, Suppress Appetite, and Promote Weight Loss", Endocrinology 148(11):5175-5185.
European Search Report dated Jun. 25, 2009 from EP Application No. 06784776.
International Search Report dated Oct. 25, 2006 from PCT/US06/22789.
International Search Report dated Nov. 15, 2007 from PCT/US07/70959.
Makara et al., "Michael addition of amines to vinyl sulfonamides on solid support", Tetrahedron Letters 42 (2001) 4123-4125.

*Primary Examiner*—Joseph R Kosack
(74) *Attorney, Agent, or Firm*—Lando & Anastasi, LLP

(57) ABSTRACT

Compounds that modulate GHS-R are described, for examples compounds formula (I)

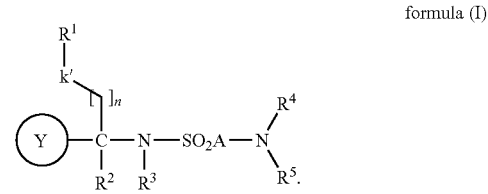

formula (I)

16 Claims, 13 Drawing Sheets

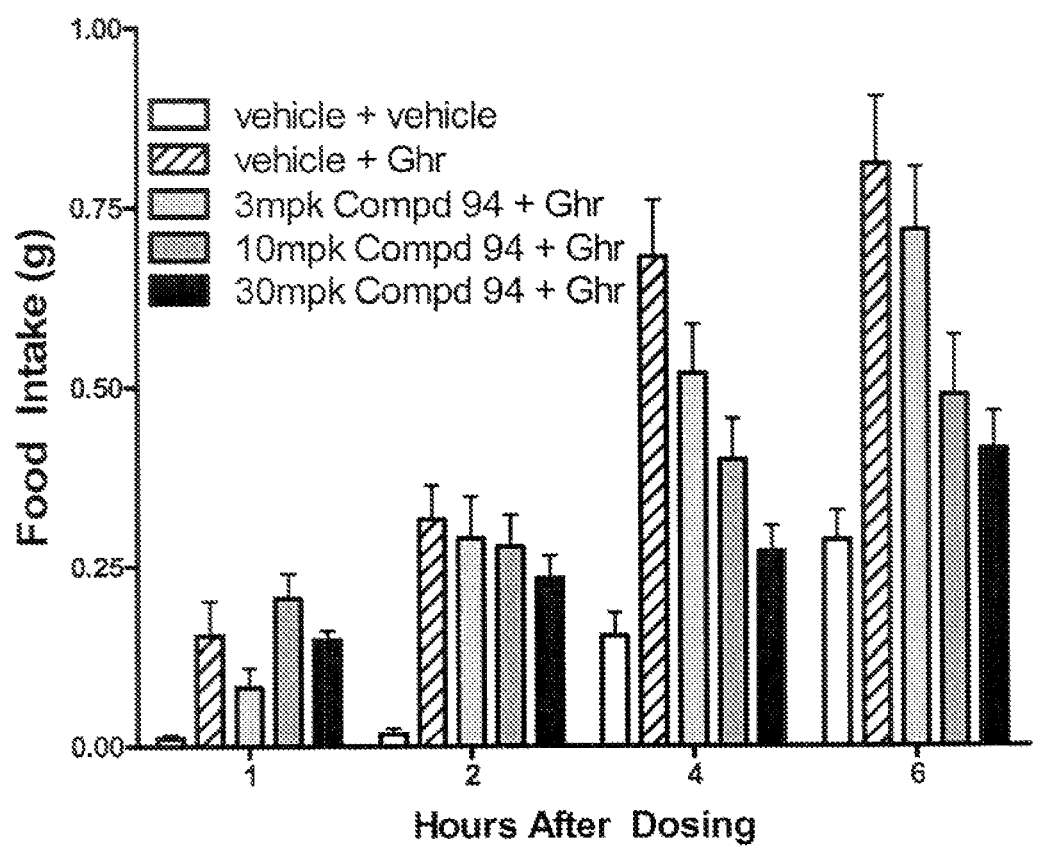
Figure 2: Triazole GhrR antagonists block ghrelin-induced food intake in mice Figure 4a: baseline fasted blood glucose levels
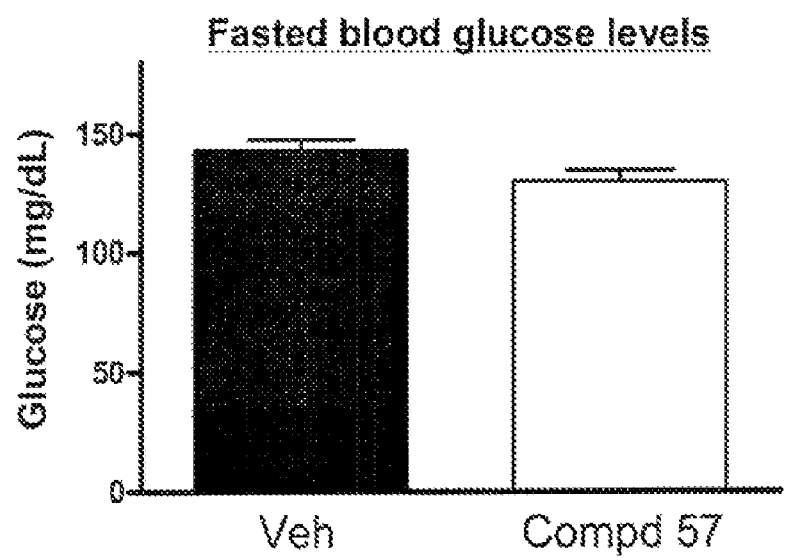

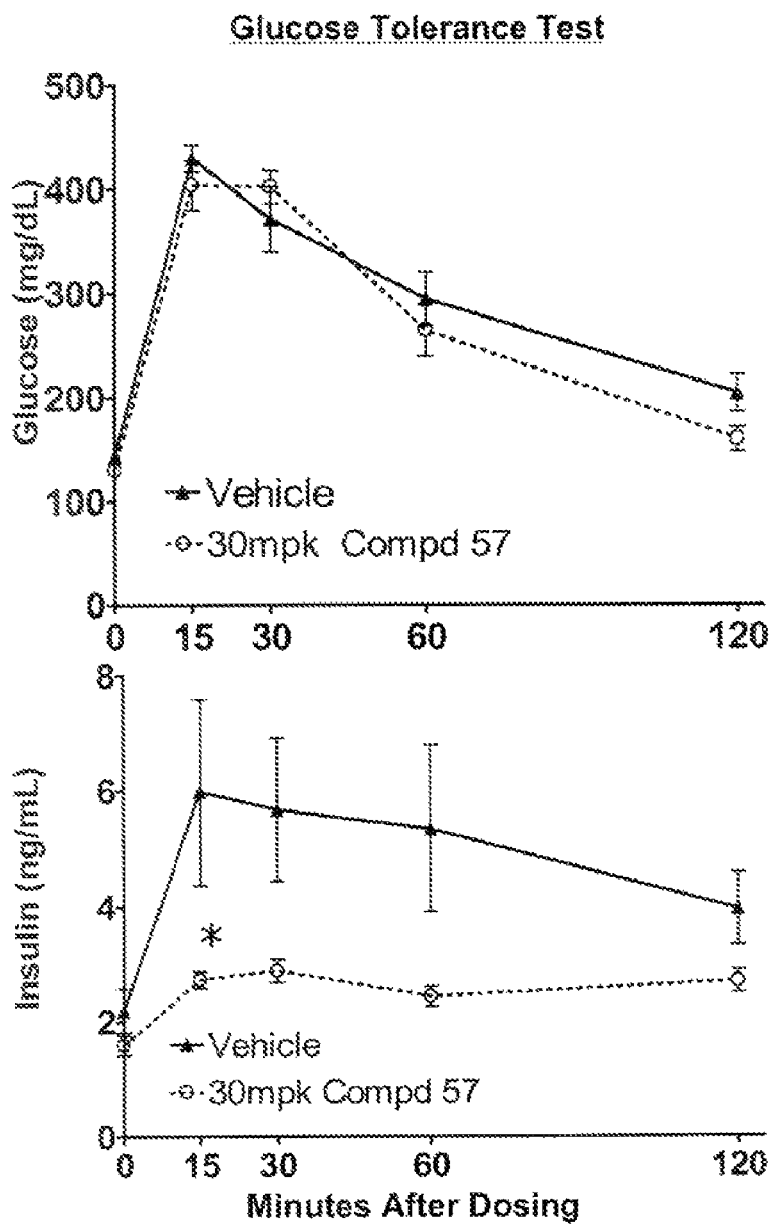
Figure 4b: 7 days oral dosing of compound 57 improves insulin sensitivity

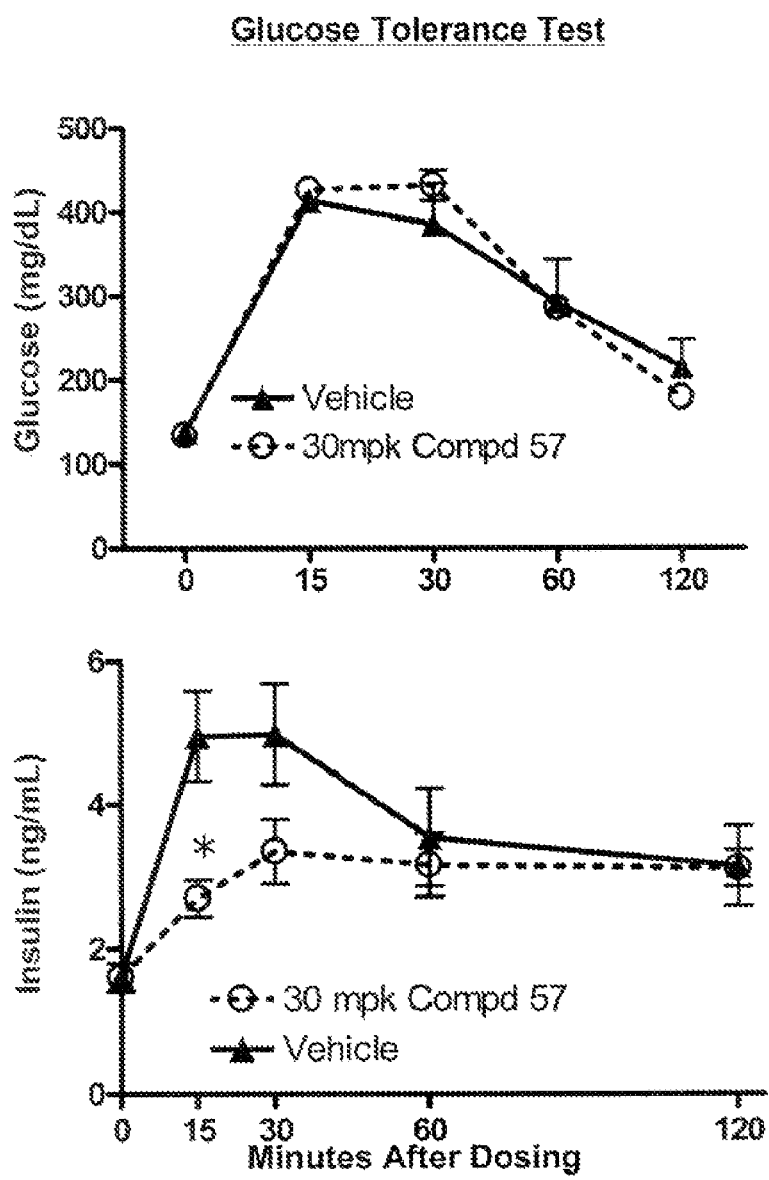
Figure 4c: 21 days oral dosing of compound 57 antagonists improves insulin sensitivity Figure 4d: baseline fasted blood glucose levels
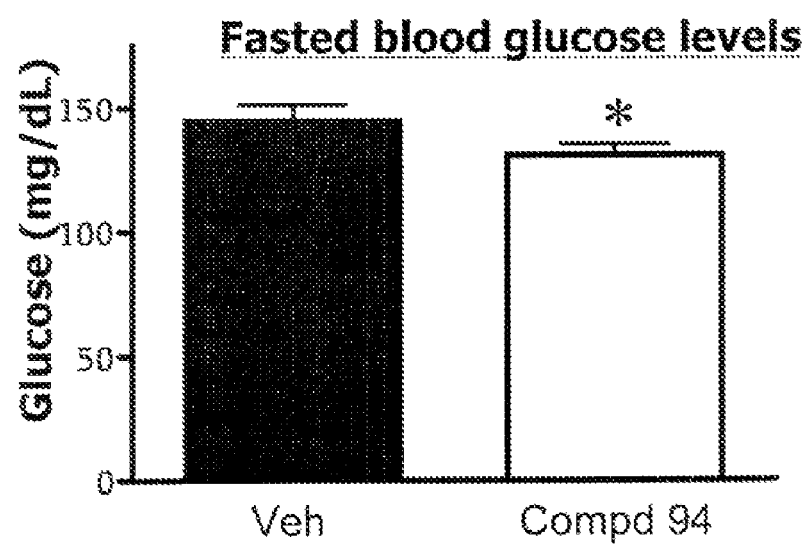

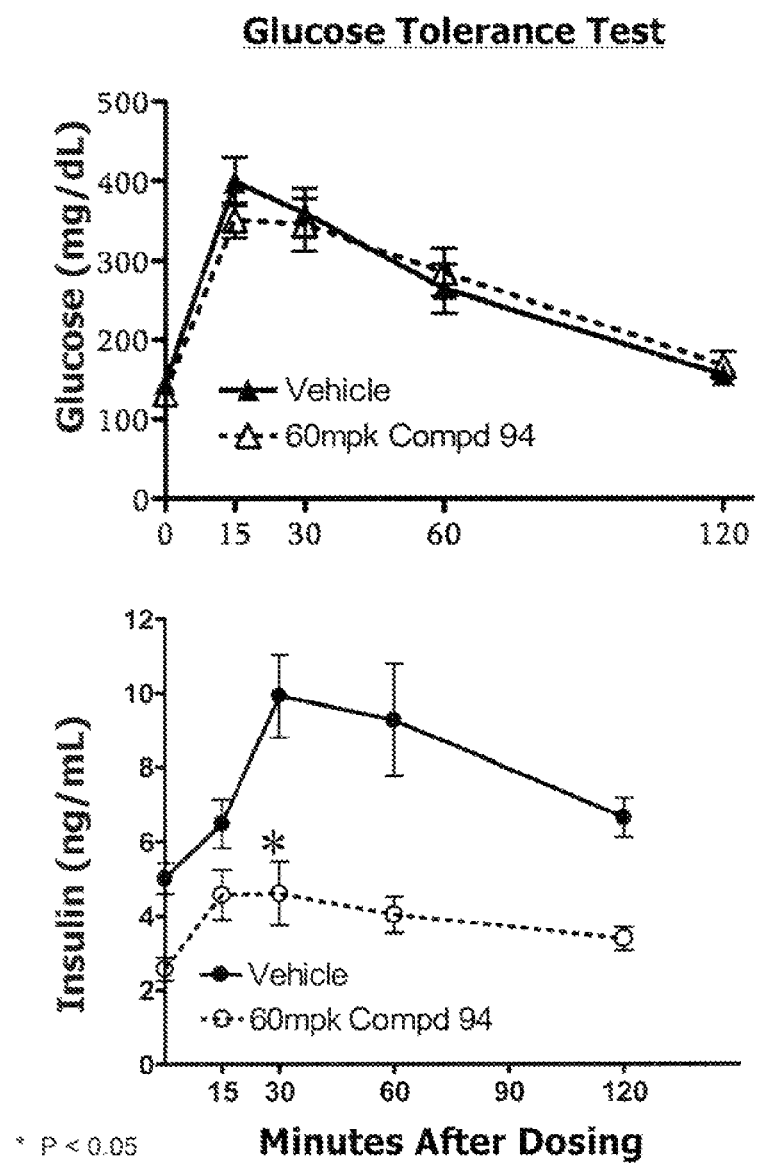
Figure 4e: 7 days oral dosing of compound 94 improves insulin sensitivity Figure 4f: 28 days oral dosing of compound 94 improves insulin sensitivity in a Glucose tolerance test (GTT)
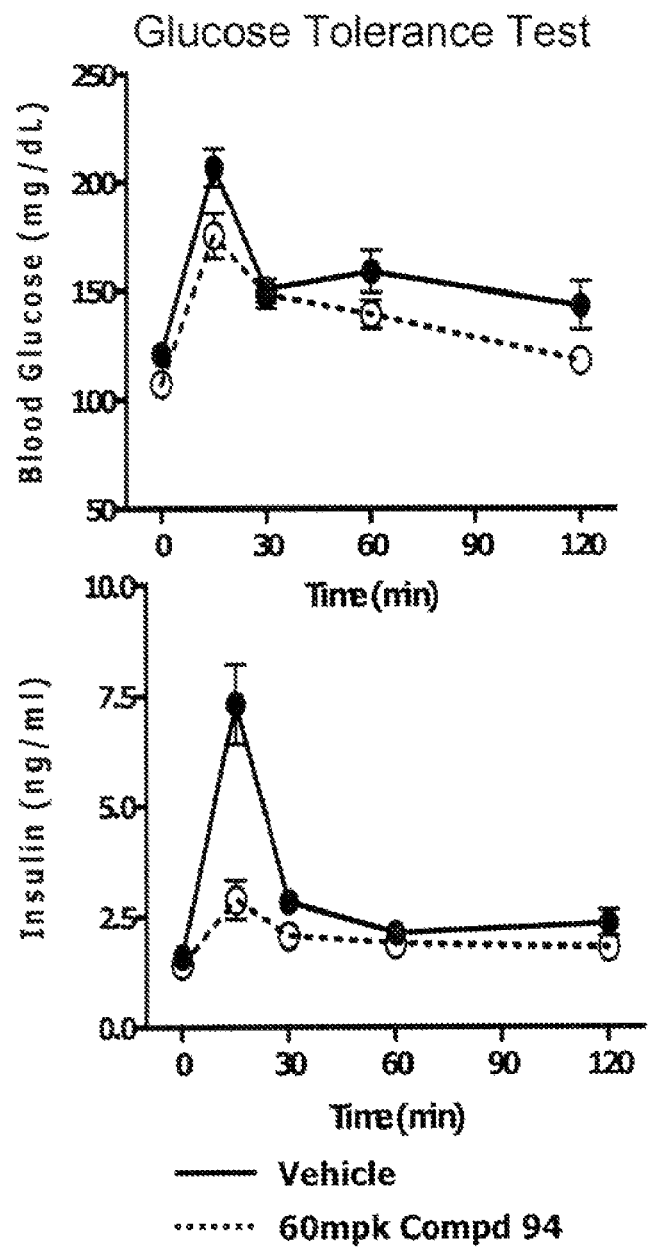

Figure 5: 28 day dosing of compound 57 results in improved plasma HbA1c and cholesterol levels.
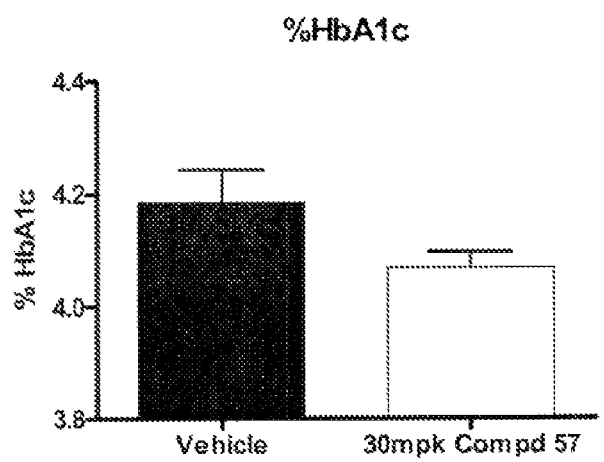
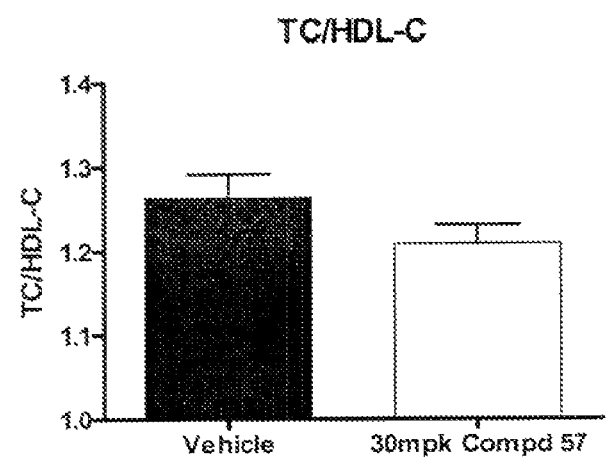
Plasma analysis

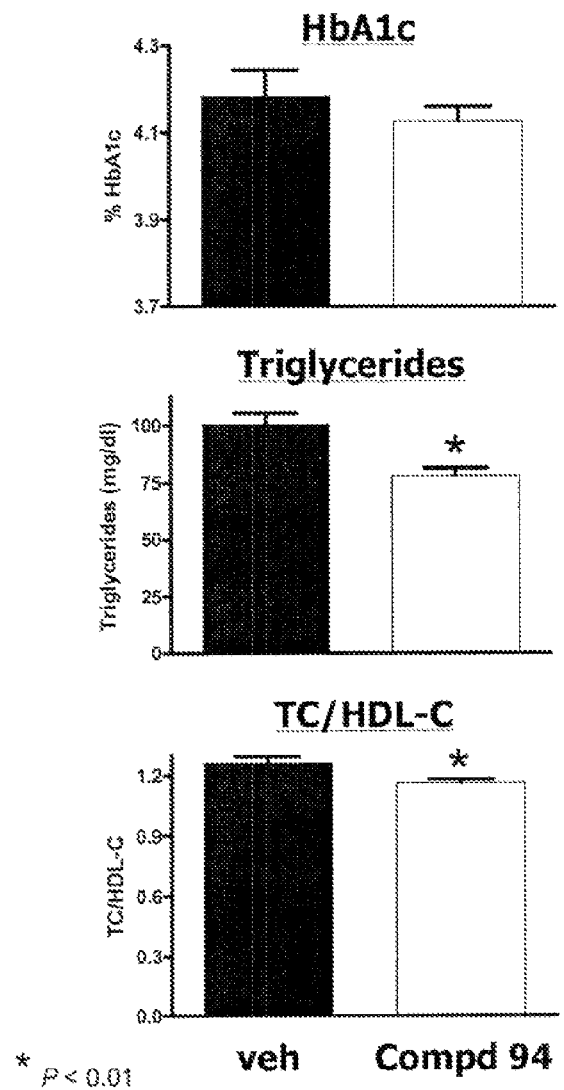
Figure 6: 28 day dosing of triazole ghrelin antagonists results in improved plasma HbA1c, triglyceride and cholesterol levels.
Plasma analysis Fasted blood glucose levels before and after 14 days of oral bid treatment with a GhrR antagonist

SULFONAMIDE COMPOUNDS AND USES THEREOF

CLAIM OF PRIORITY

This application is a continuation-in-part of U.S. patent application Ser. No. 11/451,086, filed Jun. 12, 2006 now abandoned, which claims priority under 35 USC §119(e) to U.S. Patent Application Ser. No. 60/689,709, filed on Jun. 10, 2005, the entire contents of each of which are hereby incorporated by reference.

BACKGROUND

The growth hormone secretagogue receptor (GHS-R) regulates a number of physiological processes, including growth hormone (GH) release, metabolism, and appetite. Ghrelin is a 28 amino acid peptide that is an endogenous ligand for the growth hormone secretagogue receptor (GHS-R) also known as the ghrelin receptor. Ghrelin has been shown to stimulate feeding in humans. In rodents, ghrelin induces body weight gain and adiposity. See, e.g., Asakawa (2003) Gut 52:947. In addition to regulating feeding, ghrelin can stimulate GH secretion by activating GHS-R, particularly in somatotrophic tissue.

Accordingly, compounds that modulate GHS-R activity are at least useful for controlling disorders associated with GHS-R physiology.

SUMMARY

The invention relates, inter alia, to useful compounds and compositions that modulate GHS-R, as well as methods of using and making the compounds. Some examples of the compounds include sulfonamide compounds, for example heteroaryl sulfonamide compounds, and other sulfonamide compounds having cyclic moieties. Examples of heteroaryl compounds include oxadiazole and triazole compounds. The compounds can be used in therapeutic applications, including modulation of disorders, diseases or disease symptoms in a subject (e.g., mammal, human, dog, cat, horse). The compounds include useful GHS-R antagonists. Such antagonists can be used, e.g., to reduce feeding in a subject.

The compounds, including stereoisomers thereof, can be created either singly, in small clusters, or in a combinatorial fashion to give structurally diverse libraries of compounds.

In one aspect, the invention features a compound of formula (I)

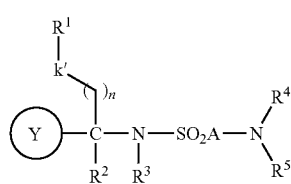

formula (I)

wherein, $R^1$ is hydrogen, halo (e.g., fluoro), aryl, heteroaryl, arylalkyl, heteroarylalkyl, cyclyl, cyclylalkyl, heterocyclyl, heterocyclylalkyl, alkyl, alkenyl, alkynyl, or $R^1$ can be taken together with $R^2$ or $R^3$ to form a ring; each of which is optionally substituted with 1-4 $R^6$;

k' is a bond, O, C(O), C(O)O, OC(O), C(O)NR$^3$, NR$^3$C(O), S, SO, SO$_2$, CR$^2$=CR$^2$, or C≡C;

n is 0-6, preferably 1-3;

$R^2$ is hydrogen, halo (e.g., fluoro), $C_1$-$C_6$ alkyl, $C_2$-$C_6$ alkenyl, or $C_2$-$C_6$ alkynyl; or $R^2$ can be taken together with $R^1$ to form a ring;

$R^3$ is hydrogen, $C_1$-$C_6$ alkyl, $C_2$-$C_6$ alkenyl, or $C_2$-$C_6$ alkynyl, or $R^3$ can be taken together with $R^2$, $R^4$, or $R^5$ to form a ring; each of which can be optionally substituted with 1-2 $R^{6'}$;

A is

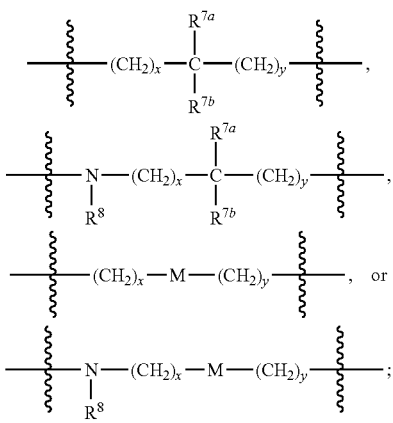

x and y are each independently 0-6;

M is aryl, heteroaryl, cyclyl, or heterocyclyl, each of which is optionally substituted with 1-4 $R^9$;

$R^4$ and $R^5$ are each independently hydrogen, alkyl, alkenyl, haloalkyl, cyclyl, or heterocyclyl, or $R^4$ and $R^5$ can be taken together to form a heterocyclic ring, or $R^4$ and $R^5$ can be taken together to form an azido moiety, or one or both of $R^4$ and $R^5$ can independently be joined to one or both or $R^{7a}$ and $R^{7b}$ to form one or more bridges between the nitrogen to which the $R^4$ and $R^5$ are attached and $R^{7a}$ and $R^{7b}$, wherein each bridge contains 1 to 5 carbons; or one or both of $R^4$ and $R^5$ can independently be joined to one or both of $R^{7a}$ and $R^{7b}$ to form to form one or more heterocyclic rings including the nitrogen to which the $R^4$ and $R^5$ are attached, or one or both of $R^4$ and $R^5$ can independently be joined to $R^3$ to form a ring, or one or both of $R^4$ and $R^5$ can independently be joined to $R^8$ to form a ring; wherein each $R^4$ and $R^5$ are optionally independently substituted with 1-5 halo, 1-3 hydroxy, 1-3 alkyl, 1-3 alkoxy, 1-3 amino, 1-3 alkylamino, 1-3 dialklyamino, 1-3 nitrile, or 1-3 haloalkyl;

Y is a monocyclic aryl or monocyclic heteroaryl; each of which is optionally substituted with 1-4 $R^{10}$;

each $R^6$ and $R^{6'}$ are independently halo, alkyl, alkenyl, alkynyl, cyclyl, heterocyclyl, aryl, heteroaryl, alkoxy, haloalkyl, haloalkyloxy, haloalkylthio, acetyl, cyano, nitro, hydroxy, oxo, C(O)OR$^2$, OC(O)R$^2$, N(R$^3$)$_2$, C(O)N(R$^3$)$_2$, NR$^3$C(O)R$^2$, or SR$^2$;

$R^{7a}$ and $R^{7b}$ are each independently hydrogen, alkyl, alkenyl, haloalkyl, cyclyl, cyclylalkyl, or heterocyclyl; or one or both of $R^{7a}$ and $R^{7b}$ can independently be joined to one or both of $R^4$ and $R^5$ to form one or more bridges between the nitrogen to which the $R^4$ and $R^5$ are attached and $R^{7a}$ and $R^{7b}$, wherein each bridge contains 1 to 5 carbons; or one or both of $R^{7a}$ and $R^{7b}$ can independently be joined to one or both or $R^4$ and $R^5$ to form to form one or more heterocyclic rings including the nitrogen to which the $R^4$ and $R^5$ are attached, or one or both of $R^{7a}$ and $R^{7b}$ can independently be joined with $R^8$ to form a ring; wherein each $R^{7a}$ and $R^{7b}$ can be independently optionally substituted with 1-5 halo, 1-3 hydroxy, 1-3 alkyl, 1-3 alkoxy, 1-3 amino, 1-3 alkylamino, 1-3 dialklyamino, 1-3 nitrile, or 1-3 haloalkyl;

$R^8$ is hydrogen or $C_1$-$C_6$ alkyl, or $R^8$ can be joined with $R^4$, $R^5$, $r^{7a}$ or $R^{7b}$ to form a ring;

$R^9$ is halo, alkyl, cyclyl, heterocyclyl, aryl, heteroaryl, alkoxy, haloalkyl, haloalkyloxy, haloalkylthio, acetyl, cyano, nitro, hydroxy, oxo, $C(O)OR^2$, $OC(O)R^2$, $N(R^2)_2$, $C(O)N(R^2)_2$, $NR^2C(O)R^2$, $SR^2$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, $-OR^{11}$, $-NR^{11}R^{11'}$, $-CF_3$, $-SOR^{12}$, $-SO_2R^{12}$, $-OC(O)R^{11}$, $-SO_2NR^{12}R^{12'}$, $-(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form $-(CH_2)_qX(CH_2)_s-$; wherein each $R^{12}$ and $R^{12'}$ may independently optionally be substituted with 1 to 3 substituents selected from the group consisting of halogen, $OR^{11}$, alkoxy, heterocycloalkyl, $-NR^{11}C(O)NR^{11}R^{11'}$, $-C(O)NR^{11}R^{11'}$, $-NR^{11}C(O)R^{11'}$, $-CN$, oxo, $-NR^{11}SO_2R^{11'}$, $-OC(O)R^{11}$, $-SO_2NR^{11}R^{11'}$, $-SOR^{13}$, $-S(O)_2R^{13}$, $-COOH$ and $-C(O)OR^{13}$; each $R^{13}$ is independently alkyl, aryl, arylalkyl, heteroaryl, or heteroarylalkyl, each of which may optionally be substituted with $-(CH_2)_wOH$;

each $R^{14}$ is independently alkoxy, alkoxycarbonyl, $-C(O)NR^{12}R^{12'}$, $-NR^{11}R^{11'}$, $-C(O)R^{12}$, $-NR^{11}C(O)NR^{11}R^{11'}$ or $-N$-heteroaryl;

each $R^{15}$ is independently $-(CH_{2p}N(R^{12})C(O)R^{12'}$, $-(CH_2)_pCN$, $-(CH_2)_p(N(R^{12})C(O)OR^{12'}$, $-(CH_2)_pN(R^{12})C(O)NR^{12}R^{12'}$, $-(CH_2)_pN(R^{12})SO_2R^{12'}$, $-(CH_2)_pSO_2NR^{12}R^{12'}$, $-(CH_2)_pC(O)NR^{12}R^{12'}$, $-(CH_2)_pC(O)OR^{12}$, $-(CH^2)_pOC(O)OR^{12}$, $-(CH_2)_pOC(O)R^{12}$, $-(CH_2)_p OC(O)NR^{12}R^{12'}$, $-(CH_{2p}N(R^{12})SO_2NR^{12}R^{12'}$, $-(CH_2)_pOR^{12}$, $-(CH_2)_pOC(O)N(R^{12})(CH_2)_mOH$, $-(CH_2)_pSOR^{12}$, $-(CH_2)_pSO_2R^{12}$, $-(CH_2)_pNR^{11}R^{11'}$ or $-(CH_2)_pOCH_2C(O)N(R^{12})(CH_2)_mOH$;

each $R^{16}$ is independently halo, alkyl, alkenyl, alkynyl, alkoxy, $-(CH_2)_pNR^{11}C(O)NR^{11}R^{11'}$, $-(CH_2)_pC(O)NR^{11}R^{11'}$, $-(CH_2)_pNR^{11}C(O)R^{11'}$, $-CN$, $-(CH_2)_pNR^{11}SO_2R^{11'}$, $-(CH_2)_pOC(O)R^{11}$, $-(CH_2)_pSO_2NR^{11}R^{11'}$, $-(CH_2)_pSOR^{13}$, $-(CH_2)_pCOOH$ or $-(CH_2)_pC(O)OR^{13}$;

X is $CR^{11}R^{11'}$, O, S, S(O), $S(O)_2$, or $NR^{11}$;

m is an integer between 1 and 6;

p is an integer from 0 to 5;

q and s are each independently an integer between 1 and 3; and w is an integer between 0 and 5.

In some embodiments, formula (I), comprises an enriched preparation of formula (I')

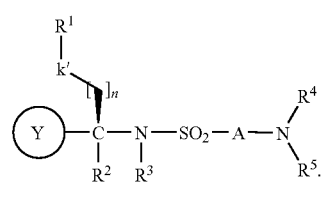

formula (I')

In some embodiments, formula (I), comprises an enriched preparation of formula (I")

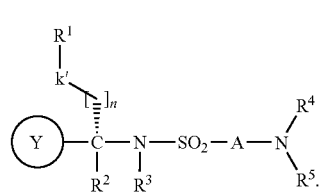

formula (I")

In some embodiments,
n is 1;
k' is a bond or O; and
$R^1$ is aryl, heteroaryl, arylalkyl, or heteroarylalkyl.
In some embodiments,
n is 1;
k' is O; and
$R^1$ is arylalkyl.
For example, $R^1$ can be phenylmethyl.
In some embodiments,
n is 2;
k' is a bond; and
$R^1$ is aryl.
In some embodiments,
n is 0 or 1;
k' is a bond; and
$R^1$ is alkyl, for example unsubstituted or substituted with one $R^6$. For example, $R^1$ can be a branched alkyl such as one of the following.

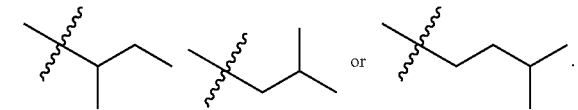

In some embodiments, $R^2$ is hydrogen or $C_1$-$C_3$ alkyl.
In some embodiments n is 0 and k' is a bond. Exemplary $R^1$ moieties include methyl, and ethyl. Preferred $R^1$ moieties include methyl. In some embodiments $R^1$ is unsubstituted methyl or methyl or ethyl substituted with $C(O)N(R^3)_2$.
In some embodiments n is 0 and k' is a bond, and $R^1$ and $R^2$ are both methyl.
In some embodiments,
n is 0;
k' is a bond; and
$R^1$ is hydrogen.
In some embodiments $R^3$ is hydrogen.
In some embodiments, $R^1$ and $R^3$ together from a heterocyclic ring such as a pyrrolidine or an azetidine ring. The heterocyclic ring can be unsubstituted or substituted, for example, with 1-2 $R^6$.
In some embodiments, $R^1$ and $R^2$ together form a ring.

In some embodiments, A is

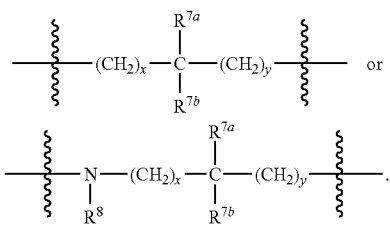 or

For example, A can be

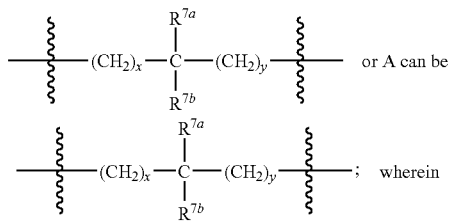 or A can be

; wherein $R^{7a}$ and $R^{7b}$ are H;
x is 1; and
y is 0 or 1.

In some embodiments,
A is $CH_2CH_2$ or $CH_2CH_2CH_2$; and each $R^4$ and $R^5$ is independently alkyl, or $R^4$ and $R^5$, when taken together, form a heterocyclic ring. In some embodiments, $R^{7a}$ and $R^{7b}$ can each be H.

In some embodiments, at least one of $R^{7a}$ or $R^{7b}$ is taken together with at least one or $R^4$ or $R^5$ to form a heterocyclic ring including the nitrogen to which the $R^4$ and $R^5$ are attached.

In some embodiments,
$R^{7a}$ and $R^{7b}$ are each independently alkyl;
$R^4$ and $R^5$ are each independently hydrogen or alkyl; and
x and y are each independently 0 or 1;

In some embodiments,

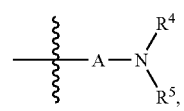

taken together is

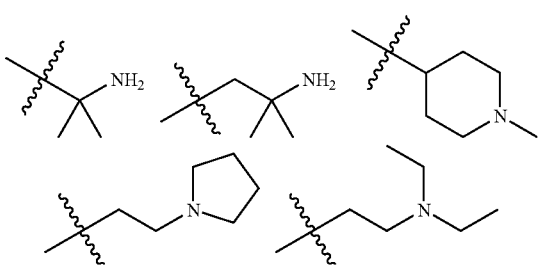

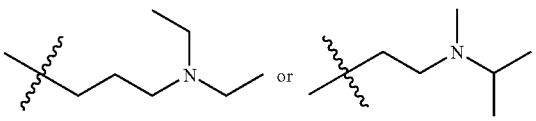

In some embodiments,

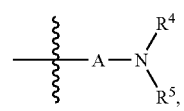

taken together is

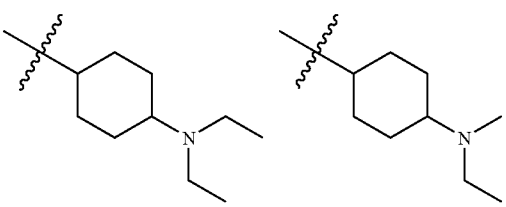

In some embodiments,

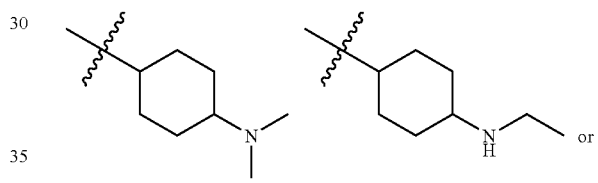

taken together is

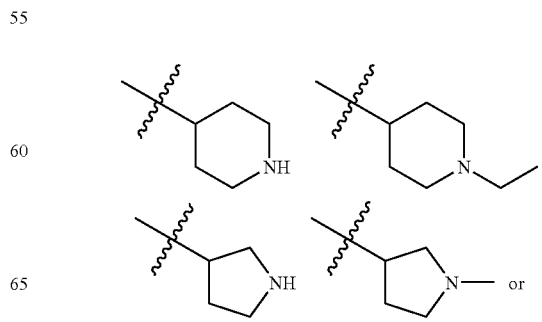

-continued

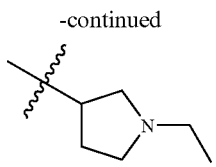

In some embodiments,

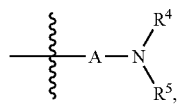

taken together is

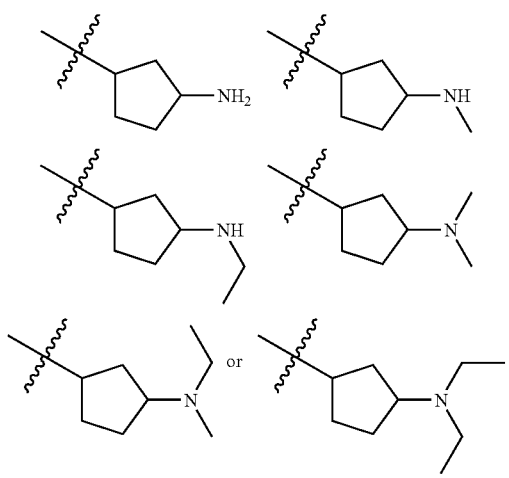

In some embodiments,

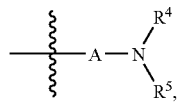

taken together is

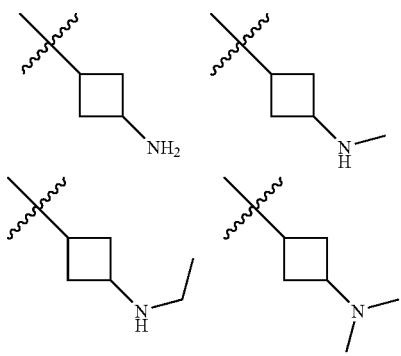

-continued

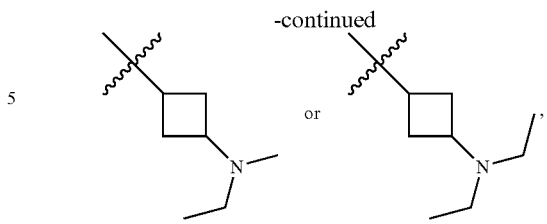

In some embodiments, Y is a monocyclic heteroaromatic moiety, for example a nitrogen containing heteraromatic moiety such as a nitrogen containing five membered heteroaromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one $R^{10}$. $R^{10}$ can be positioned, for example, 1,3 relative to the point of attachment of Y to the adjacent chain carbon or 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$]. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroarylalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In another aspect, the invention features a compound of formula (II),

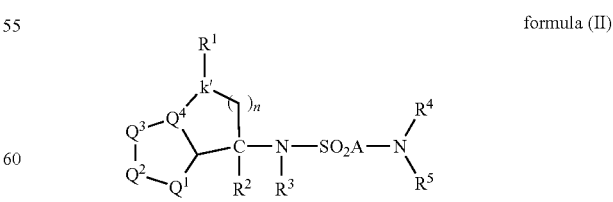

formula (II)

wherein, $Q^1$, $Q^2$, $Q^3$ and $Q^4$ together with the carbon to which they are attached form a heteroaryl moiety, and each $Q^1$, $Q^2$, $Q^3$ and $Q^4$ is independently S, O, N, $CR^2$, $CR^{10}$, $NR^2$, or $NR^{10}$.

In some embodiments, the compound of formula (II), comprises an enriched preparation of formula (II')

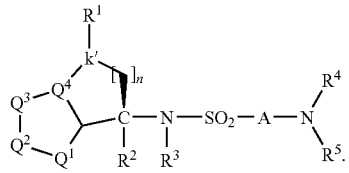

formula (II')

In some embodiments, the compound of formula (II), comprises an enriched preparation of formula (II")

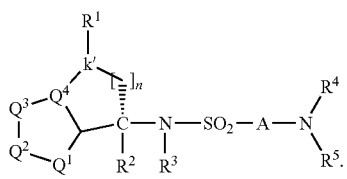

formula (II")

In some embodiments, $Q^1$ and $Q^4$ are each independently S, O, N, or $NR^{10}$.

In some embodiments, $Q^1$ and $Q^3$ are each independently S, O, N, or $NR^{10}$.

In some embodiments, $Q^2$ is $CR^2$ or $CR^{10}$.

In some embodiments, $Q^2$ is S, O, N, or $NR^{10}$.

In some embodiments, at least one of $Q^2$ or $Q^3$ is $CR^2$ or $CR^{10}$.

In some embodiments, at least two of $Q^1$, $Q^2$, $Q^3$, or $Q^4$ is S, O, N, or $NR^{10}$.

In some embodiments, $Q^1$, $Q^2$, and $Q^3$ are each independently S, O, N, or $NR^{10}$.

In some embodiments, $Q^1$ is $NR^{10}$.

In some embodiments, one of $Q^2$, $Q^3$, or $Q^4$ is $CR^2$.

In some embodiments, $Q^2$ is $CR^{10}$.

In some embodiments, $Q^3$ is $CR^2$.

In some embodiments, $Q^1$, $Q^2$, $Q^3$ and $Q^4$ together form

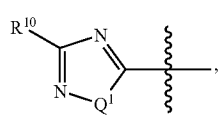

In some embodiments, $Q^1$ is $NR^2$.

In some embodiments, $Q^1$, $Q^2$, $Q^3$ and $Q^4$ together form

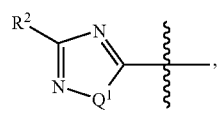

In some embodiments, $Q^1$ is $NR^{10}$.

In another aspect, the invention features a compound of formula (III),

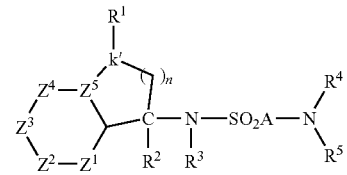

wherein,
$Z^1$, $Z^2$, $Z^3$, $Z^4$, and $Z^5$ together form an aryl or heteroaryl moiety, and each $Z^1$, $Z^2$, $Z^3$, $Z^4$, and $Z^5$ is independently N, $CR^{10}$, or $CR^2$.

In some embodiments, the compound of formula (III), comprises an enriched preparation of formula (III')

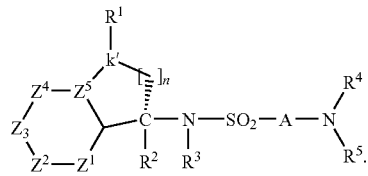

formula (III')

In some embodiments, the compound of formula (III), comprises an enriched preparation of formula (III')

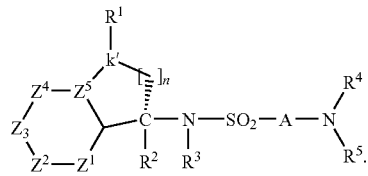

formula (III')

In some embodiments, one of $Z^1$, $Z^2$, $Z^3$, $Z^4$, and $Z^5$ is N.
In some embodiments, two of $Z^1$, $Z^2$, $Z^3$, $Z^4$, and $Z^5$ are N.
In some embodiments, three of $Z^1$, $Z^2$, $Z^3$, $Z^4$, and $Z^5$ is N.
In some embodiments, two of $Z^1$ and $Z^2$ are N.
In some embodiments, two of $Z^1$ and $Z^3$ are N.
In some embodiments, two of $Z^1$ and $Z^4$ are N.
In some embodiments, two of $Z^1$, $Z^3$, and $Z^5$ are N.

In some embodiments, the compound is a compound of formula (I), wherein Y is substituted with a single substituent $R^{10}$. For example, $R^{10}$ can be aryl or heteroaryl, optionally substituted with up to three independent $R^{16}$.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroaryalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is $R^{15}$.

In some embodiments, Y is substituted with a second $R^{10}$, for example an alkyl, halo or alkoxy.

In some embodiments, $R^1$ is aryl, heteroaryl, arylalkyl, or heteroarylalkyl;

k' is a bond or O;

n is 1 or 2;

$R^2$ and $R^3$ are both hydrogen;

A is

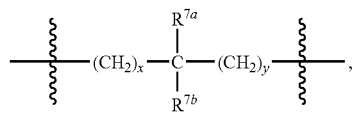

x and y are each independently 0-6;

$R^4$ and $R^5$ are each independently hydrogen or alkyl;

Y is a monocyclic aryl or monocyclic heteroaryl; each of which is optionally substituted with 1-4 $R^{10}$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —$OR^{11}$, —$NR^{11}R^{11'}$, —$CF_3$, —$SOR^{12}$, —$SO_2R^{12}$, —$OC(O)R^{11}$, —$SO_2NR^{12}R^{12'}$, —$(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form —$(CH_2)_qX(CH_2)_s$—; wherein each $R^{12}$ and $r^{12'}$ may independently optionally be substituted with 1 to 3 substituents selected from the group consisting of halogen, $OR^{11}$, alkoxy, heterocycloalkyl, —$NR^{11}C(O)NR^{11}R^{11'}$, —$C(O)NR^{11}R^{11'}$, —$NR^{11}C(O)R^{11'}$, —CN, oxo, —$NR^{11}SO_2R^{11'}$, —$OC(O)R^{11}$, —$SO_2NR^{11}R^{11'}$, —$SOR^{13}$, —$S(O)_2R^{13}$, —COOH and —$C(O)OR^{13}$; each $R^{13}$ is independently alkyl, aryl, arylalkyl, heteroaryl, or heteroarylalkyl, each of which may optionally be substituted with —$(CH_2)_wOH$;

each $R^{14}$ is independently alkoxy, alkoxycarbonyl, —$C(O)NR^{12}R^{12'}$, —$NR^{11}R^{11'}$, —$C(O)R^{12}$, —$NR^{11}C(O)NR^{11}R^{11'}$ or —N-heteroaryl;

each $R^{15}$ is independently —$(CH_2)_pN(R^{12})C(O)R^{12'}$, —$(CH_2)_pCN$, —$(CH_2)_pN(R^{12})C(O)OR^{12'}$, —$(CH_2)_pN(R^{12})C(O)NR^{12}R^{12'}$, —$(CH_2)_pN(R^{12})SO_2R^{12'}$, —$(CH_2)_pSO_2NR^{12}R^{12'}$, —$(CH_2)_pC(O)NR^{12}R^{12'}$, —$(CH_2)_pC(O)OR^{12}$, —$(CH^2)_pOC(O)OR^{12}$, —$(CH_2)_pOC(O)R^{12}$, —$(CH_2)_pOC(O)NR^{12}R^{12'}$, —$(CH_2)_pN(R^{12})SO_2NR^{12}R^{12'}$, —$(CH_2)_pOR^{12}$, —$(CH_2)_pOC(O)N(R^{12})(CH_2)_mOH$, —$(CH_2)_pSOR^{12}$, —$(CH_2)_pSO_2R^{12}$, —$(CH_2)_pNR^{11}R^{11'}$ or —$(CH_2)_pOCH_2C(O)N(R^{12})(CH_2)_mOH$;

each $R^{16}$ is independently halo, alkyl, alkenyl, alkynyl, alkoxy, —$(CH_2)_pNR^{11}C(O)NR^{11}R^{11'}$, —$(CH_2)_pC(O)NR^{11}R^{11'}$, —$(CH_2)_pNR^{11}C(O)R^{11'}$, —CN, —$(CH_2)_pNR^{11}SO_2R^{11'}$, —$(CH_2)_pOC(O)R^{11}$, —$(CH_2)_pSO_2NR^{11}R^{11'}$, —$(CH_2)_pSOR^{13}$, —$(CH_2)_pCOOH$ or —$(CH_2)_pC(O)OR^{13}$;

X is $CR^{11}R^{11'}$, O, S, $S(O)_2$, or $NR^{11}$;

m is an integer between 1 and 6;

p is an integer from 0 to 5;

q and s are each independently an integer between 1 and 3; and w is an integer between 0 and 5.

For example, in some embodiments, n is 1; k' is a bond or O; and $R^1$ is aryl, heteroaryl, arylalkyl, or heteroarylalkyl. In some embodiments, n is 1; k' is O; and $R^1$ is arylalkyl, for example phenylmethyl. In some embodiments, n is 2; k' is a bond; and $r^1$ is aryl.

For example, in some embodiments, $R^{7a}$ and $R^{7b}$ are H; x is 1; and y is 0 or 1. In some embodiments, A is $CH_2CH_2$ or $CH_2CH_2CH_2$.

In some embodiments, each $R^4$ and $R^5$ is independently alkyl, for example, methyl or ethyl, preferably ethyl.

In some embodiments, Y is a monocyclic heteroaromatic moiety, for example a nitrogen containing heteraromatic moiety such as nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one $R^{10}$. $R^{10}$ can positioned, for example, 1,3 relative to the point of attachment of Y to the adjacent chain carbon or 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroarylalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In some embodiments, Y is

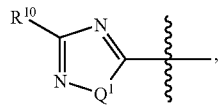

wherein Q1 is O or $NR^2$, preferably O or NH. In some embodiments, $R^{10}$ is aryl, arylalkyl, heteroaryl, or heteroarylalkyl, for example optionally substituted with one or more $R^{16}$. In some embodiments, $R^{10}$ is substituted with one $R^{16}$, such as halo (e.g., fluoro or chloro) or alkoxy.

In some embodiments, the compounds has a formula (Ia)

formula (Ia)

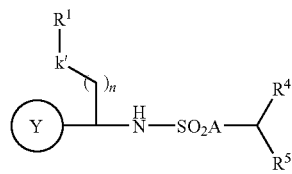

In some embodiments, $R^1$ is aryl, heteroaryl, arylalkyl, or heteroarylalkyl;
k' is a bond or O;
n is 1 or 2;
A is $CH_2$, $CH_2CH_2$, or $CH_2CH_2CH_2$;
$R^4$ and $R^5$ are each independently hydrogen or alkyl;
Y is a monocyclic aryl or monocyclic heteroaryl; each of which is optionally substituted with 1-4 $R^{10}$;
each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, $-OR^{11}$, $-NR^{11}R^{11'}$, $-CF_3$, $-SOR^{12}$, $-SO_2R^{12}$, $-OC(O)R^{11}$, $-SO_2NR^{12}R^{12'}$, $-(CH_2)_mR^{14}$ or $R^{15}$; each of which is optionally independently substituted with 1-3 $R^{16}$;
$R^{11}$ and $R^{11'}$ are each independently hydrogen, alkyl, alkenyl, alkynyl, cyclyl, heterocyclyl, aryl or heteroaryl;
$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form $-(CH_2)_qX(CH_2)_s-$; wherein each $R^{12}$ and $R^{12'}$ may independently optionally be substituted with 1 to 3 substituents selected from the group consisting of halogen, $OR^{11}$, alkoxy, heterocycloalkyl, $-NR^{11}C(O)NR^{11}R^{11'}$, $-C(O)NR^{11}R^{11'}$, $-NR^{11}C(O)R^{11'}$, $-CN$, oxo, $-NR^{11}SO_2R^{11'}$, $-OC(O)R^{11}$, $-SO_2NR^{11}R^{11'}$, $-SOR^{13}$, $-S(O)_2R^{13}$, $-COOH$ and $-C(O)OR^{13}$; each $R^{13}$ is independently alkyl, aryl, arylalkyl, heteroaryl, or heteroarylalkyl, each of which may optionally be substituted with $-(CH_2)_wOH$;
each $R^{14}$ is independently alkoxy, alkoxycarbonyl, $-C(O)NR^{12}R^{12'}$, $-NR^{11}R^{11'}$, $-C(O)R^{12}$, $-NR^{11}C(O)NR^{11}R^{11'}$ or $-N$-heteroaryl;
each $R^{15}$ is independently $-(CH_2)_pN(R^{12})C(O)R^{12'}$, $-(CH_2)_pCN$, $-(CH_2)_pN(R^{12})C(O)OR^{12'}$, $-(CH_2)_pN(R^{12})C(O)NR^{12}R^{12'}$, $-(CH_2)_pN(R^{12})SO_2R^{12'}$, $-(CH_2)_pSO_2NR^{12}R^{12'}$, $-(CH_2)_pC(O)NR^{12}R^{12'}$, $-(CH_2)_pC(O)OR^{12}$, $-(CH^2)_pOC(O)OR^{12}$, $-(CH_2)_pOC(O)R^{12}$, $-(CH_2)_p OC(O)NR^{12}R^{12'}$, $-(CH_2)_pN(R^{12})SO_2NR^{12}R^{12'}$, $-(CH_2)_pOR^{12}$, $-(CH_2)_pOC(O)N(R^{12})(CH_2)_mOH$, $-(CH_2)_pSOR^{12}$, $-(CH_2)_pSO_2R^{12}$, $-(CH_2)_pNR^{11}R^{11}$ or $-(CH_2)_pOCH_2C(O)N(R^{12})(CH_2)_mOH$;

each $R^{16}$ is independently halo, alkyl, alkenyl, alkynyl, alkoxy, $-(CH_2)_pNR^{11}C(O)NR^{11}R^{11'}$, $-(CH_2)_pC(O)NR^{11}R^{11'}$, $-(CH_2)_pNR^{11}C(O)R^{11'}$, $-CN$, $-(CH_2)_pNR^{11}SO_2R^{11'}$, $-(CH_2)_pOC(O)R^{11}$, $-(CH_2)_pSO_2NR^{11}R^{11'}$, $-(CH_2)_pSOR^{13}$, $-(CH_2)_pCOOH$ or $-(CH_2)_pC(O)OR^{13}$;

X is $CR^{11}R^{11'}$, O, S, $S(O)_2$, OR $NR^{11}$;

m is an integer between 1 and 6;

p is an integer from 0 to 5;

q and s are each independently an integer between 1 and 3; and w is an integer between 0 and 5.

For example in some embodiments, n is 1; k' is a bond or O; and $R^1$ is aryl, heteroaryl, arylalkyl, or heteroarylalkyl. In some embodiments, n is 1; k' is O; and $R^1$ is arylalkyl, for example phenylmethyl. In some embodiments, n is 2; k' is a bond; and $R^1$ is aryl.

In some embodiments, A is $CH_2CH_2$ or $CH_2CH_2CH_2$, preferably $CH_2CH_2CH_2$.

In some embodiments, each $R^4$ and $R^5$ is independently alkyl, for example, methyl or ethyl, preferably ethyl.

In some embodiments, Y is a monocyclic heteroaromatic moiety, for example a nitrogen containing heteraromatic moiety such as a nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one $R^{10}$. $R^{10}$ can be positioned, for example, 1,3 relative to the point of attachment of Y to the adjacent chain carbon or 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroarylalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In some embodiments, Y is

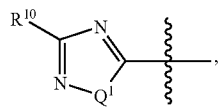

wherein Q1 is O or NR$^2$, preferably O or NH. In some embodiments, R$^{10}$ is aryl, arylalkyl, heteroaryl, or heteroarylalkyl, for example optionally substituted with one or more R$^{16}$. In some embodiments, R$^{10}$ is substituted with one R$^{16}$, such as halo (e.g., fluoro or chloro) or alkoxy. In some embodiments, R$^1$ is hydrogen or alkyl, for example unsubstituted or substituted with one R$^6$;

n is 0 or 1;

k' is a bond; and

R$^2$ and R$^3$ each independently hydrogen or C$_1$-C$_6$ alkyl;

A is

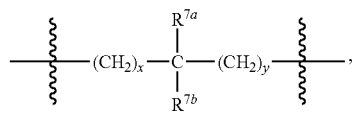

x and y are each independently 0-6;

R$^4$ and R$^5$ are each independently hydrogen or alkyl;

Y is a monocyclic aryl or monocyclic heteroaryl; each of which is optionally substituted with 1-4 R$^{10}$;

each R$^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —OR$^{11}$, —NR$^{11}$R$^{11'}$, —CF$_3$—SOR$^{12}$, —SO$_2$R$^{12}$, —OC(O)R$^{11}$, —SO$_2$NR$^{12}$R$^{12'}$, —(CH$_2$)$_m$R$^{14}$ or R$^{15}$; each of which is optionally independently substituted with 1-3 R$^{16}$;

R$^{11}$ and R$^{11'}$ are each independently hydrogen, alkyl, alkenyl, alkynyl, cyclyl, heterocyclyl, aryl or heteroaryl;

R$^{12}$ and R$^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or R$^{12}$ and R$^{12'}$ taken together can be cyclized to form —(CH$_2$)$_q$X(CH$_2$)$_s$—; wherein each R$^{12}$ and R$^{12'}$ may independently optionally be substituted with 1 to 3 substituents selected from the group consisting of halogen, OR$^{11}$, alkoxy, heterocycloalkyl, —NR$^{11}$C(O)NR$^{11}$R$^{11'}$, —C(O)NR$^{11}$R$^{11'}$, —NR$^{11}$C(O)R$^{11'}$, —CN, oxo, —NR$^{11}$SO$_2$R$^{11'}$, —OC(O)R$^{11}$, —SO$_2$NR$^{11}$R$^{11'}$, —SOR$^{13}$, —S(O)$_2$R$^{13}$, —COOH and —C(O)OR$^{13}$;

each R$^{13}$ is independently alkyl, aryl, arylalkyl, heteroaryl, or heteroarylalkyl, each of which may optionally be substituted with —(CH$_2$)$_w$OH;

each R$^{14}$ is independently alkoxy, alkoxycarbonyl, —C(O)NR$^{12}$R$^{12'}$, —NR$^{11}$R$^{11'}$, —C(O)R$^{12}$, —NR$^{11}$C(O)NR$^{11}$R$^{11'}$ or —N-heteroaryl;

each R$^{15}$ is independently —(CH$_2$)$_p$N(R$^{12}$)C(O)R$^{12'}$, —(CH$_2$)$_p$CN, —(CH$_2$)$_p$N(R$^{12}$)C(O)OR$^{12'}$, —(CH$_2$)$_p$N(R$^{12}$)C(O)NR$^{12}$R$^{12'}$, —(CH$_2$)$_p$N(R$^{12}$)SO$_2$R$^{12'}$, —(CH$_2$)$_p$SO$_2$NR$^{12}$R$^{12'}$, —(CH$_2$)$_p$C(O)NR$^{12}$R$^{12'}$, —(CH$_2$)$_p$C(O)OR$^{12}$, —(CH$_2$)$_p$OC(O)R$^{12}$, —(CH$_2$)$_p$OC(O)NR$^{12}$R$^{12'}$, —(CH$_2$)$_p$N(R$^{12}$)SO$_2$NR$^{12}$R$^{12'}$, —(CH$_2$)$_p$OR$^{12}$, —(CH$_2$)$_p$OC(O)N(R$^{12}$)(CH$_2$)$_m$OH, —(CH$_2$)$_p$SOR$^{12}$, —(CH$_2$)$_p$SO$_2$R$^{12}$, —(CH$_2$)$_p$NR$^{11}$R$^{11}$ or —(CH$_2$)$_p$OCH$_2$C(O)N(R$^{12}$)(CH$_2$)$_m$OH;

each r$^{16}$ is independently halo, alkyl, alkenyl, alkynyl, alkoxy, —(CH$_2$)$_p$NR$^{11}$C(O)NR$^{11}$R$^{11'}$, —(CH$_2$)$_p$C(O)NR$^{11}$R$^{11'}$, —(CH$_2$)$_p$NR$^{11}$C(O)R$^{11'}$, —CN, —(CH$_2$)$_p$NR$^{11}$SO$_2$R$^{11'}$, —(CH$_2$)$_p$OC(O)R$^{11}$, —(CH$_2$)$_p$SO$_2$NR$^{11}$R$^{11'}$, —(CH$_2$)$_p$SOR$^{13}$, —(CH$_2$)$_p$COOH or —(CH$_2$)$_p$C(O)OR$^{13}$;

X is CR$^{11}$R$^{11'}$, O, S, S(O), S(O)$_2$, or NR$^{11}$;

m is an integer between 1 and 6;

p is an integer from 0 to 5;

q and s are each independently an integer between 1 and 3; and w is an integer between 0 and 5.

In some embodiments, n is 0 or 1;

k' is a bond; and

R$^1$ is alkyl, for example unsubstituted or substituted with one R$^6$.

In some embodiments n is 0 and k' is a bond. Exemplary R$^1$ moieties include methyl, and ethyl. Preferred R$^1$ moieties include methyl. In some embodiments R$^1$ is unsubstituted methyl or methyl or ethyl substituted with C(O)N(R$^3$)$_2$.

In some embodiments, n is 0 or 1;

k' is a bond; and

R$^1$ is alkyl, for example unsubstituted or substituted with one R$^6$. For example, R$^1$ can be a branched alkyl such as one of the following

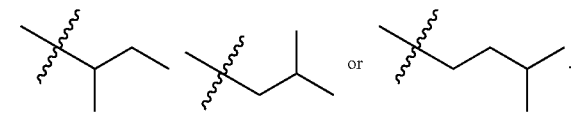

In some embodiments n is 0 and k' is a bond, and R$^1$ and R$^3$ are both methyl.

In some embodiments, n is 0;

k' is a bond; and

R$^1$ is hydrogen.

In some embodiments, A is CH$_2$CH$_2$ or CH$_2$CH$_2$CH$_2$, preferably CH$_2$CH$_2$CH$_2$.

In some embodiments, each R$^4$ and R$^5$ is independently alkyl, for example methyl or ethyl, preferably ethyl.

In some embodiments, Y is a monocyclic heteroaromatic moiety, for example a nitrogen containing heteraromatic moiety such as a nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one R$^{10}$. R$^{10}$ can be positioned, for example, 1,3 relative to the point of attachment of Y to the adjacent chain carbon or 1,2 relative to the point of attachment of Y to the adjacent chain carbon.

In some embodiments, R$^{10}$ is aryl or heteroaryl, for example a monocyclic aryl or monocyclic heteroaryl such as phenyl, pyridyl, oxazolyl, thiazolyl, or thiophenyl. In some embodiments, R$^{10}$ is substituted with 1-3 R$^{16}$. In some embodiments, R$^{16}$ is halo, alkyl, or alkoxy, for example chloro, fluoro, methyl, cyano, or methoxy.

In some embodiments, R$^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroaryalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In some embodiments, Y is

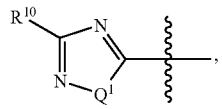

wherein Q1 is O or $NR^2$, preferably O or NH. In some embodiments, $R^{10}$ is aryl, arylalkyl, heteroaryl, or heteroarylalkyl, for example optionally substituted with one or more $R^{16}$. In some embodiments, $R^{10}$ is substituted with one $R^{16}$, such as halo (e.g., fluoro or chloro) or alkoxy.

In some embodiments, the compounds has a formula (Ib)

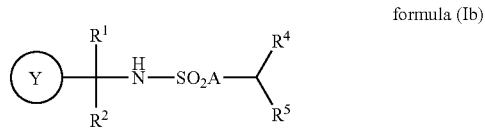

formula (Ib)

In some embodiments, $R^1$ is hydrogen or alkyl;

A is $CH_2$, $CH_2CH_2$, or $CH_2CH_2CH_2$;

$R^2$ is hydrogen or $C_1$-$C_3$ alkyl;

$R^4$ and $R^5$ are each independently hydrogen or alkyl;

Y is a monocyclic aryl or monocyclic heteroaryl; each of which is optionally substituted with 1-4 $R^{10}$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —$OR^{11}$, —$NR^{11}R^{11'}$, —$CF_3$, —$SOR^{12}$, —$SO_2R^{12}$, —$OC(O)R^{11}$, —$SO_2NR^{12}R^{12'}$, —$(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form —$(CH_2)_qX(CH_2)_s$—; wherein each $R^{12}$ and $R^{12'}$ may independently optionally be substituted with 1 to 3 substituents selected from the group consisting of halogen, $OR^{11}$, alkoxy, heterocycloalkyl, —$NR^{11}C(O)NR^{11}R^{11'}$, —$C(O)NR^{11}R^{11'}$, —$NR^{11}C(O)R^{11'}$, —CN, oxo, —$NR^{11}SO_2R^{11'}$, —$OC(O)R^{11}$, —$SO_2NR^{11}R^{11'}$, —$SOR^{13}$, —$S(O)_2R^{13}$, —COOH and —$C(O)OR^{13}$; each $R^{13}$ is independently alkyl, aryl, arylalkyl, heteroaryl, or heteroarylalkyl, each of which may optionally be substituted with —$(CH_2)_wOH$;

each $R^{14}$ is independently alkoxy, alkoxycarbonyl, —$C(O)NR^{12}R^{12'}$, —$NR^{11}R^{11'}$, —$C(O)R^{12}$, —$NR^{11}C(O)NR^{11}R^{11'}$, or —N-heteroaryl;

each $R^{15}$ is independently —$(CH_2)_pN(R^{12})C(O)R^{12'}$, —$(CH_2)_pCN$, —$(CH_2)_pN(R^{12})C(O)OR^{12'}$, —$(CH_2)_pN(R^{12})C(O)NR^{12}R^{12'}$, —$(CH_2)_pN(R^{12})SO_2R^{12'}$, —$(CH_2)_pSO_2NR^{12}R^{12'}$, —$(CH_2)_pC(O)NR^{12}R^{12'}$, —$(CH_2)_pC(O)OR^{12}$, —$(CH^2)_pOC(O)OR^{12}$, —$(CH_2)_pOC(O)R^{12}$, —$(CH_2)_p OC(O)NR^{12}R^{12'}$, —$(CH_2)_pN(R^{12})SO_2NR^{12}R^{12'}$, —$(CH_2)_pOR^{12}$, —$(CH_2)_pOC(O)N(R^{12})(CH_2)_mOH$, —$(CH_2)_pSOR^{12}$, —$(CH_2)_pSO_2R^{12}$, —$(CH_2)_pNR^{11}R^{11'}$ or —$(CH_2)_pOCH_2C(O)N(R^{12})(CH_2)_mOH$;

each $R^{16}$ is independently halo, alkyl, alkenyl, alkynyl, alkoxy, —$(CH_2)_pNR^{11}C(O)NR^{11}R^{11'}$, —$(CH_2)_pC(O)NR^{11}R^{11'}$, —$(CH_2)_pNR^{11}C(O)R^{11'}$, —CN, —$(CH_2)_pNR^{11}SO_2R^{11'}$, —$(CH_2)_pOC(O)R^{11}$, —$(CH_2)_pSO_2NR^{11}R^{11'}$, —$(CH_2)_pSOR^{13}$, —$(CH_2)_pCOOH$ or —$(CH_2)_p(C(O)OR^{13}$;

X is $CR^{11}R^{11'}$, O, S, S(O), $S(O)_2$, or $NR^{11}$;

m is an integer between 1 and 6;

p is an integer from 0 to 5;

q and s are each independently an integer between 1 and 3; and w is an integer between 0 and 5.

In some embodiments, A is $CH_2CH_2$ or $CH_2CH_2CH_2$, preferably $CH_2CH_2CH_2$.

In some embodiments, each $R^4$ and $R^5$ is independently alkyl, for example methyl or ethyl, preferably ethyl.

In some embodiments, Y is a monocyclic heteroaromatic moiety, for example a nitrogen containing heteraromatic moiety such as a nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one $R^{10}$. $R^{10}$ can be positioned, for example, 1,3 relative to the point of attachment of Y to the adjacent chain carbon or 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroaryalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$.

In some embodiments, $R^{16}$ is halo, alkyl, or alkoxy, for example chloro, fluoro, methyl, cyano, or methoxy.

In some embodiments Y is oxadiazole or triazole.

In some embodiments, Y is

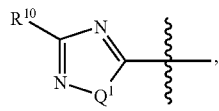

wherein Q1 is O or $NR^2$, preferably O or NH. In some embodiments, $R^{10}$ is aryl, arylalkyl, heteroaryl, or heteroarylalkyl, for example optionally substituted with one or more $R^{16}$. In some embodiments, $R^{10}$ is substituted with one $R^{16}$, such as halo (e.g., fluoro or chloro) or alkoxy.

In some embodiments, $R^1$ and $R^3$ together form a heterocyclic ring such as a pyrrolidine or an azetidine ring (The heterocyclic ring can be unsubstituted or substituted, for example, with 1-2 $R^6$.);

n is 0 or 1;

k' is a bond;

$R^2$ hydrogen or $C_1$-$C_6$ alkyl, preferably hydrogen;

A is

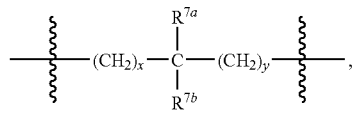

x and y are each independently 0-6;

$R^4$ and $R^5$ are each independently hydrogen or alkyl;

Y is a monocyclic aryl or monocyclic heteroaryl; each of which is optionally substituted with 1-4 $R^{10}$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —$OR^{11}$, —$NR^{11}R^{11'}$, —$CF_3$, —$SOR^{12}$, —$SO_2R^{12}$, —$OC(O)R^{11}$, —$SO_2NR^{12}R^{12'}$, —$(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form —$(CH_2)_qX(CH_2)_s$—; wherein each $R^{12}$ and $R^{12'}$ may independently optionally be substituted with 1 to 3 substituents selected from the group consisting of halogen, $OR^{11}$, alkoxy, heterocycloalkyl, —$NR^{11}C(O)NR^{11}R^{11'}$, —$C(O)NR^{11}R^{11'}$, —$NR^{11}C(O)R^{11'}$, —CN, oxo, —$NR^{11}SO_2R^{11'}$; —$OC(O)R^{11}$, —$SO_2NR^{11}R^{11'}$, —$SOR^{13}$, —$S(O)_2R^{13}$, —COOH and —$C(O)OR^{13}$; each $R^{13}$ is independently alkyl, aryl, arylalkyl, heteroaryl, or heteroarylalkyl, each of which may optionally be substituted with —$(CH_2)_wOH$;

each $R^{14}$ is independently alkoxy, alkoxycarbonyl, —$C(O)NR^{12}R^{12'}$, —$NR^{11}R^{11'}$, —$C(O)R^{12}$, —$NR^{11}C(O)NR^{11}R^{11'}$ or —N-heteroaryl;

each $R^{15}$ is independently —$(CH_2)_pN(R^{12})C(O)R^{12'}$, —$(CH_2)_pCN$, —$(CH_2)_pN(R^{12})C(O)OR^{12'}$, —$(CH_2)_pN(R^{12})C(O)NR^{12}R^{12'}$, —$(CH_2)_pN(R^{12})SO_2R^{12'}$, —$(CH_2)_pSO_2NR^{12}R^{12'}$, —$(CH_2)_pC(O)NR^{12}R^{12'}$, —$(CH_2)_pC(O)$ $OR^{12}$, —$(CH^2)_pOC(O)OR^{12}$, —$(CH_2)_pOC(O)R^{12}$, —$(CH_2)_p OC(O)NR^{12}R^{12'}$, —$(CH_2)_pN(R^{12})SO_2NR^{12}R^{12'}$, —$(CH_2)_pOR^{12}$, —$(CH_2)_pOC(O)N(R^{12})(CH_2)_mOH$, —$(CH_2)_pSOR^{12}$, —$(CH_2)_pSO_2R^{12}$, —$(CH_2)_pNR^{11}R^{11'}$ or —$(CH_2)_pOCH_2C(O)N(R^{12})(CH_2)_mOH$;

each $R^{16}$ is independently halo, alkyl, alkenyl, alkynyl, alkoxy, —$(CH_2)_pNR^{11}C(O)NR^{11}R^{11'}$, —$(CH_2)_pC(O)NR^{11}R^{11'}$, —$(CH_2)_pNR^{11}C(O)R^{11'}$, —CN, —$(CH_2)_pNR^{11}SO_2R^{11'}$, —$(CH_2)_pOC(O)R^{11}$, —$(CH_2)_p SO_2NR^{11}R^{11'}$, —$(CH_2)_pSOR^{13}$, —$(CH_2)_pCOOH$ or —$(CH_2)_pC(O)OR^{13}$;

X is $CR^{11}R^{11'}$, O, S, S(O), S(O)$_2$, or $NR^{11}$;

m is an integer between 1 and 6;

p is an integer from 0 to 5;

q and s are each independently an integer between 1 and 3; and w is an integer between 0 and 5;

In some embodiments, A is $CH_2CH_2$ or $CH_2CH_2CH_2$, preferably $CH_2CH_2CH_2$.

In some embodiments, each $R^4$ and $R^5$ is independently alkyl, for example, methyl or ethyl, preferably ethyl.

In some embodiments, Y is monocyclic heteroaromatic moiety, for example a nitrogen containing heteraromatic moiety such as a nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroaryalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In some embodiments, Y is

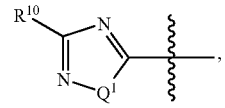

wherein Q1 is O or $NR^2$, preferably O or NH. In some embodiments, $R^{10}$ is aryl, arylalkyl, heteroaryl, or heteroarylalkyl, for example optionally substituted with one or more $R^{16}$. In some embodiments, $R^{10}$ is substituted with one $R^{16}$, such as halo (e.g., fluoro or chloro) or alkoxy. In some embodiments, the compounds has a formula (Ic)

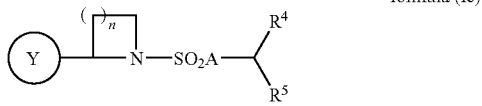

formula (Ic)

n is 0, 1, 2, 3, or 4; preferably 1 or 2;

A is $CH_2$, $CH_2CH_2$, or $CH_2CH_2CH_2$;

$R^4$ and $r^5$ are each independently hydrogen or alkyl;

Y is a monocyclic aryl or monocyclic heteroaryl; each of which is optionally substituted with 1-4 $R^{10}$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, $-OR^{11}$, $-NR^{11}R^{11'}$, $-CF_3$, $-SOR^{12}$, $-SO_2R^{12}$, $-OC(O)R^{11}$, $-SO_2NR^{12}R^{12'}$, $-(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form $-(CH_2)_qX(CH_2)_s-$; wherein each $R^{12}$ and $R^{12'}$ may independently optionally be substituted with 1 to 3 substituents selected from the group consisting of halogen, $OR^{11}$, alkoxy, heterocycloalkyl, $-NR^{11}C(O)NR^{11}R^{11'}$, $-C(O)NR^{11}R^{11'}$, $-NR^{11}C(O)R^{11'}$, $-CN$, oxo, $-NR^{11}SO_2R^{11'}$, $-OC(O)R^{11}$, $-SO_2NR^{11}R^{11'}$, $-SOR^{13}$, $-S(O)_2R^{13}$, $-COOH$ and $-C(O)OR^{13}$; each $R^{13}$ is independently alkyl, aryl, arylalkyl, heteroaryl, or heteroarylalkyl, each of which may optionally be substituted with $-(CH_2)_wOH$;

each $R^{14}$ is independently alkoxy, alkoxycarbonyl, $-C(O)NR^{12}R^{12'}$, $-NR^{11}R^{11'}$, $-C(O)R^{12}$, $-NR^{11}C(O)NR^{11}R^{11'}$ or $-N$-heteroaryl;

each $R^{15}$ is independently $-(CH_2)_pN(R^{12})C(O)R^{12'}$, $-(CH_2)_pCN$, $-(CH_2)_pN(R^{12})C(O)OR^{12'}$, $-(CH_2)_pN(R^{12})C(O)NR^{12}R^{12'}$, $-(CH_2)_pN(R^{12})SO_2R^{12}$, $-(CH_2)_pSO_{12}NR^{12}R^{12'}$, $-(CH_2)_pC(O)NR^{12}R^{12'}$, $-(CH_2)_pC(O)OR^{12}$, $-(CH^2)_pOC(O)OR^{12}$, $-(CH_2)_pOC(O)R^{12}$, $-(CH_2)_pOC(O)NR^{12}R^{12'}$, $-(CH_2)_pN(R^{12})SO_2NR^{12}R^{12'}$, $-(CH_2)_pOR^{12}$, $-(CH_2)_pOC(O)N(R^{12})(CH_2)_mOH$, $-(CH_2)_pSOR^{12}$, $-(CH_2)_pSO_2R^{12}$, $-(CH_2)_pNR^{11}R^{11'}$ or $-(CH_2)_pOCH_2C(O)N(R^{12})(CH_2)_mOH$;

each $R^{16}$ is independently halo, alkyl, alkenyl, alkynyl, alkoxy, $-(CH_2)_pNR^{11}C(O)NR^{11}R^{11'}$, $-(CH_2)_pC(O)NR^{11}R^{11'}$, $-(CH_2)_pNR^{11}C(O)R^{11'}$, $-CN$, $-(CH_2)_pNR^{11}SO_2R^{11'}$, $-(CH_2)_pOC(O)R^{11}$, $-(CH_2)_pSO_2NR^{11}R^{11'}$, $-(CH_2)_pSOR^{13}$, $-(CH_2)_pCOOH$ or $-(CH_2)_pC(O)OR^{13}$;

X is $CR^{11}R^{11'}$, O, S, S(O), $S(O)_2$, or $NR^{11}$;

m is an integer between 1 and 6;

p is an integer from 0 to 5;

q and s are each independently an integer between 1 and 3; and w is an integer between 0 and 5.

In some embodiments, A is $CH_2CH_2$ or $CH_2CH_2CH_2$, preferably $CH_2CH_2CH_2$.

In some embodiments, each $R^4$ and $R^5$ is independently alkyl, for example, methyl or ethyl, preferably ethyl.

In some embodiments, Y is a monocyclic heteroaromatic moiety, for example a nitrogen containing heteraromatic moiety such as nitrogen containing five membered heteraromatic moiety.

In some embodiments, Y is a heterocyclic moiety containing at least two heteroatoms, for example, a five membered heterocyclic moiety containing at least two heteroatoms or at least three heteroatoms.

In some embodiments Y is substituted with one $R^{10}$. $R^{10}$ can be positioned, for example, 1,3 relative to the point of attachment of Y to the adjacent chain carbon or 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, oxazolyl, thiazolyl, or thiophenyl. In some embodiments, $R^{10}$ is substituted with 1-3 $R^{16}$. In some embodiments, $R^{16}$ halo, alkyl, or alkoxy, for example chloro, fluoro, methyl, cyano, or methoxy.

In some embodiments, $R^{10}$ is a bicyclic heteroaryl, for example indolyl, benzimidazolyl, benzoxazolyl, benzofuranyl, benzothiophenyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ is arylalkyl or heteroarylalky, for example a monocyclic or bicyclic arylalkyl or monocyclic or bicyclic heteroarylalkyl. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments, $R^{10}$ includes an unsaturated or partially unsaturated cyclic moiety, for example a cyclyl or heterocyclyl moiety. The cyclic moiety can either be directly attached to Y or attached via a linker such as an alkylenyl linker. In some embodiments, $R^{10}$ is substituted with 1-3 $R^{16}$. In some embodiments, $R^{16}$ is halo, alkyl, or alkoxy, for example chloro, fluoro, methyl, cyano, or methoxy.

In some embodiments Y is oxadiazole or triazole.

In some embodiments, Y is

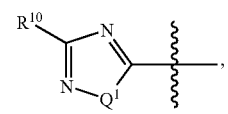

wherein Q1 is O or $NR^2$, preferably O or NH. In some embodiments, $R^{10}$ aryl, arylalkyl, heteroaryl, or heteroarylalkyl, for example optionally substituted with one or more $R^{16}$. In some embodiments, $R^{10}$ is substituted with one $R^{16}$, such as halo (e.g., fluoro or chloro) or alkoxy.

In another aspect, the invention features a compound of formula (IV)

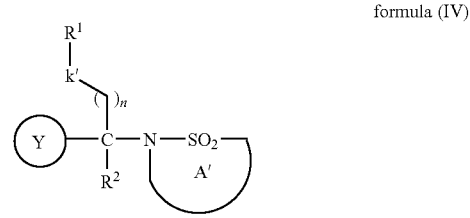

formula (IV)

wherein, $R^1$ is hydrogen, aryl, heteroaryl, arylalkyl, heteroarylalkyl, cyclyl, cyclylalkyl, heterocyclyl, heterocyclylalkyl, alkyl, alkenyl, alkynyl, or $R^1$ can be taken together with $R^2$ or $R^3$ to form a ring; each of which is optionally substituted with 1-4 $R^6$;

k' is a bond, O, C(O), C(O)O, OC(O), C(O)$NR^3$, $NR^3$C(O), S, SO, $SO_2$, $CR^2$=$CR^2$, OR C≡C;

n is 0-6, preferably 1-3;

$R^2$ is hydrogen, $C_1$-$C_6$ alkyl, $C_2$-$C_6$ alkenyl, or $C_2$-$C_6$ alkynyl;

A' is heterocyclyl; optionally substituted with 1-3 $R^9$;

Y is a monocyclic aryl or monocyclic heteroaryl; each of which is optionally substituted with 1-4 $R^{10}$;

each $R^6$ is independently halo, alkyl, alkenyl, alkynyl, cyclyl, heterocyclyl, aryl, heteroaryl, alkoxy, haloalkyl, haloalkyloxy, haloalkylthio, acetyl, cyano, nitro, hydroxy, oxo, C(O)$OR^2$, OC(O)$R^2$, N($R^3$)$_2$, C(O)N($R^3$)$_2$, $NR^3$C(O)$R^2$, or $SR^2$;

$R^9$ is halo, alkyl, cyclyl, heterocyclyl, aryl, heteroaryl, alkoxy, haloalkyl, haloalkyloxy, haloalkylthio, acetyl, cyano, nitro, hydroxy, oxo, C(O)$OR^2$, OC(O)$R^2$, N($R^2$)$_2$, C(O)N($R^2$)$_2$, $NR^2$C(O)$R^2$, $SR^2$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —$OR^{11}$, —$NR^{11}R^{11'}$, —$CF_3$, —$SO_2R^{12}$, —OC(O)$R^{11}$, —$SO_2NR^{12}R^{12'}$, —(CH$_2$)$_m$$R^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to from —(CH$_2$)$_q$X(CH$_2$)$_s$—; wherein each $R^{12}$ and $R^{12'}$ may independently optionally be substituted with 1 to 3 substituents selected from the group consisting of halogen, $OR^{11}$, alkoxy, heterocycloalkyl, —$NR^{11}$C(O)$NR^{11}R^{11'}$, —C(O)$NR^{11}R^{11'}$, —$NR^{11}$C(O)$R^{11'}$, —CN, oxo, —$NR^{11}SO_2R^{11'}$, —OC(O)$R^{11}$, —$SO_2NR^{11}R^{11'}$, —$SOR^{13}$, —S(O)$_2R^{13}$, —COOH and —C(O)$OR^{13}$;

each $R^{13}$ is independently alkyl, aryl, arylalkyl, heteroaryl, or heteroarylalkyl, each of which may optionally be substituted with —(CH$_2$)$_w$OH;

each $R^{14}$ is independently alkoxy, alkoxycarbonyl, —C(O)$NR^{12}R^{12'}$, —$NR^{11}R^{11'}$, —C(O)$R^{12}$, —$NR^{11}$C(O)$NR^{11}R^{11'}$ or —N-heteroaryl;

each $R^{15}$ is independently heterocycloalkyl, heteroaryl, —CN, —(CH$_2$)$_p$N($R^{12}$)C(O)$R^{12'}$, —(CH$_2$)$_p$CN, —(CH$_2$)$_p$N($R^{12}$)C(O)$OR^{12'}$, —(CH$_2$)$_p$N($R^{12}$)C(O)$NR^{12}R^{12'}$, —(CH$_2$)$_p$N($R^{12}$)$SO_2R^{12'}$, —(CH$_2$)$_p$$SO_2NR^{12}R^{12'}$, —(CH$_2$)$_p$C(O)$NR^{12}R^{12'}$, —(CH$_2$)$_p$N($R^{12}$)$SO_2NR^{12}R^{12'}$, —(CH$_2$)$_p$$OR^{12}$, —(CH$_2$)$_p$OC(O)N($R^{12}$)(CH$_2$)$_m$OH, —(CH$_2$)$_p$$SOR^{12}$ or —(CH$_2$)$_p$OCH$_2$C(O)N($R^{12}$)(CH$_2$)$_m$OH;

each $R^{16}$ is independently halo, alkyl, alkenyl, alkynyl, alkoxy, —(CH$_2$)$_p$$NR^{11}$C(O)$NR^{11}R^{11'}$, —(CH$_2$)$_p$C(O)$NR^{11}R^{11'}$, —(CH$_2$)$_p$$NR^{11}$C(O)$R^{11'}$, —CN, —(CH$_2$)$_p$$NR^{11}SO_2R^{11'}$, —(CH$_2$)$_p$OC(O)$R^{11}$, —(CH$_2$)$_p$$SO_2NR^{11}R^{11'}$, —(CH$_2$)$_p$$SOR^{13}$, —(CH$_2$)$_p$COOH or —(CH$_2$)$_p$C(O)$OR^{13}$;

X is $CR^{11}R^{11'}$, O, S, S(O), S(O)$_2$, or $NR^{11}$;

m is an integer between 1 and 6;

p is an integer from 0 and 5.

q and s are each independently an integer between 1 and 3; and w is an integer between 0 and 5.

In some embodiments, the compound of formula (IV), comprises an enriched preparation of formula (IV').

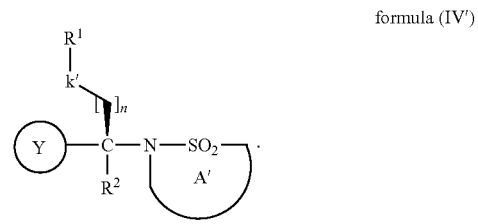

formula (IV')

In some embodiments, the compound of formula (IV), comprises an enriched preparation of formula (IV")

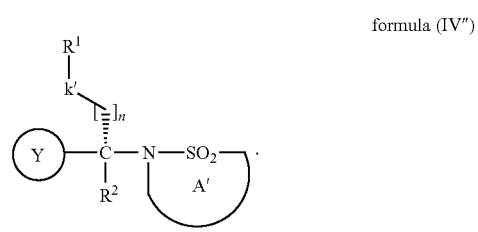

formula (IV")

In some embodiments, A' is a 5 or 6 membered heterocyclyl.

In some embodiments, the 5 or 6 membered heterocyclyl includes at least two nitrogen atoms.

In some embodiments, A' is

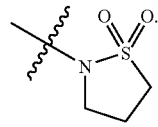

In some embodiments, A' is substituted with one $R^9$, for example, N($R^2$)$_2$.

In some embodiments, n is 1;

k' is a bond or O; and $R^1$ is aryl, heteroaryl, arylalkyl, or heteroarylalkyl.

In some embodiments, n is 1;

k' is O; and $R^1$ is arylalkyl.

For example, $R^1$ can be phenylmethyl.

In some embodiments, n is 2;

k' is a bond; and $R^1$ is aryl.

In some embodiments, Y is a monocyclic heteroaromatic moiety, for example, a nitrogen containing heteraromatic moiety, such as a nitrogen containing 5 membered heteraromatic moiety.

In some embodiments, Y is a heterocyclic moiety containing at least two heteroatoms, for example, a 5 membered heterocyclic moiety containing at least two heteroatoms or a heterocyclic moiety containing at least 3 heteroatoms.

In some embodiments, Y is substituted with 1 $R^{10}$. The $R^{10}$ can be positioned, for example, 1,3 relative to the point of attachment of Y to the adjacent chain carbon or can be positioned, for example, 1,2 relative to the point of attachment of Y to the adjacent chain carbon.

In some embodiments, $R^{10}$ is aryl or heteroaryl, for example a monocyclic aryl or monocyclic heteroaryl such as phenyl, pyridyl, or thiophenyl. In some embodiments, $R^{10}$ is substituted with 1-3 $R^{16}$. In some embodiments, $R^{16}$ is halo, alkyl, or alkoxy, for example chloro, fluoro, methyl, or methoxy.

In some embodiments, $R^{10}$ is a bicyclic heteroaryl, for example indolyl, imidazolyl, benzoxazolyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, or methoxy.

In some embodiments, Y is oxadiazole or triazole.

In another aspect, the invention features a compound of formula (V),

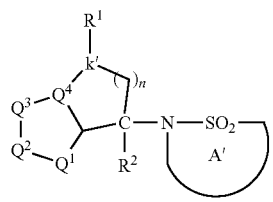

formula (V)

wherein, $Q^1$, $Q^2$, $Q^3$ and $Q^4$ together with the carbon to which they are attached form a heteroaryl moiety, and each $Q^1$, $Q^2$, $Q^3$ and $Q^4$ is independently S, O, N, $CR^2$, $CR^{10}$, $NR^2$, or $NR^{10}$.

In some embodiments, the compound of formula (V), comprises an enriched preparation of formula (V')

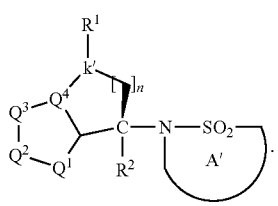

formula (V')

In some embodiments, the compound of formula (V), comprises an enriched preparation of formula (V'')

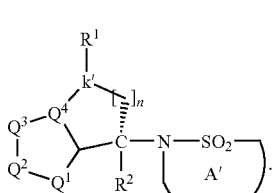

formula (V'')

In some embodiments, $Q^1$ and $Q^4$ are each independently S, O, N, or $NR^{10}$.

In some embodiments, $Q^1$ and $Q^3$ are each independently S, O, N, or $NR^{10}$.

In some embodiments, $Q^2$ is $CR^2$ or $CR^{10}$.
In some embodiments, $Q^2$ is S, O, N, or $NR^{10}$.
In some embodiments, at least one of $Q^2$ or $Q^3$ is $CR^2$ or $CR^{10}$.
In some embodiments, at least two of $Q^1$, $Q^2$, $Q^3$, or $Q^4$ is S, O, N, or $NR^{10}$.
In some embodiments, $Q^1$, $Q^2$, and $Q^3$ are each independently S, O, N, or $NR^{10}$.
In some embodiments, $Q^1$ is $NR^{10}$.
In some embodiments, one of $Q^2$, $Q^3$, or $Q^4$ is $CR^2$.
In some embodiments, $Q^2$ is $CR^{10}$.
In some embodiments, $Q^3$ is $CR^2$.
In some embodiments, $Q^1$, $Q^2$, $Q^3$ and $Q^4$ together form

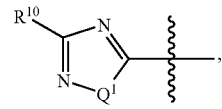

In some embodiments, $Q^1$ is $NR^2$.
In some embodiments, $Q^1$, $Q^2$, $Q^3$ and $Q^4$ together form

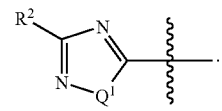

In some embodiments, $Q^1$ is $NR^{10}$.

In another aspect, the invention features a compound of formula (VI),

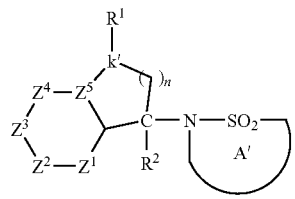

formula (VI)

wherein $Z^1$, $Z^2$, $Z^3$, $Z^4$, and $Z^5$ together form an aryl or heteroaryl moiety, and each $Z^1$, $Z^2$, $Z^3$, $Z^4$, and $Z^5$ is independently N, $CR^{10}$, or $CR^2$.

In some embodiments, the compound of formula (IV), comprises an enriched preparation of a compound of formula (VI').

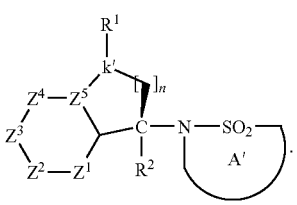

formula (VI')

In some embodiments, the compound of formula (VI), comprises an enriched preparation of a compound of formula (VI'').

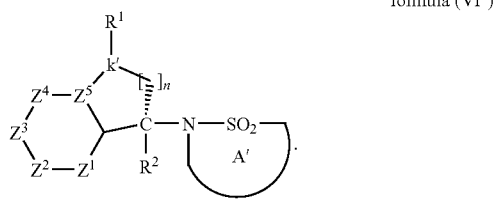

formula (VI")

In some embodiments, one of $Z^1$, $Z^2$, $Z^3$, $Z^4$, and $Z^5$ is N.
In some embodiments, two of $Z^1$, $Z^2$, $Z^3$, $Z^4$, and $Z^5$ are N.
In some embodiments, three of $Z^1$, $Z^2$, $Z^3$, $Z^4$, and $Z^5$ is N.
In some embodiments, two of $Z^1$ and $z^2$ are N.
In some embodiments, two of $Z^1$ and $Z^3$ are N.
In some embodiments, two of $Z^1$ and $Z^4$ are N.
In some embodiments, two of $Z^1$, $Z^3$, and $Z^5$ are N.

In some embodiments, the compound is a compound of formula (IV), wherein Y is substituted with a single substituent $R^{10}$. For example, $R^{10}$ can be aryl or heteroaryl, optionally substituted with up to three independent $R^{16}$.

In some embodiments, $R^{10}$ is aryl or heteroaryl, for example a monocyclic aryl or monocyclic heteroaryl such as phenyl, pyridyl, or thiophenyl. In some embodiments, $R^{10}$ is substituted wit 1-3 $R^{16}$. In some embodiments, $R^{16}$ is halo, alkyl, or alkoxy, for example chloro, fluoro, methyl, or methoxy.

In some embodiments, $R^{10}$ is a bicyclic heteroaryl, for example indolyl, imidazolyl, benzoxazolyl, or benzthiazolyl. In some embodiments, $R^{10}$ is substituted with 1-3 $R^{16}$. In some embodiments, $R^{16}$ is halo, alkyl, or alkoxy, for example chloro, fluoro, methyl, or methoxy.

In some embodiments, $R^{10}$ is $R^{15}$.

In some embodiments, Y is substituted with a second $R^{10}$, for example an alkyl, halo or alkoxy.

In another aspect, the invention features a pharmaceutically acceptable salt comprising a compound of any of the formulae described herein.

In another aspect, the invention features a composition comprising a compound of any of the formulae described herein and a pharmaceutically acceptable carrier.

In another aspect, the invention features a method of treating metabolic syndrome comprising administering to a subject a compound of any of the formulae described herein.

In another aspect, the invention features a method of treating or delaying the onset of diabetes comprising administering to a subject a compound of any of the formulae described herein. For example, the method can include administering a compound to a subject to improve glucose tolerance, reduce fasting blood glucose, reduce post prandial blood glucose, and/or reduce HbA1c levels in a subject.

In another aspect, the invention features a method of treating obesity comprising administering to a subject a compound of any of the formulae described herein.

In one aspect, the invention features a compound that has a structure of a formula described herein, and the compound competes with ghrelin for binding to GHS-R.

In another aspect, the invention features a compound that has a structure of formula described herein, and the compound is effective for altering appetite of a subject or for altering feeding behavior of the subject. For example, a compound described herein can be administered to a subject to reduce food intake of that subject.

In another aspect, the invention features a compound that has a structure of formula described herein, and the compound is effective for modulating resistin, leptin, or adiponetin mRNA in white adipose tissue (WAT) or for modulating levels of insulin, IGF-1, GH, cortisol, triglycerides, free fatty acids, cholesterols (e.g., VLDL or HLDL particles) or glucose, e.g., in the blood. For example a compound described herein can be administered to a subject to reduce the level of cholesterol and/or triglycerides in the subject and/or reduce the ratio of total cholesterol to HDL cholesterol in a subject.

In another aspect, the invention features a compound that has a structure of formula described herein, and the compound is effective for inhibiting growth of a neoplastic cell, e.g., a cell of a ghrelin-sensitive neoplastic disorder or a GHS-R antagonist-sensitive neoplastic disorder.

In another aspect, the invention features a compound listed in Table 1.

In one embodiment, the compound is an enantiomerically enriched isomer of a stereoisomer described herein. For example, the compound has an enantiomeric excess of at least about 10%, 15%, 20%, 25%, 30%, 35%, 40%, 45%, 50%, 55%, 60%, 65%, 70%, 75%, 80%, 85%, 90%, 95%, 965, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter, e.g., the position corresponding to the carbon alpha to the sulfonamide nitrogen in formula (I). Exemplary R/S configurations can be those provided in an example described herein, e.g., those described in the Table below, or the configuration of the majority or minority species in a synthetic scheme described herein. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a compound described herein includes a preparation of a compound disclosed herein that is enriched for a structure or structures having a selected stereochemistry, e.g., R or S, at a selected stereocenter, e.g., the carbon alpha to the sulfonamide nitrogen of a formula described herein e.g., formula (I), (II), (III), (IV), (V), or (VI).

Exemplary R/S configurations can be those provided in an example described herein, e.g., those described in the Table below, or the configuration of the majority or minority species in a synthetic scheme described herein. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided, herein, e.g., in an example described herein, e.g., those described in the Table below. By enriched is meant at least 60%, e.g., of the molecules of compound in the preparation have a selected stereochemistry of a selected stereocenter. In preferred embodiments it is at least 65%, 70%, 75%, 80%, 85%, 90%, 95%, 96%, 97%, 98%, or 99%. Enriched refers to the level of a subject molecule(s) and does not connote a process limitation unless specified.

In one embodiment, a preparation of a compound disclosed herein, is enriched for isomers (subject isomers) which are diastereromers of the a compound described herein. For example, a compound having a selected stereochemistry, e.g., R or S, corresponding to a selected stereocenter, e.g., the position corresponding to the carbon alpha to the sulfonamide nitrogen of a formula described herein e.g., formula (I), (II), (III), (IV), (V), or (VI). Exemplary R/S configurations can be those provided in an example described herein, e.g., those described in the Table below, or the configuration of the majority or minority species in a synthetic scheme described herein. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%. Diastereromer, when used herein, refers to a stereoisomer of a compound having two or more chiral centers that is not a mirror image of another stereoisomer of the same compound.

In another aspect, the invention features an organic compound that modulates (e.g., antagonizes, agonizes, or inversely agonizes) GHS-R activity, the compound having a molecular weight of less than 700 Daltons, and having fewer than four L- or D-amino acids (e.g., and any salt thereof). For example, the compound may, in certain embodiments, bind or otherwise include a metal cation.

In one embodiment, the compound has a molecular weight less than [D-Lys-3]-GHRP6 or H(2)N-D-arg-Pro-Lys-Pro-d-Phe-Gln-d-Trp-Phe-d-Trp-Leu-Leu-NH(2) (L 756,867) or within 2, 1.5, 1.4, 1.2, 1.1, 0.8, 0.6, or 0.5 fold that of [D-Lys-3]-GHRP-6 or L 756,867.

In another aspect, the invention features a pharmaceutical composition that includes a compound described herein, e.g., a compound listed in Table 1 or described above, and a pharmaceutically acceptable carrier.

In another aspect, the invention features a method of decreasing GHS-R activity in a subject. The method includes administering the compound described herein to the subject in an amount effective to decrease GHS-R activity in the subject. In one embodiment, the subject is a mammal, e.g., a human, a primate, a dog, a cat, a racing, purebred, or an agricultural mammal. In one embodiment, the subject is overweight or obese.

In one embodiment, GHS-R activity is modulated in one or more of the following tissues: pituitary, brain, spinal cord, uterus, spleen, pancreas, kidney, adrenal gland, skeletal muscle, thyroid, liver, hypothalamus, heart, lung, pancreas, intestine, and adipose tissue.

In another aspect, the invention features a method that includes: identifying a subject as having obesity, being at risk for obesity using established clinical criteria (e.g., NIH Clinical Guidelines on the Identification and Evaluation, and Treatment of Overweight and Obesity in Adults" (1998)), having insulin resistance, or being overweight; and administering a compound described herein to the subject in an amount effective to reduce weight or prevent weight gain, reduce fat content, increase metabolic activity, reduce blood glucose concentration, reduce blood insulin concentration, increase insulin sensitivity, reduce the level of cholesterol and/or triglycerides in the and/or reduce the ratio of total cholesterol to HDL cholesterol.

Obesity can also be defined by a subject's body mass index (BMI), which is a tool for indicating weight status, and is a measure of weight for height. (See Garrow J S and Webster J. Quetelet's index (W/H2) as a measure of fatness. International Journal of Obesity 1985;9:147-153.) A BMI of 18.5 or below is considered underweight, a BMI of between 18.5 and 24.9 is considered normal, a BMI of between 25.0 and 29.9 is considered overweight, and a BMI of 30.0 or greater is considered obese. The BMI ranges are based on the effect body weight has on disease and death. (See World Health Organization. Physical status: The use and interpretation of anthropometry. Geneva, Switzerland: World Health Organization 1995. WHO Technical Report Series.) As BMI increases, the risk for some disease increases.

In another aspect, the invention features a method of treating a subject having Prader-Willi Syndrome associated hyperphagia and obesity. Prader-Willi Syndrome is a genetic disease localized to chromosome 15 that is characterized by hyperphagia, obesity, hypotonia, and mild mental retardation. (See e.g., Growth Hormone & IGF Research 13 (2003) 322-327; Growth Hormone & IGF Research 14 (2004) 1-15; The Journal of Clinical Endrocrinology & Metabolism 88(1):174-178; The Journal of Clinical Endrocrinology & Metabolism 88(5):2206-2212; The Journal of Clinical Endrocrinology & Metabolism 88(5):3573-3576; The Journal of Clinical Endrocrinology & Metabolism 87(12):5461-5464.) The method includes administering a compound described herein, to the subject, in an amount effective to maintain or reduce weight in a subject, and/or reduce appetite in a subject, control behavioral disturbances secondary to the hyperphagia, and reduce risk of morbidity and mortality associated with the extreme obesity of these individuals. Obesity related mortality would include type II diabetes, cardiovascular disease, and stroke. In some instances, a subject having Prader-Willi Syndrome associated obesity can be identified, for example by DNA methylation test, microsatellite tests, and/or clinical phenotyping of the patient.

In another aspect, the invention features a method of treating or preventing insulin-related disorders, e.g., diabetes, retinopathy, neuropathy, nephropathy, and end organ damage. The method includes administering a compound described herein, to the subject, in an amount effective to treat or prevent insulin resistance in the subject.

In another aspect, the invention features a method that includes: administering a compound described herein, to the subject, in an amount effective to reduce GHS-R activity in the subject (e.g., administering an antagonist or an inverse agonist). In one embodiment, the subject is diagnosed with or has a disorder selected from the group consisting of: cancer, diabetes, neurological disorder, obesity, age-associated disorder, neoplastic disorder, non-neoplastic disorder, cardiovascular disorder, metabolic disorder, or dermatological disorder.

For example, the compound is administered orally, or parenterally, e.g., by injection, and so forth. In one embodiment, the compound is administered at a plurality of intervals, e.g., regular intervals. In one embodiment, the method further includes monitoring the subject for GH or IGF-1 activity; monitoring the subject for gene or protein regulated by GHS-R (e.g., resistin, leptin, or adiponectin) or monitoring the subject for blood or plasma levels of ghrelin, insulin, leptin and/or IGF-1.

In another aspect, the invention features a method of treating or preventing a disorder characterized by ghrelin levels (e.g., elevated ghrelin levels such as Prader-Willi syndrome) or GHS-R mediated signaling levels that exceed a desired or normal level.

The method includes: administering a compound described herein, to a subject, in an amount effective to attenuate, inhibit, or block GHS-R mediating signaling in the subject.

In another aspect, the invention features a method of treating or preventing a disorder characterized by ghrelin levels or GHS-R mediated signaling levels that are below a desired or normal level. The method includes: administering a compound described herein, to a subject, in an amount effective to increase GHS-R mediating signaling in the subject, e.g., in one or more of the following tissues: pituitary, brain, spinal cord, uterus, spleen, pancreas, kidney, adrenal gland, skeletal muscle, thyroid, liver, small intestine, and heart.

In another aspect, the invention features a method of treating or preventing a GHS-R sensitive neoplastic disorder. The method includes administering a compound described herein, to a subject, in an amount effective to ameliorate the neoplastic disorder (e.g., to inhibit proliferation, kill cells, or reduce or inhibit growth or an activity of neoplastic cells) in the subject.

In another aspect, the invention features a method of modulating feeding behavior in a subject. The method includes: administering a compound described herein, to a subject, in an amount effective to modulate a feeding behavior of the subject, e.g., to increase appetite in the subject. In one embodiment, the compound is administered prior to (e.g., at least 0.5, 1, 2, or 4 hours prior to) a mealtime or expected time at which food would be made available. In a related aspect, the method includes administering a compound, to a subject, in an amount effective to modulate a feeding behavior of the subject, e.g., to decrease appetite in the subject. In one embodiment, the compound is administered prior to (e.g., at least 0.5, 1, 2, or 4 hours prior to) a mealtime or expected time at which food would be made available.

In another aspect, the invention features a method of treating or preventing a neoplastic disorder in a subject. The method includes: determining if the neoplastic disorder is mediated by cells that are sensitive to ghrelin or a GHS-R agonist or to a GHS-R antagonist, and selecting a GHS-R interacting compound described herein; and administering the selected compound to the subject.

In another aspect, the invention features a method of treating or preventing a neurodegenerative disorder. The method includes: administering a compound described herein, to a subject, in an amount effective to ameliorate the neurodegenerative disorder in the subject.

In another aspect, the invention features a method of treating or preventing a metabolic disorder. The method includes: administering a compound described herein, to a subject, in an amount effective to ameliorate the metabolic disorder in the subject.

In another aspect, the invention features a method of treating or preventing a cardiovascular disorder. The method includes: administering a compound described herein, to a subject, in an amount effective to ameliorate the cardiovascular disorder in the subject. For example, a compound described herein can be administered to a subject to reduce the level of cholesterol and/or triglycerides in the subject and/or reduce the ratio of total cholesterol to HDL cholesterol in the subject.

In another aspect, the invention features a kit that includes a compound described herein; and instructions for administering the compound to treat a disorder described herein, e.g., an eating disorder, a metabolic disorder characterized by excess or undesired GHS-R activity, a cardiovascular disorder, a neurodegenerative disorder, and a disorder associated with altered GH/IGF-1 activity.

In another aspect, the invention features a kit that includes (1) a compound described herein; and (2) one or more reagents for monitoring expression of one or more genes regulated by GHS-R, e.g., resistin, leptin, or adiponectin, or one or more reagents for monitoring plasma levels of a metabolic regulator such as ghrelin, insulin, IGF-1 or leptin.

In one aspect, the invention features a method of modulating IGF-1 levels (e.g., circulating IGF-1 levels) in a subject. The method includes administering a compound described herein. In one embodiment, a compound described herein is administered to the subject in an amount effect to modulate IGF-1 levels (e.g., increase or decrease IGF-1 levels). In particular, antagonists are believed to be effective for decreasing IGF-1 levels, and agonists are believed to be effective for increasing IGF-1 levels.

In one aspect, the invention features a method of modulating insulin levels (e.g., circulating insulin levels) in a subject. The method includes administering a compound described herein. In one embodiment, a compound described herein is administered to the subject in an amount effect to modulate insulin levels (e.g., increase or decrease insulin levels). In particular, antagonists are believed to be effective for decreasing insulin levels, and agonists are believed to be effective for increasing insulin levels.

In one aspect, the invention features a method of modulating glucose levels (e.g., circulating or blood glucose levels) in a subject. The method includes administering a compound described herein. In one embodiment, a compound described herein is administered to the subject in an amount effect to modulate glucose levels (e.g., increase or decrease glucose levels). In particular, agonists are believed to be effective for increasing glucose levels, and antagonists are believed to be effective for decreasing glucose levels.

The term "halo" refers to any radical of fluorine, chlorine, bromine or iodine. The term "alkyl" refers to a hydrocarbon chain that may be a straight chain or branched chain, containing the indicated number of carbon atoms. For example, C1-C10 indicates that the group may have from 1 to 10 (inclusive) carbon atoms in it. The term "lower alkyl" refers to a C1-C8 alkyl chain. In the absence of any numerical designation, "alkyl" is a chain (straight or branched) having 1 to 10 (inclusive) carbon atoms in it. The term "alkoxy" refers to an —O-alkyl radical. The term "alkylene" refers to a divalent alkyl (i.e., —R—). The term "aminoalkyl" refers to an alkyl substituted with an amino. The term "mercapto" refers to an —SH radical. The term "thioalkoxy" refers to an —S-alkyl radical.

The term "alkenyl" refers to a hydrocarbon chain that may be a straight chain or branched chain having one or more carbon-carbon double bonds. The alkenyl moiety contains the indicated number of carbon atoms. For example, C2-C10 indicates that the group may have from 2 to 10 (inclusive) carbon atoms in it. The term "lower alkenyl" refers to a C2-C8 alkenyl chain. In the absence of any numerical designation, "alkenyl" is a chain (straight or branched) having 2 to 10 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, C2-C10 indicates that the group may have from 2 to 10 (inclusive) carbon atoms in it. The term "lower alkynyl" refers to a C2-C8 alkynyl chain. In the absence of any numerical designation, "alkynyl" is a chain (straight or branched) having 2 to 10 (inclusive) carbon atoms in it.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkenyl" refers to an alkenyl substituted with an aryl. The term "arylalkynyl" refers to an alkynyl substituted with an aryl. The term "arylalkoxy" refers to an alkoxy substituted with aryl.

The terms "cycloalkyl" or "cyclyl" as employed herein includes saturated and partially unsaturated cyclic hydrocarbon groups having 3 to 12 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms if N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkenyl" refers to an alkenyl substituted with a heteroaryl. The term "heteroarylalkynyl" refers to an alkynyl substituted with a heteroaryl. The term "heteroarylalkoxy" refers to an alkoxy substituted with heteroaryl.

The term "heterocyclyl" or "heterocyclylalkyl" refers to a nonaromatic 5-8 membered monocyclic, 5-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morphonlinyl, tetrahydrofuranyl, and include both bridged and fused ring systems. The term "heterocyclylalkyl" refers to an alkyl substituted with a heterocyclyl.

The term "sulfinyl" refers to a sulfur attached to two oxygen atoms through double bonds. An "alkylsulfonyl" refers to an alkyl substituted with a sulfonyl. The term "amino acid" refers to a molecule containing both an amino group and a carboxyl group. Suitable amino acids include, without limitation, both the D- and L-isomers of the 20 naturally occurring amino acids found in peptides (e.g., A, R, N, C, D, Q, E, G, H, I, L, K, M, F, P, S, T, W, Y, V (as known by the one letter abbreviations)) as well as unnaturally occurring amino acids prepared by organic synthesis or other metabolic routes.

The term "amino acid side chain " refers to any one of the twenty groups attached to the α-carbon in naturally occurring amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc.

The term "substituents" refers to a group "substituted " on an alkyl, cycloalkyl, aryl, heterocyclyl, or heteroaryl group at any atom of that group. Any moiety described herein can be further substituted with a substituent. Suitable substituents include, without limitation, halo, hydroxy, mercapto, oxo, nitro, haloalkyl, alkyl, aryl, aralkyl, alkoxy, thioalkoxy, aryloxy, amino, alkoxycarbonyl, amido, carboxy, alkanesulfonyl, alkylcarbonyl, and cyano groups.

GHS-R can regulate the secretion of GH. GH itself is a regulator of IGF-1 production. Thus, compounds, e.g., compounds described herein, that modulate GHS-R activity can be used to modulate (e.g., increase or decrease) activity of the GH/IGF-1 axis. For example, agonists of GHS-R can be used to increase GH activity and/or IGF-1 activity. Antagonists of GHS-R can be used to decrease GH activity and/or IGF-1 activity. This application also incorporates by reference U.S. Ser. No. 10/656,530, the contents of which include uses for which a compound described herein may be used, e.g., as a modulator of the GH/IGF-1 axis.

The GH/IGF-1 axis includes a series of extracellular and intracellular signaling components that have as a downstream target, the transcription factor Forkhead. Major components of the GH/IGF-1 axis can be divided into three categories: pre-IGF 1, IGF 1, and post IGF-1 components. "Pre IGF-1 components" include GH, GH-R, ghrelin, GHS-R, GHRH, GHRH-R, SST, and SST-R. "Post-IGF 1 components" include IGF-1-R and intracellular signaling components including PI(3) kinase, PTEN phosphatase, PI(3,4)P2, 14-3-3 protein, and PI(3,4,5)P3 phosphatidyl inositol kinases, AKT serine/threonine kinase (e.g., AKT-1, AKT-2, or AKT-3), or a Forkhead transcription factor (such as FOXO-1, FOXO-3, or FOXO-4). A "somatotroph axis signaling pathway component" refers to a protein that is one of the following: (i) a protein that is located in a somatotroph and that regulates GH release by the somatotroph, or (ii) a protein that directly binds to a protein in class (i). Exemplary somatotroph axis signaling pathway components of class (i) include cell surface receptors such as GHS-R, GHRH-R, and SST-R. Exemplary somatotroph axis signaling pathway components of class (ii) include GHRH, ghrelin, and SST.

A compound that modulates GH levels, e.g., by altering GHS-R activity can have downstream effects. For example, the compound can alter (e.g., increase or decrease) the levels or activity of an IGF-1 receptor signaling pathway effector. A "IGF-1 Receptor signaling pathway effector" refers a protein or other biologic whose levels are directly regulated by a Forkhead transcription factor in response to IGF 1. For example, expression of the gene encoding the protein can be directly regulated by a Forkhead transcription factor such as FOXO-1, FOXO-3a, or FOXO-4. Exemplary IGF-1 Receptor signaling pathway effector can include: GADD45, PA26, Selenoprotein P, Whip1, cyclin G2, and NIP3.

As used herein, "activity of the GH/IGF 1 axis" refers to the net effect of the axis components with respect to ability to stimulate GH secretion, increase IGF 1 levels, or increase IGF 1 receptor signaling. Accordingly, "downregulating the GH/IGF 1 axis" refers to modulating one or more components such that one or more of the following is reduced, e.g., decreased GH, decreased IGF 1, or decreased IGF 1 receptor signaling. For example, in some instances, GH levels are maintained but its action is inhibited; thus IGF 1 levels are decreased without decreasing GH levels. In some instances, both GH and IGF 1 levels are decreased.

A "antagonist" of a particular protein includes compounds that, at the protein level, directly bind of modify the subject component such that an activity of the subject component is decreased, e.g., by competitive or non-competitive inhibition, destabilization, destruction, clearance, or otherwise. For example, the decreased activity can include reduced ability to respond to an endogenous ligand. For example, an antagonist of GHS-R can reduce the ability of GHS-R to respond to ghrelin.

An "agonist" of a particular protein includes compounds that, at the protein level, directly bind or modify the subject component such that an activity of the subject component is increased, e.g., by activation, stabilization, altered distribution, or otherwise.

An "inverse agonist" of a particular protein includes a compound that, at the protein level, causes an inhibition of the constitutive activity of the protein (e.g., a receptor), with a negative intrinsic activity, for example by binding to and/or stabilizing an inactive form of the protein, which pushes the equilibrium away from formation of an active conformation of the protein.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

Certain compounds that agonize GHS-R to a lesser extent than ghrelin can function in assays as antagonists as well as agonists. These compounds antagonize activation of GHS-R by ghrelin because they prevent the full effect of ghrelin-receptor interaction. However, the compounds also, on their own, activate some receptor activity, typically less than a corresponding amount of ghrelin. Such compounds may be referred to as "partial agonists of GHS-R".

A subject with "normal" GH levels is one who would return a normal result using the glucose tolerance test in which glucose is ingested and blood levels of GH are measured by enzyme-linked immunosorbent assay (ELISA), radioimmunoassay (RIA) or polyclonal immunoassay. A normal result for this test is characterized by less than 1 ng/mL of GH within 1 to 2 hours of an oral glucose load. However, GH levels of a subject with excessive GH, as in one with acromegaly may not decrease below 1 ng/mL after ingesting glucose. Because GH levels oscillate every twenty to thirty minutes and varies in level according to the time of day, stress level, exercise, etc., a standard means of determining if GH levels are excessive is to administer glucose. This approach normalizes GH and is less affected by the pulsatility of GH, age, gender, or other factors. Alternatively or as a confirmation, since IGF 1 levels are invariably increased in acromegalic individuals, IGF 1 levels can be measured and compared to age and gender matched normal controls.

The term "an indicator of GH/IGF 1 axis activity" refers to a detectable property of the GH/IGF 1 axis that is indicative of activity of the axis. Exemplary properties include circulating GH concentration, circulating IGF 1 concentration, frequency of GH pulses, amplitude of GH pulses, GH concentration in response to glucose, IGF 1 receptor phosphorylation, and IGF 1 receptor substrate phosphorylation. A compound that modulated activity of GHS-R can alter one or more indicators of GH/IGF-1 axis activity.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 1 and 2 demonstrate that compounds 57 and 94 block ghrelin-induced food intake in mice.

FIGS. 4a-4f demonstrate improvement in insulin sensitivity in mice dosed with compounds 57 and 94.

FIG. 5 demonstrates improved plasma HbA1c levels and improved cholesterol levels at 28 days in mice dosed with compound 57.

FIG. 6 demonstrates improved plasma HbA1c levels, improved cholesterol levels and improved triglyceride levels at 28 days in mice dosed with compound 94.

DETAILED DESCRIPTION

Figure 1:
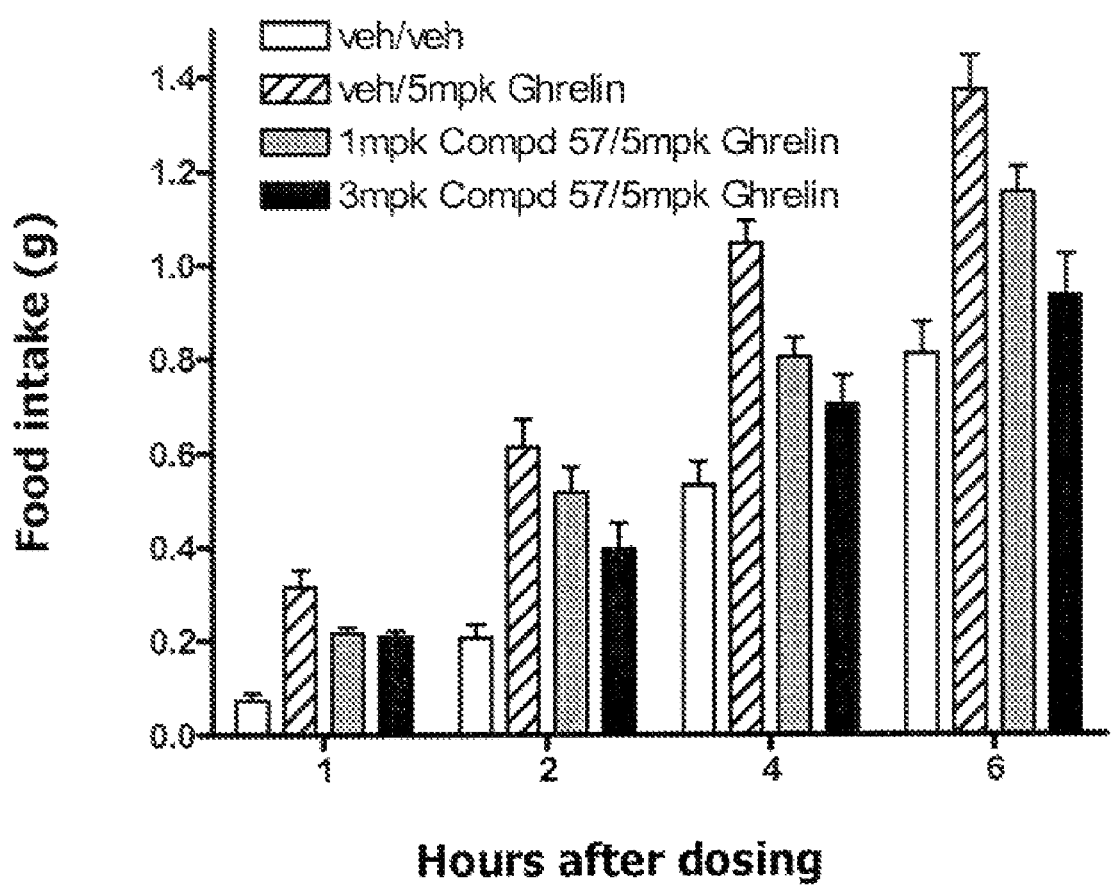

The compounds described herein can be used for a variety of purposes, e.g., therapeutic purposes. Many of the compounds antagonize GHS-R activity and can be used to reduce GHS-R activity, e.g., in a subject. Still other compounds agonize GHS-R and can be used to increase GHS-R activity, e.g., in a subject. Some of the disclosed compounds may also provide useful biological effects by modulating the activity of cellular components other than GHS-R.

Representative compounds of the invention are depicted below in Table 1. Other exemplary compounds are within the scope set forth in the Summary or are described elsewhere herein.

TABLE 1

Exemplary GHS-R Modulating Compounds

| Number | Name | Activity* |
|---|---|---|
| 1 | 3-Diethylamino-propane-1-sulfonic acid [(R)-2-benzyloxy-1-(3-phenyl-[1,2,4]oxadiazol-5-yl)-ethyl]-amide | C |
| 2 | 3-Diethylamino-propane-1-sulfonic acid {(R)-2-benzyloxy-1-[3-(2,6-dichloro-phenyl)-[1,2,4]oxadiazol-5-yl]-ethyl}-amide | A |
| 3 | 3-Diethylamino-propane-1-sulfonic acid {(R)-1-[5-(2,3-dichloro-phenyl)-2H-[1,2,4]triazol-3-yl]-3-phenyl-propyl}-amide | A |
| 4 | 3-Diethylamino-propane-1-sulfonic acid [(R)-3-phenyl-1-(3-o-tolyl-[1,2,4]oxadiazol-5-yl)-propyl]-amide | A |
| 5 | 3-Diethylamino-propane-1-sulfonic acid {(R)-1-[5-(4-fluoro-benzyl)-2H-[1,2,4]triazol-3-yl]-3-phenyl-propyl}-amide | A |
| 6 | 3-Diethylamino-propane-1-sulfonic acid [(R)-3-phenyl-1-(3-phenyl-[1,2,4]oxadiazol-5-yl)-propyl]-amide | A |
| 7 | 3-Diethylamino-propane-1 sulfonic acid [(R)-3-phenyl-1-(5-thiophen-3-yl-2H-[1,2,4]triazol-3-yl)-propyl]-amide | A |
| 8 | 3-Diethylamino-propane-1-sulfonic acid {(R)-3-phenyl-1-[5-(2,4,6-trifluoro-phenyl)-2H-[1,2,4]triazol-3-yl]-propyl}-amide | A |
| 9 | 3-Diethylamino-propane-1-sulfonic acid {(R)-1-[3-(3-methyl-pyridin-2-yl)-[1,2,4]oxadiazol-5-yl]-3-phenyl-propyl}-amide | B |
| 10 | 3-Diethylamino-propane-1-sulfonic acid {(R)-1-[3-(2-chloro-6-methyl-phenyl)-[1,2,4]oxadiazol-5-yl]-3-phenyl-propyl}-amide | B |
| 11 | 3-Diethylamino-propane-1-sulfonic acid [(R)-1-(5-benzo[1,3]dioxol-5-yl-2H-[1,2,4]triazol-3-yl)-3-phenyl-propyl]-amide | A |
| 12 | 3-Diethylamino-propane-1-sulfonic acid {(R)-1-[3-(2,6-dichloro-phenyl)-[1,2,4]oxadiazol-5-yl]-3-phenyl-propyl}-amide | A |
| 13 | 2-Diethylamino-ethanesulfonic acid [(R)-3-phenyl-1-(3-o-tolyl-[1,2,4]oxadiazol-5-yl)-propyl]-amide | C |
| 14 | 2-Diethylamino-ethanesulfonic acid {(R)-1-[3-(3-methyl-pyridin-2-yl)-[1,2,4]oxadiazol-5-yl]-3-phenyl-propyl}-amide | B |
| 15 | 3-Diethylamino-propane-1-sulfonic acid {(R)-1-[5-(3-fluoro-phenyl)-2H-[1,2,4]triazol-3-yl]-3-phenyl-propyl}-amide | A |
| 16 | 3-Diethylamino-propane-1-sulfonic acid {(R)-1-[3-(2-methoxy-phenyl)-[1,2,4]oxadiazol-5-yl]-3-phenyl-propyl}-amide | C |
| 17 | 2-Diethylamino-ethanesulfonic acid [(R)-3-phenyl-1-(3-phenyl-[1,2,4]oxadiazol-5-yl)-propyl]-amide | B |
| 18 | 2-Diethylamino-ethanesulfonic acid {(R)-1-[3-(2,6-dichloro-phenyl)-[1,2,4]oxadiazol-5-yl]-3-phenyl-propyl}-amide | B |

TABLE 1-continued

Exemplary GHS-R Modulating Compounds

| Number | Name | Activity* |
|---|---|---|
| 19 | 2-Diethylamino-ethanesulfonic acid {(R)-1-[3-(2-methoxy-phenyl)-[1,2,4]oxadiazol-5-yl]-3-phenyl-propyl}-amide | D |
| 20 | 3-Diethylamino-propane-1-sulfonic acid {(R)-1-[5-(1H-indol-5-yl)-2H-{1,2,4]triazol-3-yl]-3-phenyl-propyl}-amide | A |
| 21 | 3-Diethylamino-propane-1-sulfonic acid [(S)-3-phenyl-1-(3-o-tolyl-[1,2,4]oxadiazol-5-yl)-propyl]-amide | B |
| 22 | 3-Diethylamino-propane-1-sulfonic acid {(R)-1-[5-(4-chloro-phenyl)-2H-[1,2,4]triazol-3-yl]-3-phenyl-propyl}-amide | A |
| 23 | 3-Diethylamino-propane-1-sulfonic acid [(R)-3-phenyl-1-(5-phenyl-2H-[1,2,4]triazol-3-yl)-propyl]-amide | A |
| 24 | 3-Diethylamino-propane-1-sulfonic acid {(R)-1-[5-(4-chloro-benzyl)-2H-[1,2,4]triazol-3-yl]-3-phenyl-propyl}-amide | A |
| 25 | 3-Diethylamino-propane-1-sulfonic acid [(S)-2-benzyloxy-1-(5-phenyl-2H-[1,2,4]triazol-3-yl)-ethyl]-amide | B |
| 26 | 3-Diethylamino-propane-1-sulfonic acid [5-(4-chloro-benzyl)-2H-[1,2,4]triazol-3-ylmethyl]-amide | B |
| 27 | 2-Diethylamino-ethanesulfonic acid [(R)-3-phenyl-1-(3-pyridin-2-yl-[1,2,4]oxadiazol-5-yl)-propyl]-amide | B |
| 28 | 2-Diethylamino-ethanesulfonic acid [(R)-3-phenyl-1-(5-phenyl-2H-[1,2,4]triazol-3-yl)-propyl]-amide | A |
| 29 | 3-Diethylamino-propane-1-sulfonic acid {(R)-1-[5-(2-fluoro-phenyl)-2H-[1,2,4]triazol-3-yl]-3-phenyl-propyl}-amide | A |
| 30 | 3-Diethylamino-propane-1-sulfonic acid [(R)-1-(5-benzo[1,3]dioxol-5-ylmethyl-2H-[1,2,4]triazol-3-yl)-3-phenyl-propyl]-amide | A |
| 31 | 3-Diethylamino-propane-1-sulfonic acid {(R)-1-[3-(2-chloro-pyridin-3-yl)-[1,2,4]oxadiazol-5-yl]-3-phenyl-propyl}-amide | A |
| 32 | 3-Diethylamino-propane-1-sulfonic acid {(R)-1-[5-(3,4-dimethoxy-benzyl)-2H-[1,2,4]triazol-3-yl]-3-phenyl-propyl}-amide | A |
| 33 | 3-Diethylamino-propane-1-sulfonic acid [(R)-2-benzyloxy-1-(3-o-tolyl-[1,2,4]oxadiazol-5-yl)-ethyl]-amide | D |
| 34 | 3-Diethylamino-propane-1-sulfonic acid {(R)-2-benzyloxy-1-[3-(3-methyl-pyridin-2-yl)-[1,2,4]oxadiazol-5-yl]-ethyl}-amide | C |
| 35 | 4-Diethylamino-cyclohexanesulfonic acid {(R)-1-[5-(4-fluoro-phenyl)-4H-[1,2,4]triazol-3-yl]-3-phenyl-propyl}-amide | B |
| 36 | 2-Diethylamino-ethanesulfonic acid {(R)-1-[3-(2,6-dimethyl-phenyl)-[1,2,4]oxadiazol-5-yl]-3-phenyl-propyl}-amide | D |
| 37 | 3-Diethylamino-propane-1-sulfonic acid {(R)-1-[3-(2,6-dimethoxy-phenyl)-[1,2,4]oxadiazol-5-yl]-3-phenyl-propyl}-amide | C |
| 38 | 3-Diethylamino-propane-1-sulfonic acid {(R)-1-[5-(1H-indol-3-yl)-2H-[1,2,4]triazol-3-yl]-3-phenyl-propyl}-amide | A |
| 39 | 3-Diethylamino-propane-1-sulfonic acid [(R)-3-phenyl-1-(3-pyridin-2-yl-[1,2,4]oxadiazol-5-yl)-propyl]-amide | C |
| 40 | 3-Diethylamino-propane-1-sulfonic acid {(R)-1-[5-(4-cyano-phenyl)-2H-[1,2,4]triazol-3-yl]-3-phenyl-propyl}-amide | A |
| 41 | 3-Diethylamino-propane-1-sulfonic acid [(R)-3-phenyl-1-(3-pyridin-3-yl-[1,2,4]oxadiazol-5-yl)-propyl]-amide | B |
| 42 | 3-Diethylamino-propane-1-sulfonic acid {(R)-1-[5-(4-tert-butyl-phenyl)-2H-[1,2,4]triazol-3-yl]-3-phenyl-propyl}-amide | D |
| 43 | 2-Diethylamino-ethanesulfonic acid [(R)-3-phenyl-1-(3-pyridin-3-yl-[1,2,4]oxadiazol-5-yl)-propyl]-amide | B |
| 44 | 3-Diethylamino-propane-1-sulfonic acid [(R)-1-(5-benzothiazol-6-yl-2H-[1,2,4]triazol-3-yl)-3-phenyl-propyl]-amide | A |
| 45 | 3-Diethylamino-propane-1-sulfonic acid [(R)-2-benzyloxy-1-(3-pyridin-3-yl-[1,2,4]oxadiazol-5-yl)-ethyl]-amide | D |
| 46 | 2-Diethylamino-ethanesulfonic acid {(R)-1-[3-(2,6-dimethoxy-phenyl)-[1,2,4]oxadiazol-5-yl]-3-phenyl-propyl}-amide | B |
| 47 | 3-Diethylamino-propane-1-sulfonic acid {(R)-1-[5-(2,3-dihydro-benzo[1,4]dioxin-6-yl)-2H-[1,2,4]triazol-3-yl]-3-phenyl-propyl}-amide | A |
| 48 | 3-Diethylamino-propane-1-sulfonic acid {(R)-1-[3-(2-chloro-phenyl)-[1,2,4]oxadiazol-5-yl]-3-phenyl-propyl}-amide | B |
| 49 | 2-Diethylamino-ethanesulfonic acid {(R)-2-benzyloxy-1-[3-(2-methoxy-phenyl)-[1,2,4]oxadiazol-5-yl]-ethyl}-amide | D |
| 50 | 3-Diethylamino-propane-1-sulfonic acid {(R)-1-[5-(3-cyano-phenyl)-2H-[1,2,4]triazol-3-yl]-3-phenyl-propyl}-amide | A |
| 51 | 3-Diethylamino-propane-1-sulfonic acid [(R)-2-benzyloxy-1-(3-pyridin-4-yl-[1,2,4]oxadiazol-5-yl)-ethyl]-amide | D |
| 52 | 3-Diethylamino-propane-1-sulfonic acid {(R)-1-[3-(2,6-dimethyl-phenyl)-[1,2,4]oxadiazol-5-yl]-3-phenyl-propyl}-amide | B |
| 53 | 3-Diethylamino-propane-1-sulfonic acid {(R)-1-[5-(3-bromo-phenyl)-2H-[1,2,4]triazol-3-yl]-3-phenyl-propyl}-amide | A |
| 54 | 2-Diethylamino-ethanesulfonic acid {(R)-1-[3-(2-chloro-pyridin-3-yl)-[1,2,4]oxadiazol-5-yl]-3-phenyl-propyl}-amide | B |
| 55 | 3-Diethylamino-propane-1-sulfonic acid [(R)-1-(3-benzo[1,3]dioxol-5-ylmethyl-[1,2,4]oxadiazol-5-yl)-3-phenyl-propyl]-amide | A |
| 56 | 3-Diethylamino-propane-1-sulfonic acid {(R)-1-[5-(3,4-difluoro-benzyl)-2H-[1,2,4]triazol-3-yl]-3-phenyl-propyl}-amide | B |
| 57 | 3-Diethylamino-propane-1-sulfonic acid {(R)-1-[3-(4-bromo-benzyl)-[1,2,4]oxadiazol-5-yl]-3-phenyl-propyl}-amide | A |
| 58 | 3-Diethylamino-propane-1-sulfonic acid {(R)-1-[5-(2,4-dichloro-phenyl)-2H-[1,2,4]triazol-3-yl]-3-phenyl-propyl}-amide | A |
| 59 | 3-Diethylamino-propane-1-sulfonic acid {(R)-1-[3-(4-bromo-phenyl)-[1,2,4]oxadiazol-5-yl]-3-phenyl-propyl}-amide | A |
| 60 | 3-Diethylamino-propane-1-sulfonic acid {(R)-1-[3-(2-methoxy-ethyl)-[1,2,4]oxadiazol-5-yl]-3-phenyl-propyl}-amide | C |
| 61 | 3-Diethylamino-propane-1-sulfonic acid [(R)-3-phenyl-1-(5-m-tolyl-2H-[1,2,4]triazol-3-yl)-propyl]-amide | A |
| 62 | 3-Diethylamino-propane-1-sulfonic acid {(R)-1-[3-(3-fluoro-benzyl)-[1,2,4]oxadiazol-5-yl]-3-phenyl-propyl}-amide | A |
| 63 | 3-Diethylamino-propane-1-sulfonic acid {(R)-1-[5-(2,5-difluoro-phenyl)-2H-[1,2,4]triazol-3-yl]-3-phenyl-propyl}-amide | B |
| 64 | 3-Diethylamino-propane-1-sulfonic acid {(R)-1-[3-(3-bromo-phenyl)-[1,2,4]oxadiazol-5-yl]-3-phenyl-propyl}-amide | A |
| 65 | 3-Diethylamino-propane-1-sulfonic acid {(R)-1-[5-(4-nitro-phenyl)-2H-[1,2,4]triazol-3-yl]-3-phenyl-propyl}-amide | A |
| 66 | 3-Diethylamino-propane-1-sulfonic acid {(R)-1-[3-(4-fluoro-phenyl)-[1,2,4]oxadiazol-5-yl]-3-phenyl-propyl}-amide | A |
| 67 | 3-Diethylamino-propane-1-sulfonic acid {(R)-1-[3-(4-bromo-2-methyl-phenyl)-[1,2,4]oxadiazol-5-yl]-3-phenyl-propyl}-amide | B |
| 68 | 3-Diethylamino-propane-1-sulfonic acid {(R)-1-[3-(2-methyl-benzyl)-[1,2,4]oxadiazol-5-yl]-3-phenyl-propyl}-amide | A |
| 69 | 3-Diethylamino-propane-1-sulfonic acid {(R)-1-[3-(4-methoxy-phenyl)-[1,2,4]oxadiazol-5-yl]-3-phenyl-propyl}-amide | A |
| 70 | 3-Diethylamino-propane-1-sulfonic acid {(R)-1-[5-(3-chloro-phenyl)-2H-[1,2,4]triazol-3-yl]-3-phenyl-propyl}-amide | A |
| 71 | 3-Diethylamino-propane-1-sulfonic acid [(R)-3-phenyl-1-(3-p-tolyl-[1,2,4]oxadiazol-5-yl)-propyl]-amide | A |
| 72 | 3-Diethylamino-propane-1-sulfonic acid {(R)-1-[3-(2-fluoro-benzyl)-[1,2,4]oxadiazol-5-yl]-3-phenyl-propyl}-amide | A |
| 73 | 3-Diethylamino-propane-1-sulfonic acid {(R)-1-[3-(2,6-dichloro-benzyl)-[1,2,4]oxadiazol-5-yl]-3-phenyl-propyl}-amide | A |

TABLE 1-continued
Exemplary GHS-R Modulating Compounds

| Number | Name | Activity* |
|---|---|---|
| 74 | 3-Diethylamino-propane-1-sulfonic acid {(R)-1-[3-(3-bromo-benzyl)-[1,2,4]oxadiazol-5-yl]-3-phenyl-propyl}-amide | A |
| 75 | 3-Diethylamino-propane-1-sulfonic acid {(R)-1-[3-(2-bromo-benzyl)-[1,2,4]oxadiazol-5-yl]-3-phenyl-propyl}-amide | A |
| 76 | 2-Diethylamino-ethanesulfonic acid {(R)-1-[3-(3-bromo-phenyl)-[1,2,4]oxadiazol-5-yl]-3-phenyl-propyl}-amide | D |
| 77 | 2-Diethylamino-ethanesulfonic acid {(R)-1-[3-(4-methyl-pyridin-3-yl)-[1,2,4]oxadiazol-5-yl]-3-phenyl-propyl}-amide | D |
| 78 | 2-Diethylamino-ethanesulfonic acid {(R)-1-[3-(2-methoxy-ethyl)-[1,2,4]oxadiazol-5-yl]-3-phenyl-propyl}-amide | C |
| 79 | 2-Diethylamino-ethanesulfonic acid {(R)-1-[3-(4-bromo-phenyl)-[1,2,4]oxadiazol-5-yl]-3-phenyl-propyl}-amide | B |
| 80 | 3-Diethylamino-propane-1-sulfonic acid {(R)-1-[5-(3,4-dimethoxy-phenyl)-2H-[1,2,4]triazol-3-yl]-3-phenyl-propyl}-amide | B |
| 81 | 2-Diethylamino-ethanesulfonic acid [(R)-1-(3-benzo[1,3]dioxol-5-ylmethyl-[1,2,4]oxadiazol-5-yl)-3-phenyl-propyl]-amide | B |
| 82 | 2-Diethylamino-ethanesulfonic acid {(R)-1-[3-(3-fluoro-benzyl)-[1,2,4]oxadiazol-5-yl]-3-phenyl-propyl}-amide | A |
| 83 | 3-Diethylamino-propane-1-sulfonic acid {(R)-1-[3-(4-methyl-pyridin-3-yl)-[1,2,4]oxadiazol-5-yl]-3-phenyl-propyl}-amide | B |
| 84 | 2-Diethylamino-ethanesulfonic acid {(R)-1-[3-(4-bromo-benzyl)-[1,2,4]oxadiazol-5-yl]-3-phenyl-propyl}-amide | B |
| 85 | 2-Diethylamino-ethanesulfonic acid {(R)-1-[3-(4-bromo-2-methyl-phenyl)-[1,2,4]oxadiazol-5-yl]-3-phenyl-propyl}-amide | D |
| 86 | 2-Diethylamino-ethanesulfonic acid [(R)-3-phenyl-1-(3-p-tolyl-[1,2,4]oxadiazol-5-yl)-propyl]-amide | B |
| 87 | 2-Diethylamino-ethanesulfonic acid {(R)-1-[3-(2-methyl-benzyl)-[1,2,4]oxadiazol-5-yl]-3-phenyl-propyl}-amide | B |
| 88 | 2-Diethylamino-ethanesulfonic acid {(R)-1-[3-(4-methoxy-phenyl)-[1,2,4]oxadiazol-5-yl]-3-phenyl-propyl}-amide | D |
| 89 | 2-Diethylamino-ethanesulfonic acid {(R)-1-[3-(4-fluoro-phenyl)-[1,2,4]oxadiazol-5-yl]-3-phenyl-propyl}-amide | A |
| 90 | 2-Diethylamino-ethanesulfonic acid {(R)-1-[3-(2,6-dichloro-benzyl)-[1,2,4]oxadiazol-5-yl]-3-phenyl-propyl}-amide | A |
| 91 | 2-Diethylamino-ethanesulfonic acid {(R)-1-[3-(2-fluoro-benzyl)-[1,2,4]oxadiazol-5-yl]-3-phenyl-propyl}-amide | B |
| 92 | 2-Diethylamino-ethanesulfonic acid {(R)-1-[3-(3-bromo-benzyl)-[1,2,4]oxadiazol-5-yl]-3-phenyl-propyl}-amide | A |
| 93 | 2-Diethylamino-ethanesulfonic acid {(R)-1-[3-(2-bromo-benzyl)-[1,2,4]oxadiazol-5-yl]-3-phenyl-propyl}-amide | A |
| 94 | 3-Diethylamino-propane-1-sulfonic acid {(R)-1-[5-(4-methoxy-phenyl)-2H-[1,2,4]triazol-3-yl]-3-phenyl-propyl}-amide | A |
| 95 | 3-Diethylamino-propane-1-sulfonic acid {(S)-1-[5-(4-methoxy-phenyl)-2H-[1,2,4]triazol-3-yl]-2-phenyl-ethyl}-amide | A |
| 96 | 3-Diethylamino-propane-1-sulfonic acid {(R)-1-[5-(2,4-difluoro-phenyl)-2H-[1,2,4]triazol-3-yl]-3-phenyl-propyl}-amide | A |
| 97 | 3-Diethylamino-propane-1-sulfonic acid [(R)-1-(3-phenethyl-[1,2,4]oxadiazol-5-yl)-3-phenyl-propyl]-amide | A |
| 98 | (R)-4-[3-(4-Bromo-benzyl)-[1,2,4]oxadiazol-5-yl]-4-(3-diethylamino-propane-1-sulfonylamino)-butyramide | B |
| 99 | 3-Diethylamino-propane-1-sulfonic acid [(R)-1-(3-phenoxymethyl-[1,2,4]oxadiazol-5-yl)-3-phenyl-propyl]-amide | A |
| 100 | 3-Diethylamino-propane-1-sulfonic acid {(R)-1-[3-(2-methoxy-benzyl)-[1,2,4]oxadiazol-5-yl]-3-phenyl-propyl}-amide | A |
| 101 | 3-Diethylamino-propane-1-sulfonic acid ((R)-1-{3-[2-(2-chloro-phenyl)-ethyl]-[1,2,4]oxadiazol-5-yl}-3-phenyl-propyl)-amide | B |
| 102 | (R)-3-[3-(4-Bromo-benzyl)-[1,2,4]oxadiazol-5-yl]-3-(3-diethylamino-propane-1-sulfonylamino)-propionamide | B |
| 103 | 3-Diethylamino-propane-1-sulfonic acid {(R)-1-[3-(5-bromo-pyridin-3-yl)-[1,2,4]oxadiazol-5-yl]-phenyl-propyl}-amide | B |
| 104 | 3-Diethylamino-propane-1-sulfonic acid [(R)-3-phenyl-1-(5-o-tolyl-2H-[1,2,4]triazol-3-yl)-propyl]-amide | A |
| 105 | 3-Diethylamino-propane-1-sulfonic acid {(R)-1-[5-(4-fluoro-phenyl)-2H-[1,2,4]triazol-3-yl]-3-phenyl-propyl}-amide | A |
| 106 | 3-Diethylamino-propane-1-sulfonic acid {(R)-3-phenyl-1-[5-(4-trifluoromethoxy-phenyl)-2H-[1,2,4]triazol-3-yl]-propyl}-amide | A |
| 107 | 3-Diethylamino-propane-1-sulfonic acid {(R)-1-[5-(4-methoxy-benzyl)-2H-[1,2,4]triazol-3-yl]-3-phenyl-propyl}-amide | B |
| 108 | 3-Diethylamino-propane-1-sulfonic acid [(R)-3-phenyl-1-(5-p-tolyl-2H-[1,2,4]triazol-3-yl)-propyl]-amide | B |
| 109 | 3-Diethylamino-propane-1-sulfonic acid {(R)-1-[3-(3-methoxy-benzyl)-[1,2,4]oxadiazol-5-yl]-3-phenyl-propyl}-amide | A |
| 110 | 3-Diethylamino-propane-1-sulfonic acid {(R)-1-[5-(4-dimethylamino-phenyl)-2H-[1,2,4]triazol-3-yl]-3-phenyl-propyl}-amide | D |
| 111 | 3-Diethylamino-propane-1-sulfonic acid {(R)-1-[3-(4-methoxy-benzyl)-[1,2,4]oxadiazol-5-yl]-3-phenyl-propyl}-amide | A |
| 112 | 3-Diethylamino-propane-1-sulfonic acid [(R)-3-phenyl-1-(3-pyridin-2-ylmethyl-[1,2,4]oxadiazol-5-yl)-propyl]-amide | B |
| 113 | 3-Diethylamino-propane-1-sulfonic acid ((R)-1-{3-[2-(4-bromo-phenyl)-ethyl]-[1,2,4]oxadiazol-5-yl}-3-phenyl-propyl)-amide | A |
| 114 | 3-Diethylamino-propane-1-sulfonic acid {(R)-1-[3-(2-chloro-benzyl)-[1,2,4]oxadiazol-5-yl]-3-phenyl-propy}-amide | A |
| 115 | 3-Diethylamino-propane-1-sulfonic acid {(R)-1-[5-(2-fluoro-4-methoxy-phenyl)-2H-[1,2,4]triazol-3-yl]-3-phenyl-propyl}-amide | A |
| 116 | 3-Diethylamino-propane-1-sulfonic acid [(R)-1-(3-benzyl-[1,2,4]oxadiazol-5-yl)-3-phenyl-propyl]-amide | B |
| 117 | 3-Diethylamino-propane-1-sulfonic acid {(R)-3-phenyl-1-[3-(4-trifluoromethyl-benzyl)-[1,2,4]oxadiazol-5-yl]-propyl}-amide | A |
| 118 | 3-Diethylamino-propane-1-sulfonic acid {(R)-1-[5-(1H-indol-4-yl)-2H-[1,2,4]triazol-3-yl]-3-phenyl-propyl}-amide | A |
| 119 | 3-Diethylamino-propane-1-sulfonic acid {(R)-1-[5-(4-methoxy-phenyl)-2H-[1,2,4]triazol-3-yl]-2-phenyl-ethyl}-amide | B |
| 120 | 3-Diethylamino-propane-1-sulfonic acid {(R)-1-[5-(4-hydroxy-phenyl)-2H-[1,2,4]triazol-3-yl]-3-phenyl-propyl}-amide | A |
| 121 | 3-Diethylamino-propane-1-sulfonic acid {(R)-1-[5-(3-hydroxy-phenyl)-2H-[1,2,4]triazol-3-yl]-3-phenyl-propyl}-amide | A |
| 122 | 3-Diethylamino-propane-1-sulfonic acid [(R)-3-phenyl-1-(5-thiophen-3-ylmethyl-2H-[1,2,4]triazol-3-yl)-propyl]-amide | A |
| 123 | 3-Diethylamino-propane-1-sulfonic acid {(R)-1-[5-(3-methylsulfanyl-phenyl)-2H-[1,2,4]triazol-3-yl]-3-phenyl-propyl}-amide | A |
| 124 | 3-Diethylamino-propane-1-sulfonic acid [(R)-1-(5-benzotriazol-1-ylmethyl-2H-[1,2,4]triazol-3-yl)-3-phenyl-propyl]-amide | A |
| 125 | 3-Diethylamino-propane-1-sulfonic acid {(R)-1-[5-(3-cyano-4-methoxy-phenyl)-2H-[1,2,4]triazol-3-yl]-3-phenyl-propyl}-amide | A |
| 126 | 3-Diethylamino-propane-1-sulfonic acid {(R)-1-[5-(3-chloro-4-cyano-phenyl)-2H-[1,2,4]triazol-3-yl]-3-phenyl-propyl}-amide | A |
| 127 | 3-Diethylamino-propane-1-sulfonic acid {(R)-1-[5-(1H-indol-3-ylmethyl)-2H-[1,2,4]triazol-3-yl]-3phenyl-propyl}-amide | A |
| 128 | 3-Diethylamino-propane-1-sulfonic acid {(R)-1-[5-(3-cyano-4-fluoro-phenyl)-2H-[1,2,4]triazol-3-yl]-3-phenyl-propyl}-amide | A |

TABLE 1-continued

Exemplary GHS-R Modulating Compounds

| Number | Name | Activity* |
|---|---|---|
| 129 | 3-Diethylamino-propane-1-sulfonic acid [(R)-1-(5-benzo[b]thiophen-5-yl-2H-[1,2,4]triazol-3-yl)-3-phenyl-propyl]-amide | A |
| 130 | 3-Diethylamino-propane-1-sulfonic acid [(R)-1-(5-benzofuran-5-yl-2H-[1,2,4]triazol-3-yl)-3-phenyl-propyl]-amide | A |
| 131 | 3-Diethylamino-propane-1-sulfonic acid {(R)-1-[5-(1-methyl-1H-imidazol-4-yl)-2H-[1,2,4]triazol-3-yl]-3-phenyl-propyl}-amide | A |
| 132 | 3-Diethylamino-propane-1-sulfonic acid {(R)-1-[5-(3,5-difluoro-benzyl)-2H-[1,2,4]triazol-3-yl]-3-phenyl-propyl}-amide | A |
| 133 | 3-Diethylamino-propane-1-sulfonic acid {(R)-1-[5-(4-methyl-3H-1lambda*4*-thiazol-2-ylmethyl)-2H-[1,2,4]triazol-3-yl]-3-phenyl-propyl}-amide | A |
| 134 | 3-Diethylamino-propane-1-sulfonic acid {(R)-1-[5-(1H-imidazo[1,2,-a]pyridin-6-yl)-2H-[1,2,4]triazol-3-yl]-3-phenyl-propyl}-amide | B |
| 135 | 3-Diethylamino-propane-1-sulfonic acid {(R)-1-[5-(3-methyl-3H-imidazol-4-yl)-2H-[1,2,4]triazol-3-phenyl-propyl}-amide | A |
| 136 | 3-Diethylamino-propane-1-sulfonic acid {(R)-1-[5-(3,4-dihydro-2H-benzo[1,4]oxazin-2-yl)-2H-[1,2,4]triazol-3-yl]-3-phenyl-propyl}-amide | A |
| 137 | 3-Diethylamino-propane-1-sulfonic acid {(R)-1-[5-(2-methyl-thiazol-4-yl)-2H-[1,2,4]triazol-3-yl]-3-phenyl-propyl}-amide | A |
| 138 | 3-Diethylamino-propane-1-sulfonic acid {(R)-1-[5-(6-methoxy-pyridin-3-yl)-2H-[1,2,4]triazol-3-yl]-3-phenyl-propyl}-amide | A |
| 139 | 3-Diethylamino-propane-1-sulfonic acid [(R)-1-(5-cyclohexyl-2H-[1,2,4]triazol-3-yl)-3-phenyl-propyl]-amide | A |
| 140 | (R)-4-[3-(4-Bromo-benzyl)-[1,2,4]oxadiazol-5-yl]-4-(3-diethylamino-propane-1-sulfonylamino)-butyramide | B |
| 141 | (R)-3-[3-(4-Bromo-benzyl)-[1,2,4]oxadiazol-5-yl]-3-(3-diethylamino-propane-1-sulfonylamino)-propionamide | B |
| 142 | (S)-(3-{2-[3-(4-Bromo-benzyl)-[1,2,4]oxadiazol-5-yl]-pyrrolidine-1-sulfonyl}-propyl)-diethyl-amine | B |
| 143 | (S)-Diethyl-(3-{2-[3-(4-methoxy-phenyl)-[1,2,4]oxadiazol-5-yl]-pyrrolidine-1-sulfonyl}-propyl)-amine | B |
| 144 | (R)-Diethyl-(3-{2-[3-(4-methoxy-phenyl)-[1,2,4]oxadiazol-5-yl]-pyrrolidine-1-sulfonyl}-propyl)-amine | B |
| 145 | (R)-(3-{2-[3-(4-Bromo-benzyl)-[1,2,4]oxadiazol-5-yl]-pyrrolidine-1-sulfonyl}-propyl)-diethyl-amine | B |
| 146 | (S)-3-Diethylamino-propane-1-sulfonic acid {1-[3-(4-bromo-benzyl)-[1,2,4]oxadiazol-5-yl]-ethyl}-amide | B |
| 147 | (R)-3-Diethylamino-propane-1-sulfonic acid {1-[3-(4-bromo-benzyl)-[1,2,4]oxadiazol-5-yl]-ethyl}-amide | B |
| 148 | 3-Diethylamino-propane-1-sulfonic acid [3-(4-methoxy-phenyl)-[1,2,4]oxadiazol-5-ylmethyl]-amide | C |
| 149 | (S)-(3-{2-[3-(4-Bromo-benzyl)-[1,2,4]oxadiazol-5-yl]-azetidine-1-sulfonyl}-propyl)-diethyl-amine | A |
| 150 | (S)-3-Diethylamino-propane-1-sulfonic acid {1-[3-(4-methoxy-phenyl)-[1,2,4]oxadiazol-5-yl]-ethyl}-amide | B |
| 151 | 3-Diethylamino-propane-1-sulfonic acid [3-(4-bromo-benzyl)-[1,2,4]oxadiazol-5-ylmethyl]-amide | B |
| 152 | (R)-3-Diethylamino-propane-1-sulfonic acid {1-[3-(4-methoxy-phenyl)-[1,2,4]oxadiazol-5-yl]-ethyl}-amide | B |
| 153 | (S)-Diethyl-(3-{2-[3-(4-methoxy-phenyl)-[1,2,4]oxadiazol-5-yl]-azetidine-1-sulfonyl}-propyl)-amine | A |
| 154 | 3-Diethylamino-propane-1-sulfonic acid {1-[3-(4-bromo-benzyl)-[1,2,4]oxadiazol-5-yl]-1-methyl-ethyl}-amide | A |
| 155 | 3-Diethylamino-propane-1-sulfonic acid {1-[3-(4-methoxy-phenyl)-[1,2,4]oxadiazol-5-yl]-1-methyl-ethyl}-amide | B |
| 156 | 3-Diethylamino-propane-1-sulfonic acid [5-(4-methoxy-phenyl)-2H-[1,2,4]triazol-3-ylmethyl]-amide | B |
| 157 | 3-Diethylamino-propane-1-sulfonic acid [5-(4-chloro-benzyl)-2H-[1,2,4]triazol-3-ylmethyl]-amide | B |
| 158 | 3-Diethylamino-propane-1-sulfonic acid [3-(4-fluoro-phenyl)-[1,2,4]oxadiazol-5-ylmethyl]-amide | E |
| 159 | (S)-3-Diethylamino-propane-1-sulfonic acid {1-[5-(4-methoxy-phenyl)-2H-[1,2,4]triazol-3-yl]-3-methyl-butyl}-amide | B |
| 160 | (R)-3-Diethylamino-propane-1-sulfonic acid {1-[5-(4-methoxy-phenyl)-2H-[1,2,4]triazol-3-yl]-3-methyl-butyl}-amide | B |

*A refers to a compound having antagonist activity with a Ki <100 nM in a cell based assay.

B refers to a compound having antagonist activity with a Ki between 100 nM and 500 nM in a cell based assay.

C refers to a compound having antagonist activity with a Ki between 500 nM and 1000 nM in a cell based assay.

D refers to a compound having antagonist activity with Ki, ≦1000 nM in a cell-based assay.

E refers to other exemplary compounds.

Representative compounds that modulate GHS-R include the compounds of formulas (I), (II), (III), (IV), (V), and (VI) below, where all variables are as described herein.

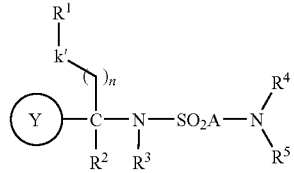

formula (I)

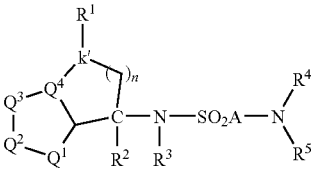

formula (II)

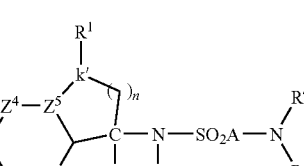

formula (III)

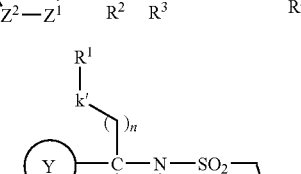

formula (IV)

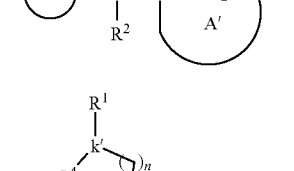

formula (V)

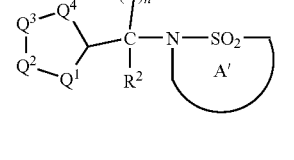

formula (VI)

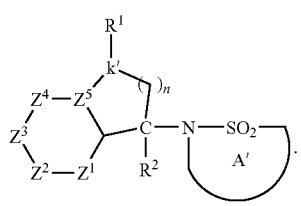

In some preferred embodiments, Y is a 5 membered heteroaromatic moiety substituted with 1 or 2 substituents as described herein. Exemplary Y moieties are reproduced below.

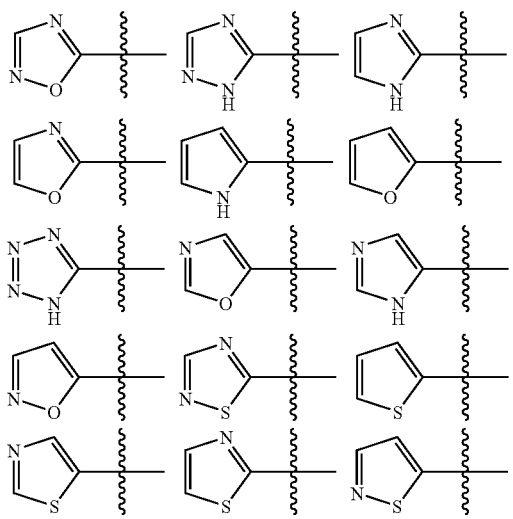

In each instance, any atom, including the hydrogens depicted on the nitrogen atoms, can be substituted with $R^{10}$. In some preferred embodiments, the heteroaryl moiety includes 1 or 2 $R^{10}$ substituents. In some preferred embodiments, $R^{10}$ is aryl, arylalkyl, or $R^{15}$. When two $R^{10}$ substituents are included, in some embodiments, one $R^{10}$ is $R^{15}$ and the second $R^{10}$ is a different substituent, such as alkyl, alkoxy, halo, etc.

In certain instances, $R^1$ is an aryl moietiy such as a phenyl moiety, for example unsubstituted or substituted aryl moiety. In some instances, $R^1$ is a heteroaryl moiety such as an indole moiety. In many instances where $R^1$ is aryl or heteroaryl (or other lipophilic moiety such as alkyl), K is an oxygen or a bond.

A and $R^4$ and $R^5$ can be chosen to vary the compound's type of interaction with GHS-R. For example, in some instances where $R^4$ and $R^5$ are both hydrogen, the compound is an agonist of GHS-R. In other instances where $R^4$ and $R^5$ are both independently alkyl, the compound is an antagonist of GHS-R.

Other aspects of this invention relate to a composition having a compound of any of the formulae described herein and a pharmaceutically acceptable carrier; or a compound of any of the formulae described herein, an additional therapeutic compound (e.g., an anti-hypertensive compound or a cholesterol lowering compound), and a pharmaceutically acceptable carrier; or a compound of any of the formulae described herein, an additional therapeutic compound, and a pharmaceutically acceptable carrier.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Synthesis of Ghrelin Receptor-Modulating Compounds

The compounds described herein can be made using a variety of synthetic techniques.

In some embodiments, a Y moiety, or other ring corresponding to a Y moiety, can be synthesized onto an amino acid or amino acid type starting material as depicted in schemes A and B and B' below.

Scheme A

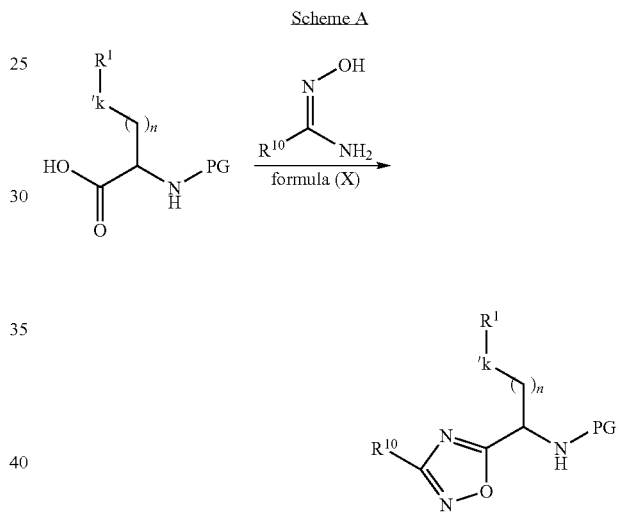

In the schemes provided herein, all variables are defined as herein and PG is a nitrogen protecting group. The nitrogen protected amino acid is reacted with a N-hydroxy imidamide (amidoxime) moiety (which is prepared by reacting a cyano containing moiety with hydroxylamine) to produce an oxadiazole containing moiety. The resulting compound can be further manipulated to form a compound of formula (I) by removing the nitrogen protecting group and reacting the resulting moiety with an activated sulfone, such as a sulfonyl chloride as depicted below.

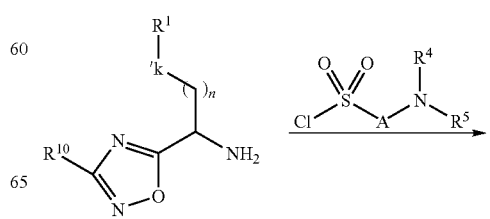

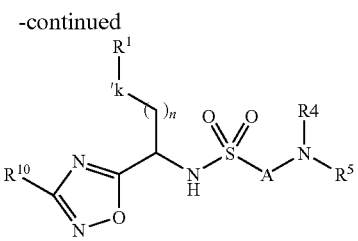

Scheme B below depicts the formation of a triazole containing moiety which can be further reacted in a manner similar to the oxadiazole containing moiety to form a compound of formula (I).

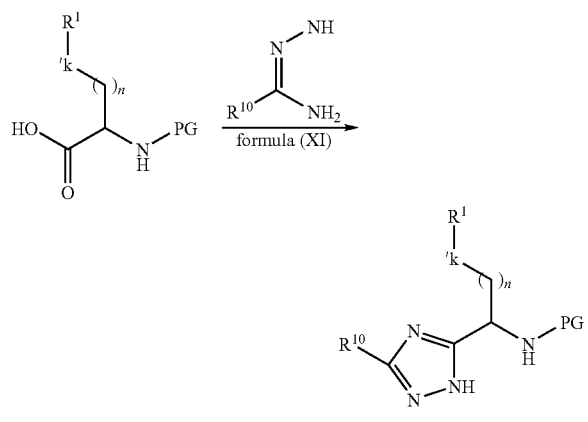

Scheme B' below depicts an alternative method of forming a triazole containing moiety which can be further reacted in a manner similar to the oxadiazole containing moiety to form a compound of formula (I).

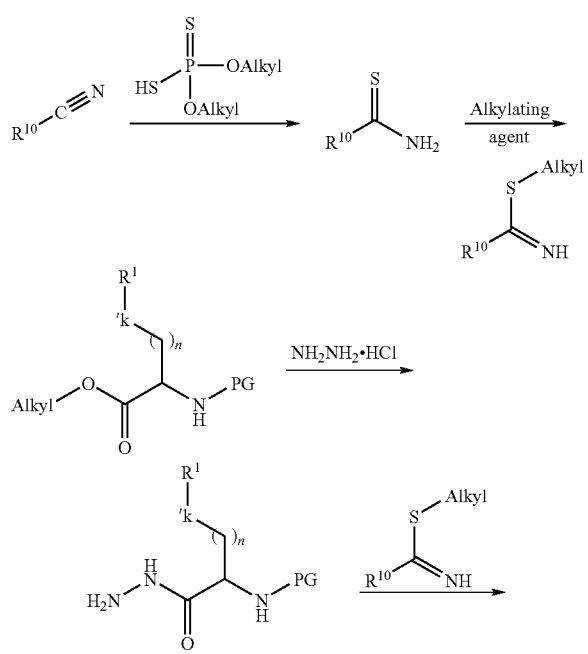

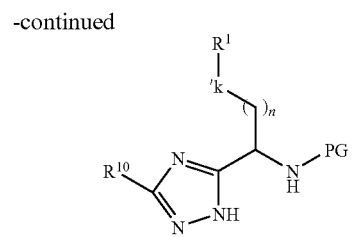

The triazole precursor moiety can be prepared in a variety of manners, for example, by reacting a cyano containing moiety with a hydrazine hydrate (to form the intermediate amidrazone) as depicted in scheme B. Alternatively, the triazole precursor moiety can be prepared as shown in scheme B' by reacting a nitrile moiety (e.g., an arylnitrile or benzylnitrile) with a dialkyl dithiophosphate moiety such as diethyl dithiophosphate to provide an thioimidate, which is reacted with a acyl hydrazide moiety to provide the triazole precursor. The acyl hydrazide moiety can be prepared, for example, by reacting a carboxylic acid or derivative thereof with hydrazine.

In other embodiments, a compound of formula (I) can be prepared by first reacting an activated sulfone moiety (e.g., a sulfonyl chloride) with an amino acid moiety or protected amino acid, as depicted in Scheme C below.

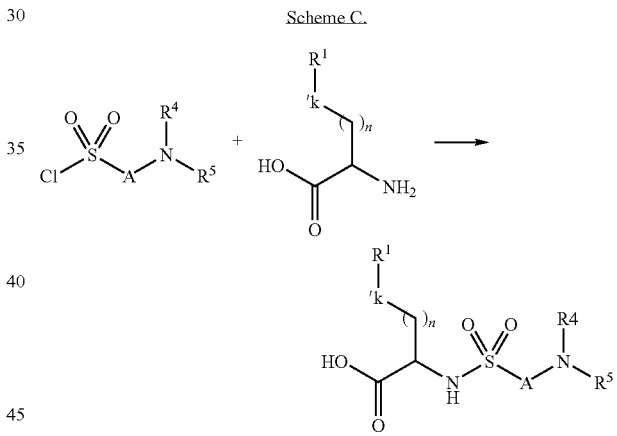

The free carboxyl moiety can then be further manipulated to produce a compound of formula (I). For example, the free carboxyl moiety can be reacted with a compound of formula (X) or (XI) above to form an oxadiazole or triazole containing compound of formula (I) in a manner similar to that described in schemes A, B and B' above.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L.

Paquette, ed., *Encyclopedia of Reagents for Organic Synthesis*, John Wiley and Sons (1995), and subsequent editions thereof. Additionally, the compounds disclosed herein can be prepared on a solid support or using a solid phase peptide synthesis.

The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, poly-acrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998), and include those useful in techniques such as the "split and pool" or "parallel" synthesis techniques, solid-phase and solution-phase techniques, and encoding techniques (see, for example, Czarnik, A. W., *Curr. Opin. Chem. Bio.*, (1997) 1, 60).

The term "solid phase peptide" refers to an amino acid, which is chemically bonded to a resin (e.g., a solid support). Resins are generally commercially available (e.g., from SigmaAldrich). Some examples of resins include Rink-resins. Tentagel S RAM, MBHA, and BHA-resins.

The compounds of this invention may contain one or more asymmetric centers and thus occur as racemates and racemic mixtures, single enantiomers and enantiometric mixtures, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention (for example an imidate ester of an amide), which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undeconoate. Salts derived from appropriate bases include alkali metal (e.g., sodium), alkaline earth metal (e.g., magnesium), ammonium and $N-(alkyl)_4^+$ salts. This invention also envisions the quaternization of any basic nitrogen-containing groups of the compounds disclosed herein. Water or oil-soluble or dispersible products may be obtained by such quaternization.

Evaluating Compounds

A variety of methods can be used to evaluate a compound for ability to modulate GHS-R activity. Evaluation methods include in vitro binding assays, in vitro cell-based signaling assay, and in vivo methods. The evaluation methods can evaluate binding activity, or an activity downstream of GHS-R, e.g., a signaling activity downstream of GHS-R such as inositol phosphate production, $Ca^{2+}$ mobilization, or gene transcription (e.g., CREB-mediated gene transcription).

Binding Assays. Generally, the compounds can be evaluated to determine if they bind to GHS-R and if they compete with one or more known compounds that interact with GHS-R, and the extent of such interactions. For example, the compounds can be evaluated to determine if they compete with ghrelin, ipamorelin, L-692,400 or L-692,492.

One exemplary binding assay is as follows: GHS-R expressing COS-7 cells cultured at a density of $1 \times 10^5$ cells per well so that binding is assayed in the range of about 5-8% binding of the radioactive ligand. For example, the cells can express an endogenous nucleic acid encoding GHS-R or an exogenous nucleic acid encoding GHS-R. Cells transfected with an exogenous nucleic acid encoding GHS-R can be used, e.g., two days, after transfection. Competition binding experiments are performed for 3 hours at 4° C. using 25 pM of $^{125}$I-ghrelin in 0.5 ml of 50 mM HEPES buffer, pH 7.4, supplemented with 1 mM $CaCl_2$, 5 mM $MgCl^2$, and 0.1% (w/v) bovine serum albumin, 40 mg/ml bacitracin. Non-specific binding can be determined as the binding in the presence of 1 mM of unlabeled ghrelin. Cells are washed twice in 0.5 ml of ice-cold buffer and then lysed with 0.5-1 ml of lysis buffer (8 M Urea, 2% NP40 in 3 M acetic acid). After washing and lysis, the bound radioactivity is counted. Assays can be run in duplicate or triplicate, e.g., to provide statistical power.

Values of the dissociation and inhibition constants ($K_d$ and $K_i$) can be estimated from competition binding experiments using the equation:

$$K_d = IC_{50} - L \text{ and } K_i = IC_{50}/(1 + L/K_d),$$

where L is the concentration of radioactive ligand. $B_{max}$ values can be estimated from competition binding experiments using the equation $$B_{max} = B_0 IC_{50}/[\text{ligand}],$$

where $B_0$ is the specifically bound radioligand.

Cell-Based Activity Assays. For example, the ability of the compound to modulate accumulation of a second messenger signaling component downstream of GHS-R can be evaluated. For example, inositol phosphates (IP), as a result of Gq signaling in a mammalian cell, e.g., a Cos-7 cells. Other tissue culture cells, Xenopus oocytes, and primary cells can also be used.

Phosphatidylinositol turnover assay. One day after transfection COS-7 cells are incubated for 24 hours with 5 µCi of [$^3$H]-myo-inositol in 1 ml medium supplemented with 10% fetal calf serum, 2 mM glutamine and 0.01 mg/ml gentamicin per well. Cells are then washed twice in buffer, 20 mM HEPES, pH 7.4, supplemented with 140 mM NaCl, 5 mM KCl, 1 mM $MgSO_4$, 1 mM $CaCl_2$, 10 mM glucose, 0.05% (w/v) bovine serum; and incubated in 0.5 ml buffer supplemented with 10 mM LiCl at 37° C. for 30 min. For some assays, it is also useful to incubate the cells with adenosine deaminase ADA (200 U/mg, Boehringer Mannheim, Germany) for 30 min in a concentration of 1 U/ml.

After incubation with the compound of interest for 45 min at 37° C., cells are extracted with 10% ice-cold perchloric acid and placed on ice for 30 min. The resulting supernatants are neutralized with KOH in HEPES buffer, and [$^3$H]-inositol phosphate is purified on Bio-Rad AG 1-X8 anion exchange resin as described. Assays can be run in duplicate, triplicate, etc.

Other second messenger assays. Another second messenger that can be evaluated is $Ca^{2+}$. $Ca^{2+}$ mobilization can be evaluated using a calcium sensitive detector, such as aequorin protein or a dye, e.g., FURA-2. In an exemplary assay, calcium mobilization is evaluated in a recombinant cell that expresses GHS-R and aequorin.

Gene expression assay. HEK293 cells (30,000 cells/well) seeded in 96-well plates are transiently transfected with a mixture of pFA2-CREB and pFR-Luc reporter plasmid (PathDetect™ CREB trans-Reporting System, Stratagene) and nucleic acid encoding GHS. One day after transfection, cells are treated with the compound of interest in an assay volume of 100 µl medium for 5 hrs. After treatment, cells are cultured in low serum (2.5%). After the incubation period, the assay is ended by washing the cells twice with PBS and adding 100 µl luciferase assay reagent (LucLite™, Packard Bioscience). Luminescence is measured (e.g., as relative light units (RLU)) using in a luminometer such as the TopCounter™ (Packard Bioscience) for 5 sec.

Other transcription based assays can include evaluating transcription of GHS-R regulated genes in primary cells that express GHS-R (e.g., cells from pituitary, brain, spinal cord, uterus, spleen, pancreas, kidney, adrenal gland, skeletal muscle, thyroid, liver, small intestine, and heart) or in recombinant cells that express GHS-R. mRNA levels can be evaluated by any method, e.g., microarray analysis, Northern blotting, or RT-PCR. Exemplary genes that are directly or indirectly regulated by GHS-R activity include leptin, resistin, and adiponectin. GHS-R activity may also affect insulin, IGF-1, and leptin levels in circulation.

$IC_{50}$ and $EC_{50}$ values can be determined by nonlinear regression, e.g., using the Prism 3.0 software (GraphPad Software, San Diego).

In vivo assays. Exemplary in vivo assays include the fast-refeeding assay described in Example 1 and as follows.

Prior to compound administration, mice are weighed and sorted into groups based on comparable body weight. Food is removed at 6 pm for an overnight (~16 hour) fast. Beginning at 10 am on the next morning, mice are administered with either vehicle (e.g., saline+acetic acid, pH=5) or the compound of interest. Mice are then returned to their home cages and pre-weighed food (approximately 90 grams) is immediately returned to the food hoppers in each cage. The weight of the food remaining in the food hoppers is measured at 30 minutes, 1 hour, 2 hours, and 4 hours post compound/vehicle administration. Final body weights are then recorded for the mice.

The compound of interest can also be evaluated in other experiments. For example, the compound can be administered to lean or obese mice (e.g., (ob/ob) C57BL/6J mice), or other experimental animals. The compound can be administered intraperitoneally or intracerebroventricularly. After administration, the animal is evaluated, e.g., for feeding behavior, anxiety, or one or more physiological parameters, e.g., a metabolic parameter.

ICV Administration. For intra-third cerebroventricular (ICV) administration, each drug can be diluted in 4 µl of artificial cerebrospinal fluid for injection. For ICV injection, mice are anaesthetised with sodium pentobarbital (80-85 mg/kg intraperitoneally) and placed in a stereotaxic instrument seven days before the experiments. A hole is made in each skull using a needle inserted 0.9 mm lateral to the central suture and 0.9 mm posterior to the bregma. A 24 gauge cannula bevelled at one end over a distance of 3 mm is implanted into the third cerebral ventricle for ICV injection.

Gastric emptying assessment. Another test for food consumption after administration of a compound of interest is the gastric emptying assessment. Before the gastric emptying assessment, mice are food deprived for 16 hours with free access to water. Fasted mice are given free access to pre-weighed pellets for one hour and then administered the compound of interest. The mice are again deprived of food for one or two hours after the compound administration. Food intake is measured by weighing uneaten pellets. Mice are killed by cervical dislocation two or three hours after the compound administration. Immediately after the stomach was exposed by laparotomy, quickly ligated at both the pylorus and cardia, removed, and the dry content is weighed. Gastric emptying is calculated according to the following formula:

gastric emptying (%)=(1−(dry weight of food recovered from the stomach/weight of food intake))× 100.

Anxiety tests. Anxiety can be assessed in the standard elevated plus maze, 50 cm above the ground. The four arms can be made 27 cm long and 6 cm wide. Two opposing arms are enclosed by walls 15 cm high (closed arms) while the other arms are devoid of walls (open arms). Each mouse is placed in the center of the maze facing one of the enclosed arms 10 minutes after injection with a compound. The cumulative time spent in each arm and the number of entries into the open or closed arms is recorded during a five minute test session. The time spent in the open arms is expressed as a percentage of total entry time (100-open)/open+closed) and the number of entries in the open arms is expressed as a percentage of the total number of entries (100-open/total entries).

Parameter analysis. Mice or other animals provided with the test compound can be analyzed for one or more biological parameters, e.g., metabolic parameters. For mice, serum is obtained from blood from the orbital sinus under ether anaesthesia at the end of a treatment (e.g., eight hours after removal of food and the final intraperitoneal injection). Mice are killed by cervical dislocation. Immediately after, the epididymal fat pad mass can be assessed based on removal and weighing of the white adipose tissue (WAT) and the gastrocnemius muscle. Blood glucose can be measured by the glucose oxidase method. Serum insulin and free fatty acids (FFA) can be measured by enzyme immunoassay and an enzymatic method (Eiken Chemical Co., Ltd, Tokyo, Japan), respectively. Serum triglycerides and total cholesterol can be measured by an enzymatic method (Wako Pure Chemical Industries, Ltd, Tokyo, Japan).

mRNA analysis. RNA is isolated from the stomach, epididymal fat or other relevant tissues using the RNeasy Mini Kit (Qiagen, Tokyo, Japan). Total RNA is denatured with formaldehyde, electrophoresed in 1% agrose gel, and blotted onto a Hybond N+membrane. The membranes are hybridized with a labeled cDNA probe (e.g., radioactively, chemically, or fluorescently labeled) for the gene of interest. The total integrated densities of hybridization signals can be determined by densitometry. Data can be normalized to a glyceraldehyde 3-phosphate dehydrogenase mRNA abundance or to actin mRNA abundance and expressed as a percentage of controls. Exemplary genes that can be evaluated include ghrelin, leptin, resistin, and adiponectin. It is also possible to use a transgenic animal that includes a reporter construct with a regulatory region from the gene of interest or to use a recombinant cell with such a construct.

A compound described herein can have a $K_i$ (as an antagonist) of less than 200, 100, 80, 70, 60, or 50 nM, in one or more of the described assays. A compound described herein can have a $K_D$ as an agonist of greater than 20, 40, 50, 100, 200, 300, or 500 nM, in one or more of the described assays.

A compound described herein can also specifically interact with GHS-R, e.g., relative to other cell surface receptors. The motilin receptor, for example, is a homolog of GHS-R. A disclosed compound may preferentially interact with GHS-R relative to the motilin receptor, e.g., at least a 2, 5, 10, 20, 50, or 100 preference. In another embodiment, the disclosed compound may also interact with motilin receptor, and, e.g., alter motilin receptor activity.

In one embodiment, the compound may alter an intracellular signaling activity downstream of GHS-R, e.g., Gq signaling, phospholipase C signaling, and cAMP response element (CRE) driven gene transcription.

Compounds may also be evaluated for their therapeutic activity with respect to any disorder, e.g., a disorder described herein. Animal models for many disorders are well known in the art.

Cells and animals for evaluating the effect of a compound on ALS status include a mouse which has an altered SOD gene, e.g., a SOD1-G93A transgenic mouse which carries a variable number of copies of the human G93A SOD mutation driven by the endogenous promoter, a SOD1-G37R transgenic mouse (Wong et al., Neuron, 14(6):1105-16 (1995)); SOD1-G85R transgenic mouse (Bruijn et al., Neuron, 18(2): 327-38 (1997)); *C. elegans* strains expressing mutant human SOD1 (Oeda et al., Hum Mol Genet., 10:2013-23 (2001)); and a *Drosophila* expressing mutations in Cu/Zn superoxide dismutase (SOD). (Phillips et al., Proc. Natl. Acad. Sci. U.S.A., 92:8574-78 (1995) and McCabe, Proc. Natl. Acad. Sci. U.S.A., 92:8533-34 (1995)).

Cells and animals for evaluating the effect of a compound on Alzheimer's disease are described, e.g., in U.S. Pat. No. 6,509,515 and U.S. Pat. Nos. 5,387,742; 5,877,399; 6,358, 752; and 6,187,992. In U.S. Pat. No. 6,509,515, the animal expresses an amyloid precursor protein (APP) sequence at a level in brain tissues such that the animal develops a progressive neurologic disorder. An exemplary animal model for evaluating polyglutamine-based aggregation is the transgenic mouse strain is the R6/2 line (Mangiarini et al. Cell 87:493-506(1996)). Models for evaluating the effect of a test compound on muscle atrophy include, e.g.: 1) rat medial gastrocnemius muscle mass loss resulting from denervation, e.g., by severing the right sciatic nerve at mid-thigh; 2) rat medial gastrocnemius muscle mass loss resulting from immobilization, e.g., by fixed the right ankle joint at 90 degrees of flexion; 3) rat medial gastrocnemius muscle mass loss resulting from hindlimb suspension; (see, e.g., U.S. 2003-0129686); 4)skeletal muscle atrophy resulting from treatment with the cachectic cytokine, interleukin-1 (IL-1) (R. N. Cooney, S. R. Kimball, T. C. Vary, Shock 7, 1-16 (1997)); and 5) skeletal muscle atrophy resulting from treatment with the glucocorticoid, dexamethasone (A. L. Goldberg, J Biol Chem 244, 3223-9 (1969).). Models 1, 2, and 3 induce muscle atrophy by altering the neural activity and/or external load a muscle experiences to various degrees. Models 4 and 5 induce atrophy without directly affecting those parameters.

Exemplary animal models for AMD (age-related macular degeneration) include: laser-induced mouse model simulating exudative (wet) macular degeneration Bora et al., Proc. Natl. Acad. Sci. U S A., 100:2679-84 (2003); a transgenic mouse expressing a mutated form of cathepsin D resulting in features associated with the "geographic atrophy" form of AMD (Rakoczy et al., Am. J. Pathol., 161;1515-24 (2002)); and a transgenic mouse overexpressing VEGF in the retinal pigment epithelium resulting in CNV. Schwesinger et al., Am. J. Pathol. 158:1161-72 (2001).

Exemplary animal models of Parkinson's disease include primates rendered parkinsonian by treatment with the dopaminergic neurotoxin 1-methyl-4 phenyl 1,2,3,6-tetrahydropyridine (MPTP) (see, e.g., U.S. application 20030055231 and Wichmann et al., Ann. N.Y. Acad. Sci., 991:199-213 (2003); 6-hydroxydopamine-lesioned rats (e.g., Lab. Anim. Sci., 49:363-71 (1999)); and transgenic invertebrate models (e.g., Lakso et al., J. Neurochem., 86:165-72 (2003) and Link, Mech. Ageing Dev., 122:1639-49 (2001)). Exemplary molecular models of Type II diabetes include: a transgenic mouse having defective Nkx-2.2 or Nkx-6.1; (U.S. Pat. No. 6,127,598); Zucker Diabetic Fatty fa/fa (DZF) rat. (U.S. Pat. No. 6,569,832); and Rhesus monkeys, which spontaneously develop obesity and subsequently frequently progress to overt type 2 diabetes (Hotta et al., Diabetes, 50:1126-33 (2001); and a transgenic mouse with a dominant-negative IGF-I receptor (KR-IGF-IR) having Type 2 diabetes-like insulin resistance.

Exemplary animal and cellular models for neuropathy include: vincristine induced sensory-motor neuropathy in mice (U.S. patent application Ser. No. 5,420,112) or rabbits (Ogawa et al., Neurotoxicology, 21:501-11 (2000)); a streptozotocin (STZ)-diabetic rat for study of autonomic neuropathy (Schmidt et al., Am. J. Pathol., 163;21-8 (2003)); and a progressive motor neuropathy (pmn) mouse (Martin et al., Genomics, 75:9-16 (2001)). With no respect to neoplastic disorders, again, numerous animal and cellular models have been described. An exemplary in vivo system for evaluating a compound for its ability to limit the spread of primary tumors is described by Crowley et al., *Proc. Natl. Acad. Sci.,* 90:5021-5025 (1993). Nude mice are injected with tumor cells (PC3) engineered to express CAT (chloramphenicol acetyltransferase). Compounds to be tested for their ability to decrease tumor size and/or metastases are administered to the animals, and subsequent measurements of tumor size and/or metastatic growths are made. The level of CAT detected in various organs provides an indication of the ability of the compound to inhibit metastasis; detection of less CAT in tissues of a treated animal versus a control animal indicates less CAT-expressing cells have migrated to that tissue or have propagated within that tissue.

Administration of Compounds and Formulations thereof

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, e.g., between 0.001-1 mg/kg, 1-100 mg/kg, or 0.01-5 mg/kg, every 4 to 120 hours, e.g., about every 6, 8, 12, 24, 48, or 72 hours, or according to the requirements of the particular compound. The methods herein contemplate administration of an effective amount of compound or compound composition to achieve the desired or stated effect (e.g., reduction of feeding in a subject). Typically, the pharmaceutical compositions of this invention will be administered from about 1 to about 6 times per day, for example, the compounds can be administered about 1 to about 4 (e.g., 1,2,3, or 4) hours prior to meal time. Alternatively, the compounds can be administered as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, die, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic compounds if present, in amounts effective for achieving a modulation of disease or disease symptoms, including kinase mediated disorders or symptoms thereof. The compositions are made by methods including the steps of combining one or more compounds delineated herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form.

The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional compound should be present at dosage levels of between about 1 to 100%, and more preferably between about 5 to 95% of the dosage normally administered in a monotherapy regimen. Additionally, combinations of a plurality of compounds described herein are also envisioned. The additional compounds may be administered separately, as part of a multiple dose regimen, from the compounds of this invention. Alternatively, those compounds may be part of a single dosage form, mixed together with the compounds of this invention in a single composition.

Treatments

The compounds described herein can be administered to cells in culture, e.g. in vitro or ex vivo, or to a subject, e.g., in vivo, to treat, prevent, and/or diagnose a variety of disorders, including those described herein below.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Many compounds described herein can be used to treat or prevent a metabolic disorder. A "metabolic disorder" is a disease or disorder characterized by an abnormality or malfunction of metabolism. One category of metabolic disorders is disorders of glucose or insulin metabolism. For example, the subject can be insulin resistant, e.g., have insulin-resistance diabetes. In one embodiment, a compound described herein can be used to decrease insulin or glucose levels in a subject. In another embodiment, a compound described herein can be used to alter (e.g., increase) insulin or glucose levels in a subject. Treatment with a compound may be in an amount effective to improve one or more symptoms of the metabolic disorder.

In some instances, the invention provides a method of treating metabolic syndrome, including administering to a subject an effective amount of a compound described herein.

The metabolic syndrome (e.g., Syndrome X) is characterized by a group of metabolic risk factors in one person. They include: central obesity (excessive fat tissue in and around the abdomen), atherogenic dyslipidemia (blood fat disorders—mainly high triglycerides and low HDL cholesterol—that foster plaque buildups in artery walls); insulin resistance or glucose intolerance (the body can't properly use insulin or blood sugar); prothrombotic state (e.g., high fibrinogen or plasminogen activator inhibitor [−1] in the blood); raised blood pressure (i.e., hypertension) (130/85 mmHg or higher); and proinflammatory state (e.g., elevated high-sensitivity C-reactive protein in the blood).

The underlying causes of this syndrome are overweight/obesity, physical inactivity and genetic factors. People with metabolic syndrome are at increased risk of coronary heart disease, other diseases related to plaque buildups in artery walls (e.g., stroke and peripheral vascular disease) and type 2 diabetes. Metabolic syndrome is closely associated with a generalized metabolic disorder called insulin resistance, in which the body can't use insulin efficiently.

Many compounds described herein can be used to treat or prevent obesity, e.g., in a human subject, e.g. a child or adult subject. "Obesity" refers to a condition in which a subject has a body mass index of greater than or equal to 30. Many compounds described herein can be used to treat or prevent an over-weight condition. "Over-weight" refers to a condition in which a subject has a body mass index of greater or equal to 25.0. The body mass index (BMI) and other definitions are according to the "NIH Clinical Guidelines on the Identification and Evaluation, and Treatment of Overweight and Obesity in Adults" (1998). Treatment with the compound may be in an amount effective to alter the weight of the subject, e.g., by at least 2, 5, 7, 10, 12, 15, 20, 25, 30, 25, 40, 45, 50, or 55%. Treatment with the compound may be in an amount effective to reduce the body mass index of the subject, e.g., to less than 30, 28, 27, 25, 22, 20, or 18. The compounds can be used to treat or prevent aberrant or inappropriate weight gain, metabolic rate, or fat deposition, e.g., anorexia, bulimia, obesity, diabetes, or hyperlipidemia (e.g., elevated triglycerides and/or elevated cholesterol), as well as disorders of fat or lipid metabolism.

For example, agonists of GHS-R can be used to increase food intake or to treat disorders associated with weight loss, e.g., anorexia, bulimia, and so forth. Antagonists or inverse agonists of GHS-R can be used to treat aberrant or inappropriate weight gain, metabolic rate, or fat deposition, e.g., obesity, diabetes, or hyperlipidemia, as well as disorders of fat or lipid metabolism that results in weight gain. In one embodiment, a compound described herein is used to treat hypothalamic obesity. For example, the compound can be administered to a subject identified as at risk for hypothalamic obesity or to a subject that has an abnormal (e.g., extreme) insulin response to glucose.

In another embodiment, a compound described herein (e.g., a GHS-R antagonist or inverse agonist) can be administered to treat obesity associated with Prader-Willi Syndrome (PWS). PWS is a genetic disorder associated with obesity (e.g., morbid obesity). In general, individuals suffering from PWS also have deficient GH secretion. As opposed to individuals having common obesity, those individuals having PWS associated obesity have high fasting-ghrelin concentrations, which might contribute to hyperphagia. Accordingly, in some instances, a subject suffering from PWS associated obesity can be identified using genetic markers, determination of GH levels, fasting-ghrelin concentrations, careful phenotyping, or other methods known in the art.

Administration of a GHS-R antagonist such as one of the compounds described herein can be used to reduce body fat, prevent increased body fat, reduce cholesterol (e.g., total cholesterol and/or ratios of total cholesterol to HDL cholesterol), and/or reduce appetite in individuals having PWS associated obesity, and/or reduce comorbidities such as diabetes, cardiovascular disease, and stroke.

Many compounds described herein can be used to treat a neurological disorder. A "neurological disorder" is a disease or disorder characterized by an abnormality or malfunction of neuronal cells or neuronal support cells (e.g., glia or muscle). The disease or disorder can affect the central and/or peripheral nervous system. Exemplary neurological disorders include neuropathies, skeletal muscle atrophy, and neurodegenerative diseases, e.g., a neurodegenerative disease other than one caused at least in part by polyglutamine aggregation. Exemplary neurodegenerative diseases include: Alzheimer's, Amyotrophic Lateral Sclerosis (ALS), and Parkinson's disease. Another class of neurodegenerative diseases includes diseases caused at least in part by aggregation of polyglutamine. Diseases of this class include: Huntington's Diseases, Spinalbulbar Muscular Atrophy (SBMA or Kennedy's Disease) Dentatorubropallidoluysian Atrophy (DRPLA), Spinocerebellar Ataxia 1 (SCA1), Spinocerebellar Ataxia 2 (SCA2), Machado-Joseph Disease (MJD; SCA3), Spinocerebellar Ataia 6 (SCA6), Spinocerebellar Ataxia 7 (SCA7), and Spinocerebellar Ataxia 12 (SCA12). Treatment with the compound may be in an amount effective to ameliorate at least one symptom of the neurological disorder. In one embodiment, a compound having GHS-R antagonist activity can be used to treat the neruological disorder.

Many compounds described herein can be used to modulate anxiety in a subject. In one embodiment, a compound having, for example, GHS-R antagonist or inverse agonist activity can be used to decrease anxiety.

Many compounds described herein can be used to modulate memory retention in a subject. In one embodiment, a compound having GHS-R antagonist or inverse agonist activity can be used to decrease memory retention. For example, decreasing memory retention may aid recovery from traumatic stress. In one embodiment, a compound having GHS-R agonist activity is used to increase memory retention.

Many compounds described herein can be used to modulate sleep, sleep cycles (e.g., REM sleep), or wakefulness in a subject. In one embodiment, a compound having GHS-R agonist activity is used to promote sleep in the subject or to treat sleep apnea. In one embodiment, a GHS-R agonist, inverse agonist or antagonist (e.g., a compound described herein, is used to alter the circadian rhythm of a subject. For example, the compound can be delivered at particular times of day, e.g., regularly, e.g., in the evening and/or morning, to reset a circadian rhythm, e.g., prior to, during, or after traveling between timezones, or to a subject having a circadian disorder. The compounds can, e.g., modulate the pulsatility of GH secretion.

Many compounds described herein can be used to treat a cardiovascular disorder. A "cardiovascular disorder" is a disease or disorder characterized by an abnormality or malfunction of the cardiovascular system, e.g., heart, lung, or blood vessels. Exemplary cardiovascular disorders include: cardiac dysrhythmias, chronic congestive heart failure, ischemic stroke, coronory artery disease and cardiomyopathy. Treatment with the compound may be in an amount effective to ameliorate at least one symptom of the cardiovascular disorder, e.g., elevated triglyceride levels or elevated cholesterol. In one embodiment, a compound having GHS-R antagonist or inverse agonist activity can be used to treat the cardiovascular disorder.

Many compounds described herein can be used to treat a dermatological disorder or a dermatological tissue condition. A "dermatological disorder" is a disease or disorder characterized by an abnormality or malfunction of the skin. A "dermatological tissue condition" refers to the skin and any underlying tissue (e.g., support tissue), which contributes to the skin's function and/or appearance, e.g., cosmetic appearance. Treatment with the compound may be in an amount effective to ameliorate at least one symptom of the dermatological disorder or the dermatological tissue condition. In one embodiment, a compound having GHS-R antagonist or inverse agonist activity can be used to treat the dermatological disorder or dermatological tissue condition.

Many compounds described herein can be used to treat a geriatric disorder. A "geriatric disorder" is a disease or disorder whose incidence, at the time of filing of this application and in a selected population of greater than 100,000 individuals, is at least 70% among human individuals that are greater than 70 years of age. In one embodiment, the geriatric disorder is a disorder other than cancer or a cardio-pulmonary disorder. A preferred population is a United States population. A population can be restricted by gender and/or ethnicity.

Many compounds described herein can be used to treat or prevent a disorder characterized by excessive growth hormone activity. For example, the compounds can be used to reduce GH levels in the subject. In one embodiment, the subject is a human, e.g., a child (e.g., between 3-11 years), an adolescent (e.g., between 12-19 years), a young adult (e.g., between 20-25 years), or an adult. In one embodiment, a compound having GHS-R antagonist or inverse agonist activity is used to treat the disorder characterized by excessive growth hormone activity.

Many compounds described herein can be used to modulate vagal tone. For example, a compound described herein or other modulator of GHS-R can be administered to a subject who has a vagotomy or other disorder, which alters vagal afferent or efferent activity. In one embodiment, a subject is monitored for abnormalities in vagal nerve function, and, if a malfunction is detected, the subject is treated with a compound described herein or other modulator of GHS-R.

Exemplary diseases and disorders that are relevant to certain implementations include: cancer (e.g., breast cancer, colorectal cancer, CCL, CML, prostate cancer); skeletal muscle atrophy; adult-onset diabetes; diabetic nephropathy, neruopathy (e.g., sensory neuropathy, autonomic neuropathy, motor neuropathy, retinopathy); obesity; bone resorption; neurodegenerative disorders (Parkinson's disease, ALS, Alzheimer's, short-term and long-term memory loss) and disorders associated with protein aggregation (e.g., other than polyglutamine aggregation) or protein misfolding; age-related macular degeneration, Bell's Palsy; cardiovascular disorders (e.g., atherosclerosis, cardiac dysrhythmias, chronic congestive heart failure, ischemic stroke, coronary artery disease and cardiomyopathy), chronic renal failure, type 2 diabetes, ulceration, cataract, presbiopia, glomerulonephritis, Guillan-Barre syndrome, hemmorrhagic stroke, rheumatoid arthritis, inflammatory bowel disease, multiple sclerosis, SLE, Crohn's disease, osteoarthritis, pneumonia, and urinary incontinence. Symptoms and diagnosis of diseases are well known to medical practitioners.

In certain embodiments, the compounds are directed locally to GHS-R in a target tissue of the organism. GHS-R is expressed in the hypothalamus, heart, lung, pancreas, intestine, brain (particularly in the arcuate nucleus (ARC)), and adipose tissue. A compound described herein can be targeted to one or more of the above tissues. For example, the compound can be formulated for inhalation for targeting to the lung. The compound can be formulated for ingestion, and passage to the intestine for targeting to the intestine. In other embodiments, treatment is directed systemically, and the compound is distributed to the target tissue.

Depending on the disorder and the compound, treatment may involve, in addition, to use of a compound in a class specified above, using a compound in another class. For example, in subjects whose endogenous ghrelin levels are lower than normal generally or lower than normal in an affected region, a treatment may involve using a compound having GHS-R agonist activity. In other subjects whose endogenous ghrelin levels are higher than normal generally or higher than normal in an affected region, treatment may involve using a compound having GHS-R antagonist activity. The suitability of a particular compound can be evaluated, e.g., in an animal-based assay or by monitoring a subject.

Many compounds described herein can be used to modulate activity of a biological signal that controls energy balance. Such signals include peptide signals, such as NPY, AGRP, orexins, MCH, beacon (see, e.g., Collier et al. (2000) Diabetes 49:1766), mealoncyte-stimulating hormone, neuromedin U, corticotrophin-releasing factor, and leptin. For example, NPY is a 36-amino acid peptide that stimulates food intact and depresses metabolic rate. Many compounds described herein can be used to decrease NPY activity. Many compounds described herein can be used to increase activity or availability of an anorexigenic molecule, e.g., bombesin, IL-1β, leptin, and gastrin-releasing peptide. Accordingly, the compounds may increase the discharge rate of the gastric vagal afferent.

We have also found that substance P and derivatives thereof can modulate GHS-R activity. In particular, we found that substance P alters feeding activity of mice in the fast refeed assay. Accordingly, substance P and derivatives thereof can be used to modulating an eating or metabolic disorder as well as other disorders described herein.

Our investigation of GHS-R expression in human tissues has demonstrated that GHS-R is expressed in pituitary cells, brain, spinal cord, uterus, spleen, pancreas, kidney, adrenal gland, skeletal muscle, thyroid, liver, small intestine, and heart. Accordingly, compounds described herein can be used to treat diseases and disorders associated with undesired levels of ghrelin or ghrelin-mediated signaling activity in those tissues. For example, if the level of ghrelin or ghrelin-mediated signaling activity is undesirably low, a compound having GHS-R agonist activity can be used for treatment. If the level of ghrelin or ghrelin-mediated signaling activity is undesirably high, a compound having GHS-R antagonist activity can be used for treatment. For example, the level of desired ghrelin activity can vary from tissue to tissue. Ghrelin is secreted by the stomach and may be high in or near the stomach, but much lower in normal pancreatic tissue.

Neoplastic Disorders

Many compounds described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders (e.g., tumors arising from prostate, colon, lung, breast and liver origin), hematopoietic neoplastic disorders, e.g., leukemias, metastatic tumors. Prevalent cancers include: breast, prostate, colon, lung, liver, and pancreatic cancers. Treatment with the compound may be in an amount effective to ameliorate at least one symptom of the neoplastic disorder, e.g., reduced cell proliferation, reduced tumor mass, etc.

Whether a neoplastic disorder should be treated with a GHS-R agonist or antagonist can depend on the type of neoplasia. For example, Duxbury et al. (2003) Biochem. Biophys. Res. Comm. 309:464-468 report that certain neoplastic disorders are inhibited by GHS-R antagonists. These disorders include, e.g., pancreatic adenocarcinoma, and neoplasias in which GHS-R or GHS-R1b is expressed, e.g., prostate adenocarcinoma, pancreatic endocrine tumors, somatotroph tumors, and central nervous system tumors. Neoplasias that are attenuated, inhibited, or killed by a GHS-R antagonist are term, herein, "GHS-R antagonist-sensitive neoplastic disorders" and can be treated with a compound having GHS-R antagonist activity.

Duxbury et al. also report that certain other types of neoplasia, e.g., breast, lung, and thyroid adenocarcinomas can be inhibited by high levels ghrelin (>10 nM) and, accordingly, can be treated with a GHS-R agonist, e.g., a GHS-R agonist described herein or another known GHS-R agonist. Neoplasias that are attenuated, inhibited, or killed by ghrelin or a GHS-R agonist are term, herein, "ghrelin-sensitive neoplastic disorders" and can be treated with a compound having GHS-R agonist activity.

Whether a neoplastic cell is sensitive to a ghrelin agonist or antagonist (i.e., whether the neoplastic cell is a ghrelin-sensitive or GHS-R antagonist sensitive neoplastic disorder) can be determined by a proliferation assay in the presence of a GHS-R agonist e.g., ghrelin, or antagonist, e.g., D-Lys-GHRP6. Duxbury et al. disclose an exemplary proliferation assay. In one such assay, cells are seeded into 96 well plates with about $10^4$ cells per well. The cells are cultured for 3 days in medium, and then contacted with ghrelin or D-Lys-GHRP6, or a control medium. Cells are then evaluated using the MTT assay (3-(4,5-dimethylthiazolyl-2yl)-2,5-diphenyltetrazolium) (from Trevigen, Gaithersburg, Md.) for viability. Other assays that can be performed are invasion and migration assays. The affect of a particular compound may also depend on concentration, which can also be varied in the assay.

In addition to the above-mentioned neoplastic disorders, compounds described herein can be used to treat other neoplasias and hyperplasias including "tumors," which may be benign, premalignant or malignant.

Further examples of cancerous disorders include, but are not limited to, solid tumors, soft tissue tumors, and metastatic lesions. Examples of solid tumors include malignancies, e.g., sarcomas, adenocarcinomas, and carcinomas, of the various organ system, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using the methods and compositions of the invention.

A compound described herein can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphanigiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97). Lymphoid malignancies, which may be treated by the subject method, include, but are not limited to acute lymphoblastic leukemia (ALL), which includes B-lineage ALL and T-lineage ALL, chronic lymphocytic leukemia (CLL), prolymphocyctic leukemia (PLL), hairy cell leukemia (HLL) and Waldenstrom's macroglobulinemia (WM). Additional forms of malignant lymphomas contemplated by the treatment method of the invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Agonizing GHS-R

Compounds that agonize GHS-R can be used to treat a disorder in which a subject has less than a desired or less than a normal level of GHS-R activity, e.g., in a particular tissue. Such compounds can be used to treat one or more of the following disorders: cachexia, wasting, stimulating growth hormone release in elderly humans, patients with cancer, heart failure, or AIDS; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; treatment of osteochondrody-splasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing protein loss due to chronic illness such as cancer or AIDS; accelerating weight gain and protein accretion in patients on TPN (total parenteral nutrition); treatment of hyperinsulinemia; treatment of gastric and duodenal ulcers; stimulation of thymic development; adjunctive therapy for patients on chronic hemodialysis; treatment of immunosuppressed patients; enhancement of an antibody response, e.g., following vaccination; increasing the total lymphocyte count of a human; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; prevention and treatment of congestive heart failure; protection of cardiac structure and/or cardiac function; enhancing of recovery of a mammal following congestive heart failure; enhancing and/or improving sleep quality as well as the prevention and treatment of sleep disturbances; enhancing or improving sleep quality by increasing sleep efficiency and augmenting sleep maintenance; prevention and treatment of mood disorders, in particular depression; improving mood and subjective well being in a subject suffering from depression; reducing insulin resistance; stimulation of the immune system; stimulating and promoting gastric motility in patients after surgery or in gastroparesis secondary to degenerative conditions such as type II diabetes; and increasing growth. The compounds can be used to treat a human or an animal, e.g., livestock, a pet, etc.

Kits

A compound described herein can be provided in a kit. The kit includes (a) a composition that includes a compound described herein, and, optionally (b) informational material.

The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). Preferred doses, dosage forms, or modes of administration are parenteral, e.g., intravenous, intramuscular, subcutaneous, intraparenteral, bucosal, sublingual, intraoccular, and topical. In another embodiment, the informational material can include instructions to administer the compound described herein to a suitable subject, e.g., a human, e.g., a human having or at risk for a disorder described herein. For example, the material can include instructions to administer the compound described herein to such a subject.

The informational material of the kits is not limited in its form. In many cases, the informational material, e.g., instructions, is provided in printed matter, e.g., a printed test, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a use of the kit can obtain substantive information about an compound described herein and/or its use in the methods described herein. Of course, the informational material can also be provided in any combination of formats.

In addition to a compound described herein, the composition of the kit can include other ingredients, such as solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is an implantable delivery device.

EXAMPLES

Example 1

Preparation of N,N-3-Dietylaminopropanesulfonyl Chloride Hydrochloride (3)

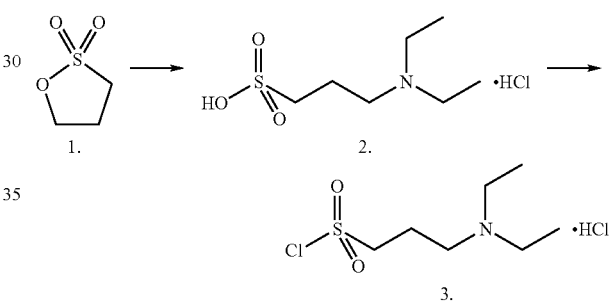

Diethylamine (10 ml, 96.78 mmol) was added slowly to the 1,3 Propane sultone (3.94 g, 32.26 mmol) whilst stirring at 0° C. This was allowed to stir overnight whilst warming to ambient temperatures. The reaction mixture was then diluted with MeOH (100 ml) followed by the addition of Ambersep900 resin (30 g, 75 mmol) and shaken for 2 hours. The resin was washed, on a glass sinter with 30 ml aliquots of MeOH (washings discarded). The resin was then treated with 2M $HCl_{(aq)}$ (50 ml) for 30 mins, and then filtered. The resin was washed with 2M $HCl_{(aq)}$ (2×50 ml). The combined acidic solution was evaporated in vacuo to give the crude product N,N-3-diethylaminopropane sulfonic acid hydrochloride (2) as a white solid.

Example 2

Synthesis of (R)-3-(Benzyloxy)-2-(3-(diethylamino) propylsulfonamido)(Propanoic Acid Thionyl chloride (50 ml, 685 mmol) was added to N,N-3-diethylaminopropane sulfonic acid hydrochloride (2) and heated to reflux whilst stirring for 8 hours. The solution was allowed to cool to ambient temperatures and then evaporated in vacuo to give N,N-3-diethylaminopropanesulfonyl chloride hyrochloride (3) as a grey/white, very hydroscopic solid (7.9 g, 92%). The product was stored under a nitrogen atmosphere.

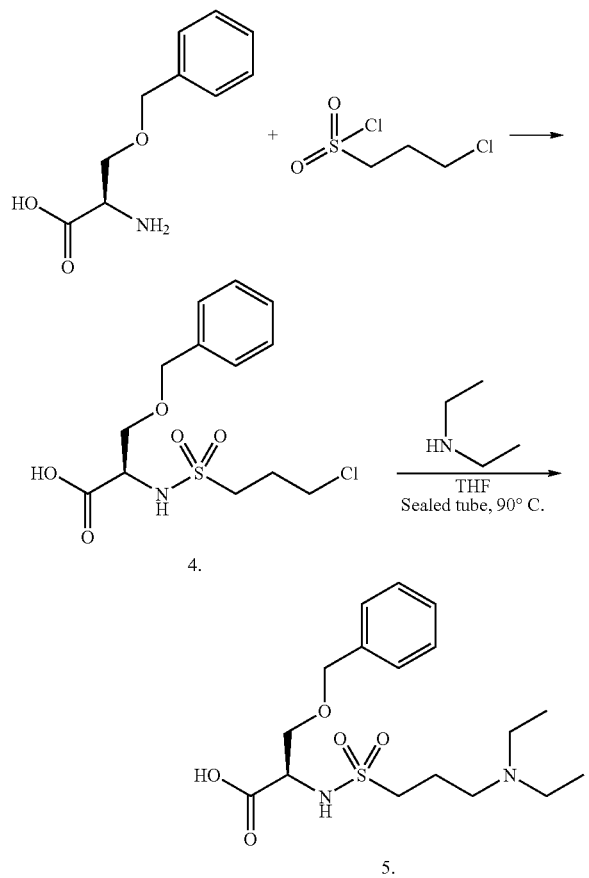

Synthesis of 4:

O-Bn-D-serine (3 g, 15.36 mmol) was suspended in DMF (60 mL). BSTFA (bis(trimethylsilyl)trifluoroacetamide) (0.75 mL, 15.36 mmol) was added to the suspension, which was stirred at room temperature for 2 hours. All the starting material was dissolved.

3-Chloropropane sulfonyl chloride (2.25 mL, 18.43 mmol) was then added and the mixture was stirred at room temperature over night. The DMF was removed by evaporation in vacuo and ethyl acetate was added. The desired 4 was extracted using aqueous NaOH (1M) (70 mL). The aqueous phase was then acidified with aqueous HCl (5 M) to pH 1. The desired compound was then extracted using ethyl acetate, dried over $Na_2SO_4$ and the organic solvent was evaporated in vacuo to give m=3.8 g of 4 as a dark brown oil. $^1$H NMR ($CDCl_3$): 2.27 (m, 2H); 2.90-3.23 (m,2H); 3.58 (t, 2H); 3.77 (m, 1H); 3.90 (m, 1H); 3.31 (bs, 1H); 4.54 (s, 2H); 5.50 (bs, 1H); 7.26-7.36 (m, 5H).

Synthesis of 5:

4 (1.2 g, 3.58 mmol), was dissolved in THF (3 mL), 3 mL of diethylamine was then added to the solution which was heated at 90° C. in a sealed tube over night. The THF was removed in vacuo and ethyl acetate was added. The desired compound was then extracted using $H_2O$ (2×30 mL). The water was then removed in vacuo in the presence of toluene to give m=1.1 g (82% yield) of a light brown compound.

The oil was dissolved in 100 ml of MeOH, and 5 g of resin Ambersep 900 was added. The mixture was shaken for 1 h and the solvent was removed under reduced pressure. The resin was then washed with MeOH (20 ml) and suspended in HCl (2N) for 1 h. The resin was filtered and the filtrate evaporated to afford 5 as a yellow oil, $^1$H NMR showed less than 10% diethylamine. $^1$H NMR ($D_2O$): 1.04 (t, 6H); 1.84 (m, 2H); 2.47-2.60 (m, 6H); 2.89 (t, 2H); 3.62 (m, 1H); 3.75 (m, 1H); 3.85 (m, 1H); 4.62 (s, 2H); 7.40-7.47 (m, 5H).

Example 3

Synthesis of (R)-3-(diethylamino)-N-(1,3-Substituted-1,2,4-oxadiazol-5-yl)-3-phenylpropyl)propane-1-sulfonamide and (R)-2-(diethylamino)-N-(1-(3-Substituted-1,2,4-oxadiazol-5-yl)-3-phenylpropyl)ethanesulfonamide

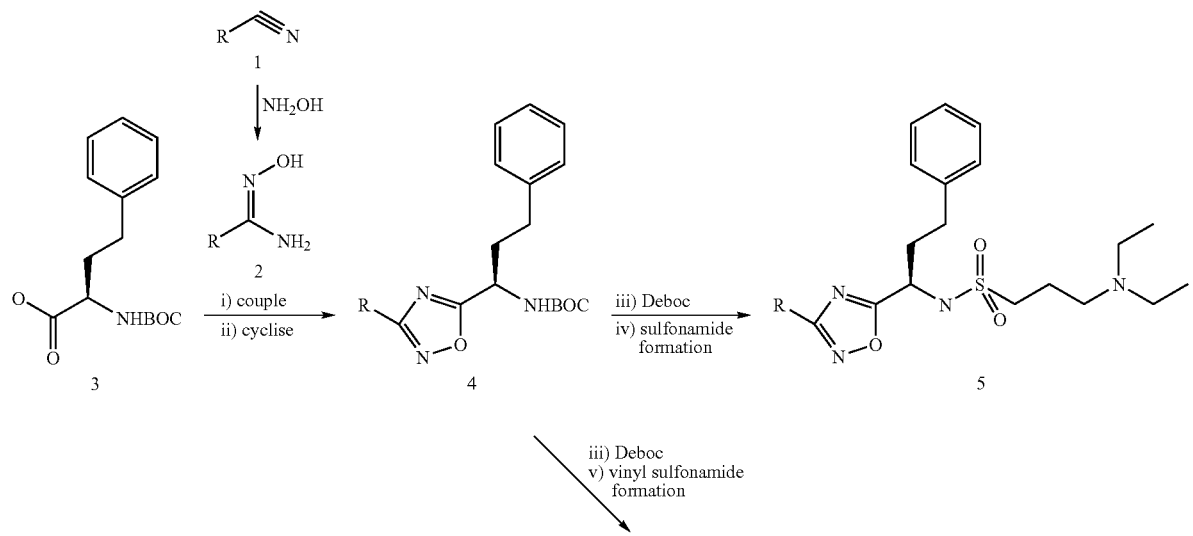

-continued

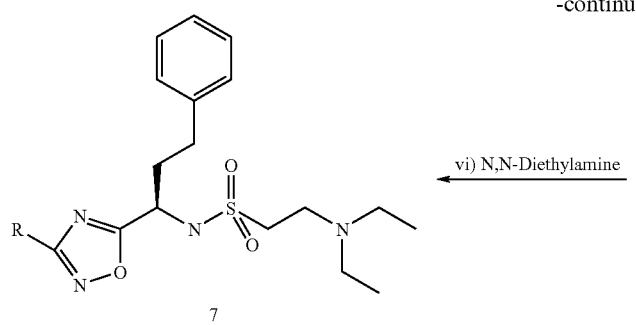 ← vi) N,N-Diethylamine 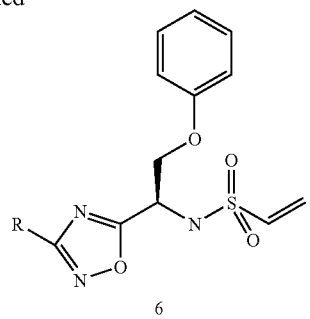

Amidoxime Preparation (2)

A suspension of the nitrile (1) in EtOH (10 ml) and hydroxylamine 50% in water (10 ml) was heated to reflux (approx. 100° C.) whilst stirring for 6 hrs. The reaction mixture was then evaporated to dryness in vacuo. This was then re-evaporated from toluene (10 ml) twice to give the crude product.

Oxadiazole Formation (4)

i) N-BOC-Homophenylalanine (200 mg, 0.72 mmol) was dissolved in EtOAc (10 ml) and cooled to 0° C. To this solution was added CDI (128 mg, 0.79 mmol) and stirred at 0° C. for 15 mins, and then a further 2 hrs whilst warming to ambient temperatures. The amidoxime (2, 0.79 mmol) was then added and the reaction mixture was stirred overnight. The reaction mixture was then washed with sat. NaHCO$_{3(aq)}$ (10 ml) then brine (10 ml) before drying over Na$_2$SO$_4$, filtering and evaporating to dryness in vacuo.

ii) The crude intermediate (i) was dissolved in DMF (2 ml) and heated in a CEM Discover focussed microwave for 1 min at 180° C. The solvent was then evaporated in vacuo and the crude product was purified by silica gel column chromatography, eluting with a mixture of EtOAc/Heptanes (typically 1/9).

Sulfonamide Formation (5)

iii) A solution of TFA (20%) in DCM, 5 ml) was added to the oxadiazole (4) at 0° C. and stirred for 30 mins, before allowing to warm to ambient temperatures. The reaction was monitored by TLC (EtOAc/heptanes, 1/1). The reaction was usually complete after 1 hr stirring at ambient temperatures. The reaction mixture was cooled to 0° C., and slowly basified with sat. Na$_2$CO$_{3(aq)}$. The organic layer was separated and dried with Na$_2$SO$_4$, before evaporating.

iv) The crude product was re-dissolved in DCM (10 ml) and cooled to 0° C. To this solution was added, N,N-diethylaminopropylsulfonyl chloride. Hydrochloride (1.3 eq), followed by DIPEA (3.0 eq) and stirred overnight whilst allowing to warm to ambient temperatures. The reaction mixture was then washed with brine (2×10 ml), dried over Na$_2$(SO$_4$), and evaporated. The crude product was purified by silica gel column chromatography, eluting with a mixture of MeOH/DCM (typically 5/95).

Vinyl Sulfonamide Formation (6)

iii) As described above v) As described for iv) (5) except 2-chloroethylsulfonyl chloride is to be used. Purification by silica gel column chromatography, eluting with EtOAc/Heptanes (typically 1/9).

Diethylamine Addition (7)

vi) N,N-Diethylamine (2 ml) was added to (6) and stirred at ambient temperatures overnight. This was then evaporated to dryness in vacuo. The crude product was purified by silica gel column chromatography, eluting with a mixture of MeOH/DCM (typically 5/95).

Preparation of N,N-3-Diethylaminopropanesulfonyl Chloride Hyrochloride 10.

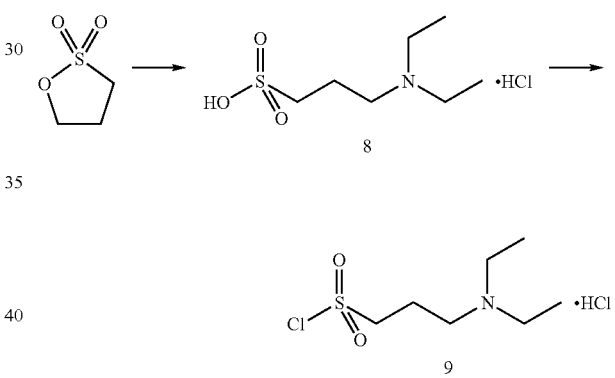

Diethylamine (10 ml, 96.78 mmol) was added slowly to the 1,3 Propane sultone (3.94 g, 32.26 mmol) whilst stirring at 0° C. This was allowed to stir overnight whilst warming to ambient temperatures. The reaction mixture was then diluted with MeOH (100 ml) followed by the addition of Ambersep900 resin (30 g, 75 mmol) and shaken for 2 hours. The resin was washed, on a glass sinter with 30 ml aliquots of MeOh (washings discarded). The resin was then treated with 2M HCl$_{(aq)}$ (50 ml) for 30 mins, and then filtered. The resin was washed with 2M HCl$_{(aq)}$ (2×50 ml). The combined acidic solution was evaporated in vacuo to give the crude product N,N-3-diethylaminopropane sulfonic acid hydrochloride (8) as a white solid.

Thionyl chloride (50 ml, 685 mmol) was added to N,N-3-diethylaminopropane sulfonic acid hydrochloride (8) and heated to reflux whilst stirring for 8 hours. The solution was allowed to cool to ambient temperatures and then evaporated in vacuo to give N,N-3-diethylaminopropanesulfonyl chloride hyrochloride (9) as a grey/white, very hygroscopic solid (7.9 g, 92%). The product was stored under a nitrogen atmosphere.

Example 4

Synthesis of (R)-tert-butyl 3-phenyl-1-(3-(pyridin-2-yl)-1H-(1,2,4-triazol-5-yl)propylcarbamate Stage-1:

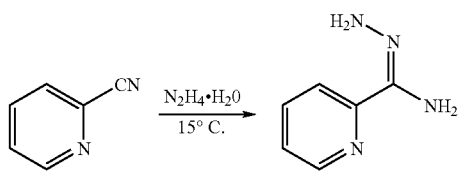

2-Cyano pyridine (500 mg, 1.923 mmol) and Hydrazine hydrate (252 mg, 1.923 mmol) were mixed together in EtOH (3 ml). The clear solution was left at 15° C. (in refrigerator) for 18 h (Monitored by TLC). Ethanol was concentrated under reduced pressure and then the reaction mixture was diluted with diethyl ether (50 ml) and water. The diethyl ether layer was separated, washed with brine, dried over Na2SO4, filtered and concentrated under reduced pressure to $\frac{1}{5}^{th}$ Volume. The ethereal solution was cooled to 0° C. and the obtained solid precipitate was collected over the filtration and dried under vacuum, which gave the 2-pyridine Amidrazone (360 mg).

Stage-2:

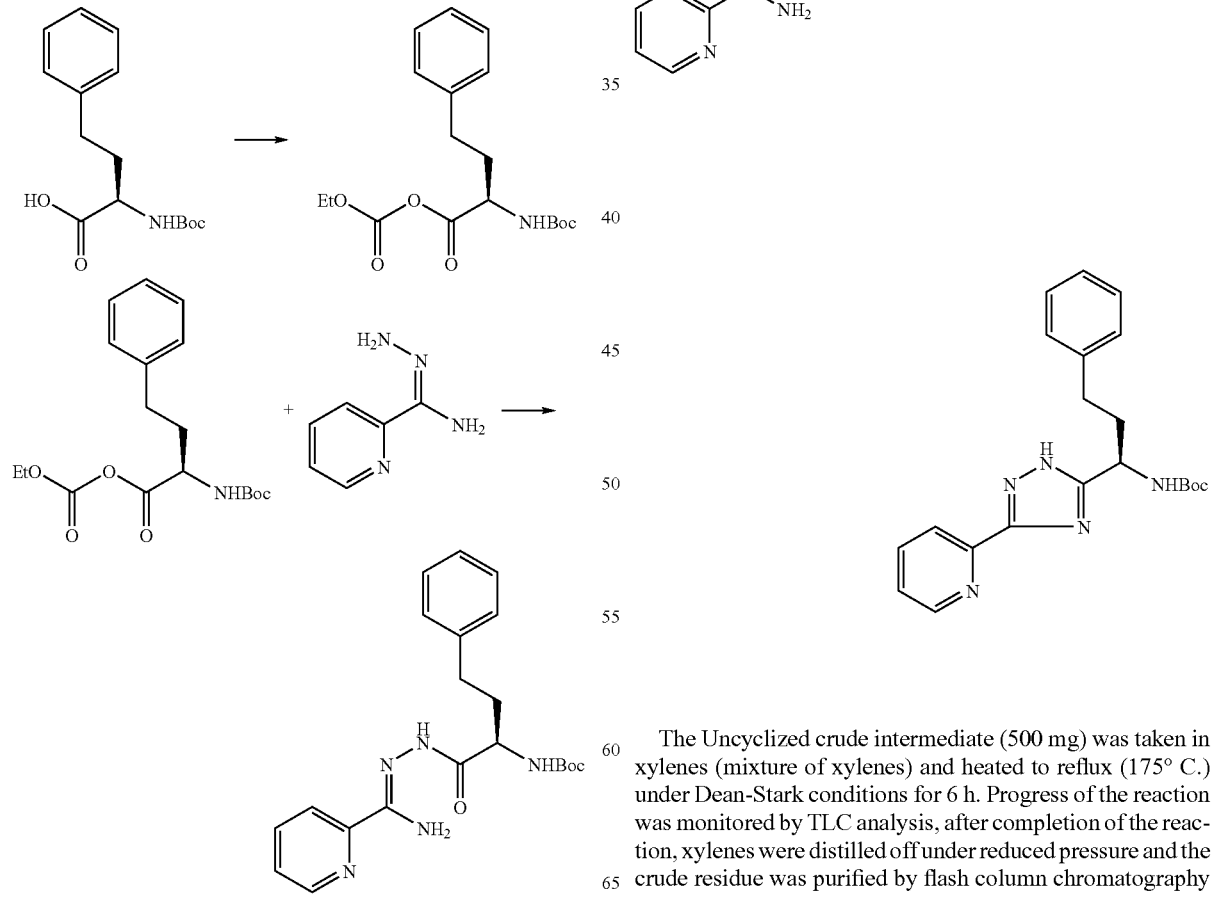

To a solution of the Boc protected Homophenyl alanine (1.1 g, 3.012 mmol) and TEA (370 mg, 3.012 mmol) in dry THF (10 ml) at −5° C. was added ethyl chloro formate (400 mg) drop wise and stirred the reaction mixture for 30 min at the same temperature. TLC shows the formation of activated ester. After completion of the reaction, mixture was filtered through celite (to remove the Triethyl ammonium hydrochloride) and to the filtrate was added the Amidrazone (350 mg) and stirred at RT for 5 h under $N_2$ atmosphere. Progress of the reaction was monitored by TLC analysis. After completion of the reaction, water was added and extracted the mixture with ethyl acetate. The organic layer was washed with water, brine, dried over $Na_2SO_4$, filtered and concentrated to provide the Uncyclized intermediate (500 mg), which was taken to next step without purification.

Stage-3:

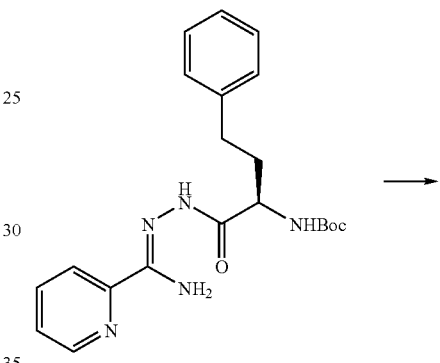

The Uncyclized crude intermediate (500 mg) was taken in xylenes (mixture of xylenes) and heated to reflux (175° C.) under Dean-Stark conditions for 6 h. Progress of the reaction was monitored by TLC analysis, after completion of the reaction, xylenes were distilled off under reduced pressure and the crude residue was purified by flash column chromatography using silica gel to provide 320 mg of the required triazole, confirmed by MS and NMR.

Example 5

Synthesis of (R)-3-(diethylamino)-N-(1-(3-(4-fluorophenyl)-1H-1,2,4-triazol-5-yl)-3-phenylpropyl)propane-1-sulfonamide

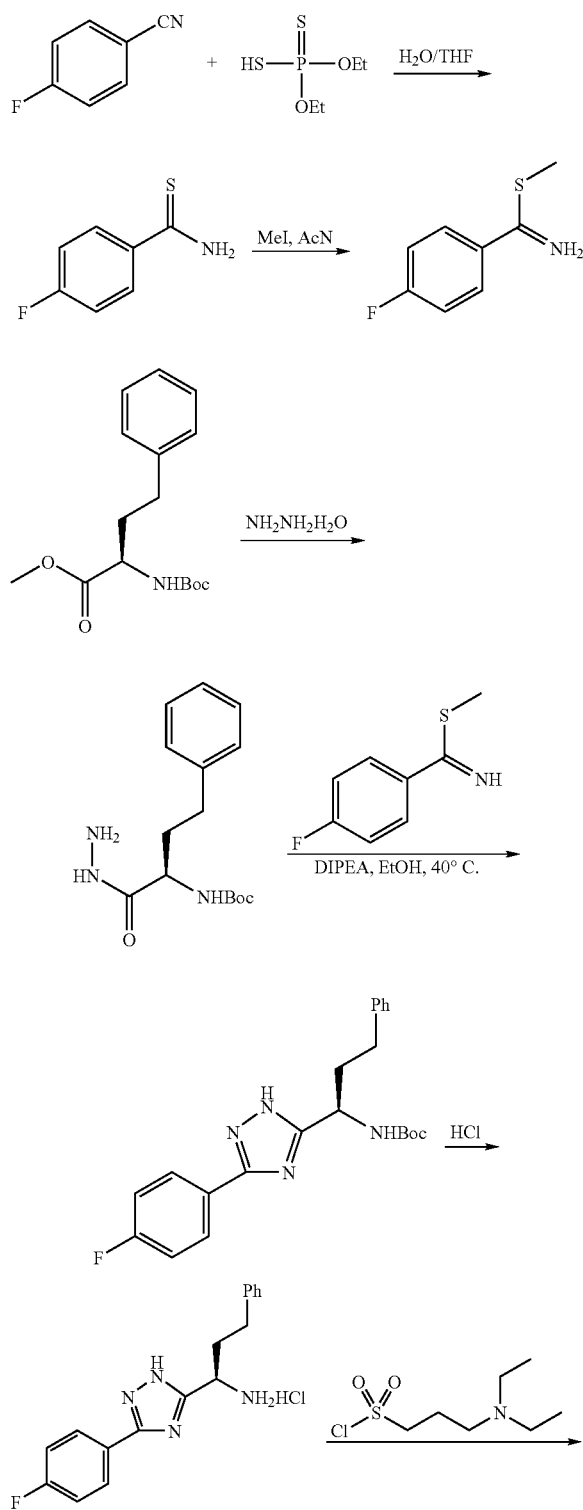

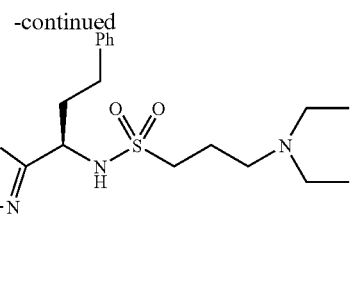

Synthesis of 4-fluorobenzothioamide:

To a solution of 4-fluoro benzonitrile (1)(2.5 g, 20.1 mmol) in THF: water (5 ml:15 ml) was added diethyl dithiophosphate (2) (10.5 g, 60.3 mmol) at room temperature and continued the reaction at 80° C. for 8 h. Progress of the reaction was monitored by TLC analysis. To the reaction mixture was added water (25 ml) and the compound was extracted with ethyl acetate (2×25 ml). The organic layer was washed with brine, dried over sodium sulfate, filtered, concentrated under reduced pressure to give the crude thioamide-3 (2.8 g), taken to next step without further purification.

Synthesis of methyl 4-fluorobenzimidothioate:

To a solution of Thioamide (3) (2.8 g, 18.2 mmol) in acetonitrile (15 ml) was added methyl iodide (11.7 ml, 90.3 mmol) at room temperature and continued the reaction at 80° C. for 1 h. Progress of the reaction was monitored by TLC analysis. The solvent from the reaction mixture was removed under reduced pressure. The obtained crude residue was purified by crystallization using diethyl ether, which gave the thiomethyl derivative-4 (2 g). 1H NMR-500 MHZ (DMSO-$D_6$)δ 11.62 (1H, bm), 8.01 (2H, m), 7.47 (2H, m), 2.92 (3H, s); MS 170 (M+, 100%).

Synthesis of (R)-tert-butyl 1-hydrazinyl-1-oxo-4-phenylbutan-2-ylcarbamate

Boc-HomoPhe-methylester (5) (3 g, 10.2 mmol) was taken in hydrazine hydrate (99% solution (10 ml) at room temperature and continued the reaction at 80° C. for 3 h. Progress of the reaction was monitored by TLC analysis. The reaction was diluted with water and extracted with dichloromethane (2×25 ml). The organic layer was washed with water, brine, dried over sodium sulfate, filtered, concentrated under pressure to provide compound-6 (2.8 g) as white solid. 1H NMR-200 MHZ ($CDCl_3$) δ 7.61 (1H, bs), 7.37-7.21 (5H, m), 5.14 (1H, m), 4.04 (1H, m), 3.81 (2H, bs), 2.67 (2H, t, J=5.2 Hz), 2.21-1.84 (2H, m), 1.42 (9H), s; MS 294 (M+, 100%), 194 (M-Boc, 75%).

Synthesis of (R)-tert-butyl 1-(3-(4-fluorophenyl)-1H-1,2,4-triazol-5-yl)-3-phenylpropylcarbamate:

To a solution of compound-6 (2 g, 6.82 mmol) in ethanol (20 ml) were added compound-4 (2.88 g, 17.05 mmol) followed by DIPEA (6.5 ml, 17.05 mmol) at 0° C. and continued the reaction at 80° C. for 5 h. Progress of the reaction was monitored by TLC analysis. Ethanol was removed from the reaction mixture under reduced pressure and the obtained residue was diluted with water (10 ml) and ethyl acetate (25 ml). The organic layer was separated, washed with water, brine, dried over sodium sulfate, filtered, concentrated under pressure to provide compound-7 (2.3 g). 1 H NMR-200 MHZ ($CDCl_3$)δ 12.01 (1H, bm), 8.06 (2H, m), 7.28-7.12 (7H, m), 5.24 (1H, m), 4.82 (1H, m), 2.73 (2H, t, J=5.2 Hz), 2.42-2.18 (2H, m), 1.44 (9H, s); MS 396 (M+, 100%), 296 (M-Boc, 75%).

Synthesis of 3-(diethylamino)Propane-1-sulfonyl chloride:

To a solution of 1,3-propanesultone (5 g, 40.98 mmol) in dichloromethane (20 ml) was added diethyl amine (15 ml, 204.9 mmol) drop wise at 10° C. and continued the reaction for 1 h. Progress of the reaction was monitored by TLC analysis. Dichloromethane was removed from the reaction mixture under reduced pressure and the obtained residue was crystallized from diethyl ether to produce the sulfonic acid compound as solid (4.9 g) 1H NMR-200 MHZ (CDCl$_3$)δ 9.44(1H, bm), 3.16 (6H, m), 2.63 (2H, t, J=5.2 Hz), 1.96 (2H, m), 1.20 (6H, t, J=5.2 Hz); MS 195 (M+, 100%).

The above-obtained sulfonic acid (4.9 g) was taken in Thionyl chloride (40 ml) and the reaction mixture was continued stirring at 80° C. for 5 h. Progress of the reaction was monitored by TLC analysis. Excess Thionyl chloride was removed under reduced pressure and the obtained residue was thoroughly azeotroped using toluene (3×50 ml) under nitrogen atmosphere. The crude residue was washed thoroughly with diethyl ether (3×10 ml) followed by hexane (3×10 ml) to give pure compound-A, which was used in the next reaction without further purification.

Synthesis of (R)-1-(3-(4-fluorophenyl)-1H-1,2,4-triazol-5-yl)-3-phenylpropan-1-amine hydrochloride:

Compound-7 (2.3 g, 5.808 mmol) was taken in methanolic HCl (20% solution, 20 ml) at 0° C. and continued the reaction at room temperature for 3 h. Progress of the reaction was monitored by TLC analysis. Solvent was removed from the reaction mixture under reduced pressure and the obtained solid was thoroughly washed with diethyl ether to produce the compound-8-HCl (2 g) 1H NMR-200 MHZ (DMSO-D$_6$) δ8.71(1H, bm), 8.12 (2H), m), 7.43-7.16 (7H, m), 4.42 (1H, m), 2.65 (2H, t, J=5.2 Hz), 2.22 (2H, m); MS 297 (M+, 80%).

Synethesis of (R)-3-(diethylamino)-N-(1-(3-(4-fluorophenyl)-1H-1,2,4-triazol-5-yl)-3-phenylpropyl)propane-1-sulfonamide:

To a 0° C. cooled solution of Compound-8 (250 mg, 0.753 mmol) in dichloromethane (5 ml) was added triethylamine (0.5 ml, 4.518 mmol). To the reaction mixture was added a solution of compound-A (240 mg, 1.129 mmol) in dichloromethane (2.5 ml) drop wise and the reaction mixture was continued stirring for 1 h. Progress of the reaction was monitored by TLC analysis. The reaction mixture was diluted with dichloromethane (20 ml), washed with saturated sodium bicarbonate solution, water followed by brine solution. The organic layer was dried over sodium sulfate, filtered, concentrated under reduced pressure to provide the crude material. The crude residue was purified by flash column chromatography on silica gel using methanol: dichloromethane (4:96) as eluent. The obtained compound was taken in dichloromethane and washed with water. The organic layer was dried over sodium sulfate, filtered, concentrated under reduced pressure to provide pure compound as thick brown (155 mg) 1H NMR-200 MHz (CD$_3$OD)δ 8.08 (2H, m), 7.37-7.16 (7H, m), 4.63 (1H, t, J=5.2 Hz), 2.98 (8H, m), 2.35 (2H, m), 1.95 (2H, m), 1.05 (6H, t, J=5.2 Hz); MS 473.8 (M+, 100%).

Example 6

Reduced Ghrelin-Induced Food Intake in Mice Dosed ip with Compound 57

Ad libidum low fat chow-fed male C57bl/6 mice were acclimated to individual housing for >5 days prior to the experiment. On the morning of the experiment food was removed from the cages and animals were then dosed ip (n=8/group) with either vehicle or ghrelin followed one minute later by a second ip injection containing either vehicle or one of several doses of compound (1, 3, 10, 30mpk ip). Immediately after the second dosing food was returned to the cages and food intake was measured 1, 2, 4 and 6 hours later. The results are provided in FIGS. 1 and 2, demonstrating reduced food intake in mice dosed with compound 57 and compound 94 respectively relative to mice dosed with vehicle.

Example 7

Exemplary Compounds Were Orally Bioavailable

Male, diet-induced obese, ad libidum fed, C57bl/6 mice were used for these preliminary PK studies. They were dosed (n=3 mice per data point) either IV or PO. Mice ere sacrificed and the blood/brains collected at the following times: IV samples were taken at 5, 15, 30, 60, 120, 240, 480 minutes after dosing; PO samples were taken at 15, 30, 60, 120, 240, 480 minutes after dosing. Plasma and brain samples were evaluated for the presence of compound. Oral bioavailability (% F) was determined by comparing the plasma AUC$_{IV}$ and AUC$_{PO}$. The brain/plasma ratio was determined by comparing the brain AUC and plasma AUC values. The results, provided in Table 2 below, demonstrate that the sample compounds 57 and 94 are orally bioavailable.

| Compound | % F | % Brain/Plasma |
|---|---|---|
| Compd 57 | 10.2 | 13.9 |
| Compd 94 | 63.2 | 8.7 |

Example 8

Figure 3A:
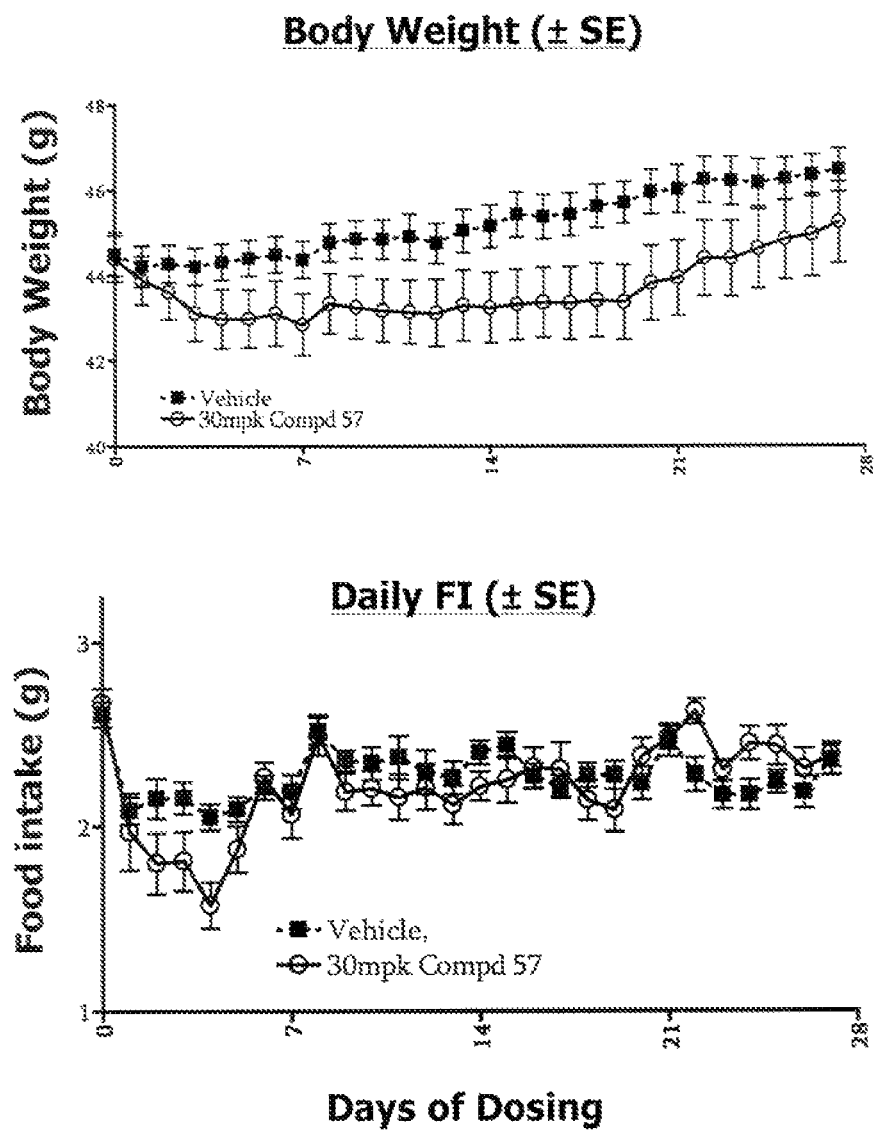
FIGS. 3a and 3b demonstrate how administration of compounds 57 and 94 resulted in decreased body weight in mice. No apparent effect on food intake was observed.
Figure 3B:
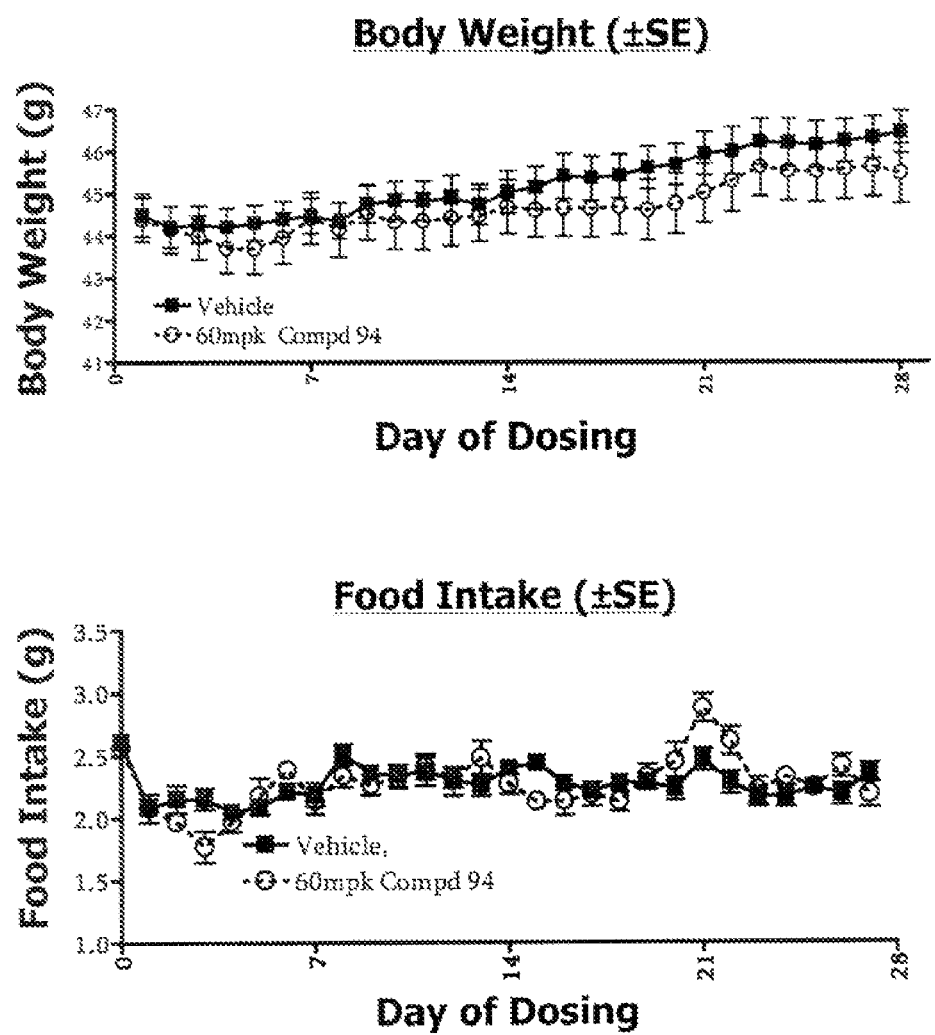

28 Days Oral Dosing of Compounds 57 and 94 Caused a Decrease in Body Weight with No Apparent Effect on Food Intake Group housed, male, C57bl/6 mice received high fat diet and water ad lib to establish diet-induced obesity, and for the duration of the experiment. After acclimating to individual housing for at least 5 days, mice were then acclimated to bid oral gavage with vehicle for 7 days. Once acclimated, mice were culled into equal groups (n>10/group) according to body weight and compound dosing began. Mice received either vehicle or compound (bid, po) for periods up to 28 days, during which body weight and food intake were measured daily. Representative cohorts (based on BW) for each group were removed at 7, 14, 21 or 28 days for glucose tolerance tests and tissue analysis. As shown in FIG. 3*a* and FIG. 3*b*, administration of compound 57 and compound 94 provided a decrease in body weight. No apparent effect on food intake was observed.

Example 9

7 to 28 Days Oral Dosing of Compounds 57 and 95 Improved Insulin Sensitivity

On the night prior to the GTT, mice (DIO) within each dose group (n=8/group) had their body weight measured and were then fasted overnight for 16 hours prior to the GTT. On the morning of the GTT a 40 μL blood sample was removed from the tail for baseline fasted blood glucose and plasma insulin measurements. Mice then received their normal dose of compound. One hour later mice were dosed with glucose (1 mg/Kg, either IP or PO) and further tail bleeds (40□L) were taken at 15, 30, 60 and 120 minutes after the glucose dose for blood glucose and plasma insulin measurements. Mice were sacrificed following the final sample time. Baseline fasted blood glucose levels are provided in FIG. 4a for compound 57 and in FIG. 4d for compound 94. FIG. 4b shows the data demonstrating improved insulin sensitivity of mice dosed with compound 57 at 7 days, whereas FIG. 4e shows the data demonstrating improved insulin sensitivity of mice dosed with compound 94 at 7 days. FIG. 4c shows the data demonstrating improved insulin sensitivity of mice dosed with compound 57 at 21 days. FIG. 4f shows the data demonstrating improved insulin sensitivity of mice dosed with compound 94 at 28 days.

Example 10

Figure 7:
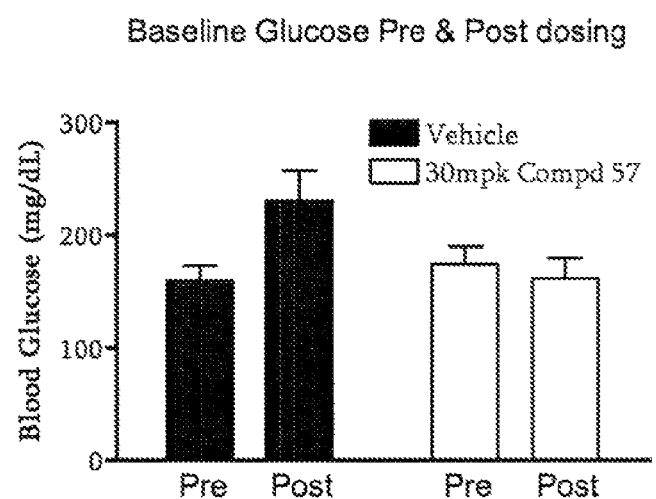
FIG. 7 demonstrates improved fasting blood glucose at 14 days in mice dosed with compound 57.

28 Day Dosing of Compound 57 and Compound 94 Results In Improved Plasma HbA1c and Cholesterol Levels Mice are sacrificed by $CO_2$ asphyxiation and terminal blood samples were collected via cardiac puncture. For HbA1c, whole blood is analyzed using a DCA2000+ glycated hemoglobin analyzer (Bayer Healthcare, Indianapolis, Ind.). Triglycerides, total cholesterol, and HDL-cholesterol were all measured using a Cholestech LDX lipid profile analyzer (Cholestech, Hayward, Calif.). As shown in FIG. 6 and FIG. 7, both plasma HbA1c and cholesterol levels were improved at 28 days in animals treated with compound 57 and compound 94 versus animals treated with vehicle alone.

Example 11

14 Day Oral Dosing with Compound 57 Improves Fasting Blood Glucose In db/db Mice Mice that had been acclimated to individual housing and oral gavage dosing were fasted for 16 hours overnight. The following morning a blood sample was removed from the tail for baseline fasted blood glucose measurements. This process was repeated after 14 days oral bid dosing with compound 57. Whereas fasted blood glucose levels continued to rise in vehicle treated animals, there was no change in mice treated with the ghrelin antagonist. Thus, compound treatment blocked the development of hyperglycemia in this model of type 2 diabetes. FIG. 7 illustrates the improvement in fasting blood glucose levels of mice treated with compound 57.

A number of embodiments of the invention have been described. Nevertheless, it will be understood that various modifications may be made without departing from the spirit and scope of the invention. Accordingly, other embodiments are within the scope of the following claims.

What is claimed is:
1. A compound of formula (I)

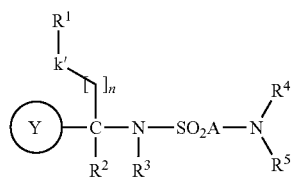

formula (I)

wherein,
$R^1$ is hydrogen, aryl, heteroaryl, arylalkyl, heteroarylalkyl, cyclyl, cyclylalkyl, heterocyclyl, heterocyclylalkyl, alkyl, alkenyl, alkynyl, or $R^1$ can be taken together with $R^2$ or $R^3$ to form a ring; each of which is optionally substituted with 1-4 $R^6$;

k' is a bond, O, C(O), C(O)O, OC(O), C(O)$NR^3$, $NR^3$C(O), S, SO, $SO_2$, $CR^2$=$CR^2$, or C≡C;

n is 0-6;

$R^2$ is hydrogen, $C_1$-$C_6$ alkyl, $C_2$-$C_6$ alkenyl, or $C_2$-$C_6$ alkynyl; or $R^2$ can be taken together with $R^1$ to form a ring;

$R^3$ is hydrogen, $C_1$-$C_6$ alkyl, $C_2$-$C_6$ alkenyl, or $C_2$-$C_6$ alkynyl, or $R^3$ can be taken together with $R^2$, $R^4$, or $R^5$ to form a ring; each of which can be optionally substituted with 1-2 $R^{6'}$;

A is

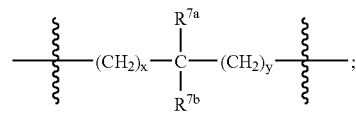

x and y are each independently 0-6;

M is aryl, heteroaryl, cyclyl, or heterocyclyl, each of which is optionally substituted with 1-4 $R^9$;

$R^4$ and $R^5$ are each independently hydrogen, alkyl, alkenyl, haloalkyl, cyclyl, or heterocyclyl, or $R^4$ and $R^5$ can be taken together to form a heterocyclic ring, or $R^4$ and $R^5$ can be taken together to form an azido moiety, or one or both of $R^4$ and $R^5$ can independently be joined to one or both of $R^{7a}$ and $R^{7b}$ to form one or more bridges between the nitrogen to which the $R^4$ and $R^5$ are attached and $R^{7a}$ and $R^{7b}$, wherein each bridge contains 1 to 5 carbons; or one or both of $R^4$ and $R^5$ can independently be joined to one or both of $R^{7a}$ and $R^{7b}$ to form to form one or more heterocyclic rings including the nitrogen to which the $R^4$ and $R^5$ are attached, or one or both of $R^4$ and $R^5$ can independently be joined to $R^3$ to form a ring, or one or both of $R^4$ and $R^5$ can independently be joined to $R^8$ to form a ring; wherein each $R^4$ and $R^5$ are optionally independently substituted with 1-5 halo, 1-3 hydroxy, 1-3 alkyl, 1-3 alkoxy, 1-3 oxo, 1-3 amino, 1-3 alkylamino, 1-3 dialklyamino, 1-3 nitrile, or 1-3 haloalkyl;

Y is 1,2,4-triazol-5-yl, optionally substituted with 1-4 $R^{10}$;

each $R^6$ and $R^{6'}$ are independently halo, alkyl, alkenyl, alkynyl, cyclyl, heterocyclyl, aryl, heteroaryl, alkoxy, haloalkyl, haloalkyloxy, haloalkylthio, acetyl, cyano, nitro, hydroxy, oxo, C(O)$OR^2$, OC(O)$R^2$, N($R^3$)$_2$, C(O)N($R^3$)$_2$, $NR^3$C(O)$R^2$, or $SR^2$;

$R^{7a}$ and $R^{7b}$ are each independently hydrogen, alkyl, alkenyl, haloalkyl, cyclyl, cyclylalkyl, or heterocyclyl; or one or both of $R^{7a}$ and $R^{7b}$ can independently be joined to one or both of $R^4$ and $R^5$ to form one or more bridges between the nitrogen to which the $R^4$ and $R^5$ are attached and $R^{7a}$ and $R^{7b}$, wherein each bridge contains 1 to 5 carbons; or one or both of $R^{7a}$ and $R^{7b}$ can independently be joined to one or both of $R^4$ and $R^5$ to form one or more heterocyclic rings including the nitrogen to which the $R^4$ and $R^5$ are attached, or one or both of $R^{7a}$ and $R^{7b}$ can independently be joined with $R^8$ to form a ring; wherein each $R^{7a}$ and $R^{7b}$ can be independently optionally substituted with 1-5 halo, 1-3 hydroxy, 1-3 alkyl, 1-3 alkoxy, 1-3 amino, 1-3 alkylamino, 1-3 dialklyamino, 1-3 nitrile, or 1-3 haloalkyl;

$R^8$ is hydrogen or $C_1$-$C_6$ alkyl, or $R^8$ can be joined with $R^4$, $R^5$, $R^{7a}$ or $R^{7b}$ to form a ring;

$R^9$ is halo, alkyl, cyclyl, heterocyclyl, aryl, heteroaryl, alkoxy, haloalkyl, haloalkyloxy, haloalkylthio, acetyl, cyano, nitro, hydroxy, oxo, $C(O)OR^2$, $OC(O)R^2$, $N(R^2)_2$, $C(O)N(R^2)_2$, $NR^2C(O)R^2$, $SR^2$;

each $R^{10}$ is independently alkyl, alkenyl, alkynyl, halo, cyano, carbonyl, aryl, arylalkyl, arylalkenyl, arylalkynyl, cyclyl, cyclylalkyl, alkoxy, alkoxyalkyl, aryloxy, aryloxyalkyl, heterocyclyl, heterocyclylalkyl, heteroaryl, heteroarylalkyl, —$OR^{11}$, —$NR^{11}R^{11'}$, —$CF_3$, —$SOR^{12}$, —$SO_2R^{12}$, —$OC(O)R^{11}$, —$SO_2NR^{12}R^{12'}$, —$(CH_2)_mR^{14}$ or $R^{15}$; each of which is optionally independently substituted with 1-3 $R^{16}$;

$R^{11}$ and $R^{11'}$ are each independently hydrogen, alkyl, alkenyl, alkynyl, cyclyl, heterocyclyl, aryl or heteroaryl;

$R^{12}$ and $R^{12'}$ are each independently hydrogen, alkyl, alkenyl, alkynyl, alkylthioalkyl, alkoxyalkyl, aryl, arylalkyl, heterocyclyl, heteroaryl, heteroarylalkyl, heterocycloalkyl or cyclyl, cyclylalkyl, or $R^{12}$ and $R^{12'}$ taken together can be cyclized to form —$(CH_2)_qX(CH_2)_s$—; wherein each $R^{12}$ and $R^{12'}$ may independently optionally be substituted with 1 to 3 substituents selected from the group consisting of halogen, $OR^{11}$, alkoxy, heterocycloalkyl, —$NR^{11}C(O)NR^{11}R^{11'}$, —$C(O)NR^{11}R^{11'}$, —$NR^{11}C(O)R^{11'}$, —$CN$, oxo, —$NR^{11}SO_2R^{11'}$, —$OC(O)R^{11}$, —$SO_2NR^{11}R^{11'}$, —$SOR^{13}$, —$S(O)_2R^{13}$, —$COOH$ and —$C(O)OR^{13}$;

each $R^{13}$ is independently alkyl, aryl, arylalkyl, heteroaryl, or heteroarylalkyl, each of which may optionally be substituted with —$(CH_2)_wOH$;

each $R^{14}$ is independently alkoxy, alkoxycarbonyl, —$C(O)NR^{12}R^{12'}$, —$NR^{11}R^{11'}$, —$C(O)R^{12}$, —$NR^{11}C(O)NR^{11}R^{11'}$ or —N-heteroaryl;

each $R^{15}$ is independently —$(CH_2)_pN(R^{12})C(O)R^{12'}$, —$(CH_2)_pCN$, —$(CH_2)_pN(R^{12})C(O)OR^{12'}$, —$(CH_2)_pN(R^{12})C(O)NR^{12}R^{12'}$, —$(CH_2)_pN(R^{12})SO_2R^{12'}$, —$(CH_2)_p SO_2NR^{12}R^{12'}$, —$(CH_2)_pC(O)NR^{12}R^{12'}$, —$(CH_2)_pC(O)OR^{12}$, —$(CH^2)_pOC(O)OR^{12}$, —$(CH_2)_pOC(O)R^{12}$, —$(CH_2)_pOC(O)NR^{12}R^{12'}$, —$(CH_2)_pN(R^{12})SO_2NR^{12}R^{12'}$, —$(CH_2)_pOR^{12}$, —$(CH_2)_pOC(O)N(R^{12})(CH_2)_mOH$, —$(CH_2)_pSOR^{12}$, —$(CH_2)_pSO_2R^{12}$, —$(CH_2)_pNR^{11}R^{11'}$ or —$(CH_2)_pOCH_2C(O)N(R^{12})(CH_2)_mOH$;

each $R^{16}$ is independently halo, alkyl, alkenyl, alkynyl, alkoxy, —$(CH_2)_pNR^{11}C(O)NR^{11}R^{11'}$, —$(CH_2)_pC(O)NR^{11}R^{11'}$, —$(CH_2)_pNR^{11}C(O)R^{11'}$, —$CN$, —$(CH_2)_pNR^{11}SO_2R^{11'}$, —$(CH_2)_pOC(O)R^{11}$, —$(CH_2)_pSO_2NR^{11}R^{11'}$, —$(CH_2)_pSOR^{13}$, —$(CH_2)_pCOOH$ or —$(CH_2)_pC(O)OR^{13}$;

X is $CR^{11}R^{11'}$, O, S, S(O), $S(O)_2$, or $NR^{11}$;

m is an integer between 1 and 6;

p is an integer from 0 to 5;

q and s are each independently an integer between 1 and 3; and w is an integer between 0 and 5.

2. The compound of claim 1, formula (I), wherein n is 1;

k' is a bond or O; and $R^1$ is aryl, heteroaryl, arylalkyl, or heteroarylalkyl.

3. The compound of claim 1, formula (I), wherein n is 1;

k' is O; and $R^1$ is phenylmethyl.

4. The compound of claim 1, formula (I), wherein n is 2;

k' is a bond; and $R^1$ is aryl.

5. The compound of claim 1, formula (I), wherein $R^{7a}$ and $R^{7b}$ are H;

x is 1; and y is 0 or 1.

6. The compound of claim 1, formula (I), wherein

A is $CH_2CH_2$ or $CH_2CH_2CH_2$; and each $R^4$ and $R^5$ is independently alkyl, or $R^4$ and $R^5$, when taken together, form a heterocyclic ring.

7. The compound of claim 1, formula (I), wherein $R^{7a}$ and $R^{7b}$ are each independently alkyl;

$R^4$ and $R^5$ are each independently hydrogen or alkyl; and x and y are each independently 0 or 1.

8. The compound of claim 1, formula (I), wherein Y is substituted with 1 $R^{10}$.

9. The compound of claim 8, formula (I), wherein $R^{10}$ is positioned 1,3 or 1,2, relative to the point of attachment of Y to the adjacent chain carbon.

10. The compound of claim 8, formula (I), wherein $R^{10}$ is aryl or heteroaryl, optionally substituted with up to three independent $R^{16}$.

11. The compound of claim 8, formula (I), wherein $R^{10}$ is a monocyclic aryl or monocyclic heteroaryl.

12. The compound of claim 8, formula (I), wherein $R^{10}$ is a bicyclic heteroaryl.

13. The compound of claim 8, formula (I), wherein $R^{10}$ is substituted with 1-3 $R^{16}$.

14. The compound of claim 13, formula (I), wherein $R^{16}$ is halo, alkyl, or alkoxy.

15. The compound of claim 14, formula (I), wherein $R^{16}$ is chloro, fluoro, methyl, or methoxy.

16. The compound of claim 8, formula (I), wherein $R^{10}$ is arylalkyl or heteroarylalkyl.

* * * * *